United States Patent [19]

MacLennan et al.

[11] Patent Number: 5,358,649
[45] Date of Patent: Oct. 25, 1994

[54] DIAGNOSIS FOR PORCINE MALIGNANT HYPERTHERMIA

[75] Inventors: David H. MacLennan, Toronto; Peter J. O'Brien, Guelph, both of Canada

[73] Assignees: University of Guelph; The University of Toronto Innovations Foundation, Ontario, Canada

[21] Appl. No.: 30,159

[22] PCT Filed: Dec. 20, 1991

[86] PCT No.: PCT/CA91/00457
§ 371 Date: Mar. 15, 1993
§ 102(e) Date: Mar. 15, 1993

[87] PCT Pub. No.: WO92/11387
PCT Pub. Date: Jul. 9, 1992

[30] Foreign Application Priority Data

Dec. 21, 1990 [GB] United Kingdom ............... 90 27869
May 20, 1991 [GB] United Kingdom ............... 91 10865
Sep. 9, 1991 [GB] United Kingdom ............... 91 19250

[51] Int. Cl.$^5$ ................... C12Q 1/68; C12P 19/34; C07H 21/04

[52] U.S. Cl. ..................... 435/6; 435/91.2; 536/24.31; 536/24.33

[58] Field of Search ............ 435/6, 91.2, 320.1, 435/240.2, 7.8; 530/350; 424/85.8; 536/24.33, 24.31

[56] References Cited

FOREIGN PATENT DOCUMENTS

WO91/04328 4/1991 PCT Int'l Appl. .

OTHER PUBLICATIONS

MacLennan et al.; "The Role of the Skeletal Muscle Ryanodine Receptor Gene in Malignant Hyperthermia"; *Society for Experimental Biology* (1992), pp. 189–201.

MacLennan et al.; "Malignant Hyperthermia"; *American Association for the Advancement of Science* vol. 256, pp. 789–794; May 8, 1992.

MacLennan; "The Genetic Basis of Malignant Hyperthermia" *TiPS* Aug. 1992; vol. 13; pp. 329–334.

Gillard, et al.; "A Substitution of Cysteine for Arginine 614 in the Ryanodine Receptor is Potentially Causative of Human Malignant Hyperthermia"; *Genomics* 11: 751–755 (1991).

Gillard, et al., "Polymorphisms and Deduced Amino Acid Substitutions in the Coding Sequence of the Ryanodine Receptor (RYR1) Gene in Individuals with Malignant Hyperthermia"; *Genomics* 13: 1247–1254 (1992).

Zorzato; "Molecular Cloning of cDNA Encoding Human and Rabbit Forms of the $Ca^{2+}$ Release Channel (Ryanodine Receptor) of Skeletal Muscle Sarcoplasmic Reticulum"; *The Journal of Biological Chemistry* vol. 265, No. 4; Feb. 5, 1990; pp. 2244–2256.

MacLennan et al.; "Ryanodine receptor gene is a candidate for predisposition to malignant hyperthermia" *Nature* vol. 343, No. 6258 pp. 559–561; Feb. 8, 1990.

Nelson; "Abnormality in Calcium Release from Skeletal Sarcoplasmic Reticulum of Pigs Susceptible to Malignant Hypethermia"; *The American Society for Clinical Investigation, Inc.;* vol. 72, Sep. 1983.

Mickelson, et al.,; "Enhanced $Ca^{2+}$-induced calcium release by isolated sarcoplasmic reticulum vesicles from malignant hyperthermia susceptible pig muscle"; *Biochimica et Biophysica Acta;* 862 (1986); pp. 318–328.

(List continued on next page.)

Primary Examiner—Mindy B. Fleisher
Attorney, Agent, or Firm—Bell, Seltzer, Park & Gibson

[57] ABSTRACT

A purified DNA molecule comprises a DNA sequence of approximately 15.1 kb coding for normal or mutant RYR1 protein having a molecular weight of approximately 564,740 daltons. The DNA molecule has an endonuclease restriction map of FIG. 1 and a sequence of FIG. 2.

9 Claims, 13 Drawing Sheets

OTHER PUBLICATIONS

Gahne, et al.; "Prediction of the halothane (Hal) genotypes of pigs by deducing Hal. Phi, Po2, Pdg haplotypes of parents and offspring: results from a large-scale practice in Swedish breeds"; *Animal Blood Groups and Biochemical Genetics* 16 (1985) pp. 265–283.

Chowdhary et al.; "Localization of the glucose phosphate isomerase gene to the p12-q21 segment of chromosome 6 in pig by in situ hybridization"[*Hereditas* 111; 73–78 (1989).

Archibald et al.; "The halothane sensitivity locus and its linkage relationships" *Animal Blood Groups and Biochemical Genetics* 16 (1985) pp. 253–263.

Andresen, et al.; "Close linkage established between the HAL locus for halothane sensitivitu and the PHI (phosphohexoes isomerase) locus in pigs of the Danish Landrace breed" *Nord. Vet. Med.* 1977, 29, 302–304.

Do Han Kim et al.; "Kinetic Studies of $Ca^{2+}$ Release from Sarcoplasmic Reticulum of Normal and Malignant Hyperthermia Susceptible Pig Muscles" *Biochimica et Biophysica Acta* 775 (1984) 320–327.

Ohnishi et al.; "Calcium-induced $Ca^{2+}$ release from sarcoplasmic reticulum of pigs susceptible to malignant hyperthermia"; *FEBS Letters* 161, No. 1; Sep. 1983; pp. 103–107.

Ohta, et al.; "Ca-induced Ca release in malignant hyperthermia-susceptible pig skeletal muscle"; *The American Physiological Society* 256 C358–C367 (1989).

Endo et al.; "Changes in the Ca-Induced Ca Release Mechanism in the Sarcoplasmic Reticulum of the Muscle from a Patient with Malignant Hyperthermia" *Biomedical Research* 4 (1) 83–92 (1983).

Marks, et al., "Surface Topography Anaylsis of the Ryanodine Receptor/Junctional Channel Complex Based on Proteolysis Sensitivity Mapping"; *J Biol Chem* 265: 13143–13149 (1990).

Harbitz et al., "Assignment of the Porcine Calcium Release Channel Gene, a Candidate for the Malignant Hyperthermia Locus, to the 6p11-q21 Segment of Chromosome 6"; *Genomics* 8: 001–006 (1990).

Otsu et al.; "Molecular Cloning of cDNA Encoding the $Ca^{2+}$ Release Channel (Ryanodine Receptor) of Rabbit Cardiac Muscle Sarcoplasmic Reticulum"; *J Biol Chem* 265: 13472–13483 (1990).

Fujui et al.; "Identification of a Mutation in Procine Ryanodine Receptor Associated with Malignant Hyperthermia"; *Science* 253: 448–451 (1991).

Knudson et al., "Distinct Immunopeptide Maps of the Sarcoplasmic Reticulum $Ca^{2+}$ Release Channel in Malignant Hyperthermia"; *The Journal of Biological Chemistry* 265: 2421–2424 (1990).

O'Brien, "Etiopathogenetic Defect of Malignant Hyperthermia: Hypersensitive Calcium-Release Channel of Skeletal Muscle Sarcoplasmic Reticulum"; *Veterinary Research Communications* 11 527–559 (1987).

O'Brien et al., "Malignant Hyperthermia Susceptibility: Biochemical Basis for Pathogenesis and Diagnosis"; *Can J Vet Res 54: 83–92 (1990)*.

P. J. O'Brien, "Porcine Malignant Hyperthermia Susceptibility: Hypersensitive Calcium-release Mechanism of Skeletal Muscle Sarcoplasmic Reticulum"; *Can J Vet Res* 50: 318–328 (1986).

P. J. O'Brien, "Porcine Malignant Hyperthermia Susceptibility: Increased Calcium-sequestering Activity of Skeletal Muscle Sarcoplasmic Reticulum"; *Can J Vet Res* 50: 329–337 (1986).

P. J. O'Brien, "Microassay for malignant hyperthermia susceptibility: hypersensitive ligand-gating of the Ca channel in muscle sarcoplasmic reticulum causes increased amounts and rates of Ca-release"; *Molecular and Cellular Biochemistry* 93: 53–59 (1990).

Davies et al., "Porcine malignant hyperthermia carrier detection and chromosomal assignment using a linked probe"; *Animal Genetics 19: 203–212 (1988)*.

O'Brien et al., "Porcine malignant hyperthermia susceptibility: Erythrocytic osmotic fragility"; *Am J Vet Res 46: 1451–1456 (1985)*.

O'Brien et al., "Malignant Hyperthermia Susceptibility: Cardiac Histomorphometry of Dogs and Young Market-weight Swine"; *Can J Vet Res 51: 50–55 (1987)*.

O'Brien, et al., "Compensatory increase in calcium extrusion activity of untreated lymphocytes from swine susceptible to malignant hyperthermia"; *Am J Vet Res* 51: 1038–1043 (1990).

Brenig et al., "The Porcine PHIcDNA linked to the halothane gene detects a Hind111 and Xbal RFLP in normal and malignant hyperthermia susceptible pigs"; *Nuc Acids Res* 18: 388 (1990).

Nelson et al., "Evidence for Intraluminal $Ca^{++}$ Regulatory Site Defect in Sarcoplasmic Reticulum from Malignant Hyperthermia Pig Muscle"; *Journal of Pharmacology and Experimental Therapeutics* 256: 645–649 (1991).

(List continued on next page.)

OTHER PUBLICATIONS

Fill et al., "Abnormal ryanodine receptor channels in malignant hyperthermia", *Biophys J. Biophysical Society* 57: 471–475 (1990).

Ervasti et al., "Ryanodine receptor in different malignant hyperthermia-susceptible porcine muscles"; *Am J Physiol* 260 (*Cell Physiol* 29): C58–C66 (1991).

Mickelson et al., "Abnormal Sarcosplasmic Reticulum Ryanodine Receptor in Malignant Hyperthermia"; *J Biol Chem* 263: 9310–9315 (1988).

Takeshima et al., "Primary structur and expression from complementary DNA of skeletal muscle ryanodine receptor"; *Nature* 339: 439–445 (1989).

MacKenzie et al., "The Human Ryanodine Receptor Gene; Its Mapping to 19q113.1, Placement in a Chromosome 19 Linkage Group, and Exclusion as the Gene Causing Myotonic Dystrophy"; *Am J Hum Genet* 46: 1082–1089 (1990).

P. J. O'Brien, "Porcine malignant hyperthermia susceptibility: Halothane-induced increase in cytoplasmic free calcium in lymphocytes"; *Am J. Vet Res* 50: 131–135 (1989).

```
GCCGAGGGCGGCGAGGGCGCGGGCGAAGCCCTGGAGGGCGAAGCCCTGGAGGGCGCAGACGAGGAGGTGGCCGTCCAGGAGGCCGTGCAGGAGGCGGGCCCCGGAGGGGCCGACGGGGCTGCCGTTGCCGTGGCCGAAGGGCCCTTCCGGCCCGAAGGGCTGGCCGGCCTC  13350
 G  E  G  A  G  E  G  A  G  E  A  L  E  G  A  G  D  E  E  V  A  V  Q  E  A  G  D  E  E  V  A  V  Q  E  A  G  P  G  G  A  D  G  A  V  A  V  A  E  G  G  P  F  R  P  E  G  A  G  G  L  4450

GGGGACATGGGTGACACGACGCCCTGCGAGCCGCCACCGCCCACGGGAGGGCTCCACCGGAGGAGCTCGGGGTGGATGAGGAAGGAGCTGGGGTGTGAAGGAGAAGGAGCTGCCCCGGAGGAAGGAGCTGGGGGAGAGAACTCGGGGAGCCCAGAGCCTGAGAAACTGATGCT  13500
 G  D  M  G  D  T  T  P  A  E  P  P  T  P  E  G  S  P  I  I  K  R  K  L  G  V  D  G  E  E  E  L  P  P  E  P  E  P  E  P  E  P  E  P  E  P  E  K  A  D  A  4500

GAGAATGGGGAGAAGGAAGAAGTCCCCAAGCCCCCACCGCCCGAGCCCCCACCGCCCCAAGAGACAGCTCCCATTTGCCATTGCCTTCCTCGCCTTCCTGGATTCTTGGACACTCTCGGATCTTATAAGGTCTCACCAGGAGAGCTCGGACTCTCCACCAGGGAGGTACAGAGGGTGAAGTTCTTG  13650
 E  N  G  E  K  E  E  V  P  K  P  P  P  P  P  P  P  K  K  T  A  P  P  P  P  P  P  P  P  K  K  E  E  G  S  G  G  L  E  F  W  G  E  L  E  V  Q  R  V  K  F  L  4550

AACTACTTCTCCCGGAACTTTTACACTCTCCGATTCCTTGCCCTTCTTGCCATTGCCATTCAACTTGCATTTGCCTCTCTTGGAATTCATCTTGCTGTCTTGTTTATAAGGTCTCACCAGGGAGGATGAAGATGGAAGGGTCTGCAAGGCTCACGGGGAGCCAGCCGGAGCCTACAGCGCTGAGCCTGCCACACGCTG  13800
 N  Y  L  S  R  N  F  Y  T  L  R  F  L  A  F  L  A  F  A  I  N  F  I  L  L  F  Y  K  V  S  D  S  P  P  G  E  D  D  M  E  G  S  A  A  G  D  L  S  G  4600
                                                           G

GCCAGGCCTCGTGGTGGGCCGGGCCGGGGGGGGGGGGGGGCCCCGGAGCCCACCTCTCGGTGTGGGCTCGGAGGGGCCGAGAGGAGGTGAAGGCGAGGAGGTGGAAGGGAGGAGAGGAGGAGAGGAGGAGAATGGTATATACTTCCTGGAGAGAGAGAACTGGACCCTCGAGTTTGACGGGCTCTACACTGGAGCAGCCGAGAGCAGGCGGAGTACTCACTG  13950
 A  G  S  G  G  G  S  G  W  G  S  G  A  G  E  E  V  E  G  D  E  D  E  N  M  V  Y  Y  F  L  E  E  S  T  G  Y  M  E  P  A  L  R  C  L  S  L  L  H  T  L  4650

GTGGCCCTTTCTGCATCATAGGCTACAACTGCCTCAAGGTGCCCCTGGATCTTTAAGCGGAGAAGGAACTGGACTCTTTGACGGAGTTTGACGGGCTCTACACTCGAGTTTTTAAGCGGGAGAAGGAACTTGAGTTCTTTGAAGAGGCTGGGGCTCAAGGAACTTGGAGGGGCCGAAGGGAAGCATTCTGCTCGAGATCACAGCC  14100
 V  A  F  L  C  I  I  G  Y  N  C  L  K  V  P  L  V  I  F  K  R  E  K  E  L  A  R  K  L  E  F  D  G  L  Y  I  T  E  Q  P  E  D  D  D  V  K  G  Q  W  D  4700

CGGCTGGTGCTCAACACCGTCTTCCCCAGCAACTACTGGGACAAGTTGTCAAGCGGAAGTCCTGACAAGCACCGGAAGATCGCAAGATCGCAATCGCCGAGTCTCGGCAGCGGCGAGCTGCTCGGGATCTACGGCGGGGAGATCGCCTGGTATGGATGGATCTGCCACCTGCTCGGGATGGATCTGGCTACATGGTGATGTCCCTCCTGGGT  14250
 R  L  V  N  T  P  S  F  P  P  S  N  Y  W  D  K  F  V  K  R  K  V  L  D  K  H  G  D  I  Y  G  R  E  R  I  A  E  L  L  G  M  D  L  A  T  L  E  I  T  A  4750

CACAAGAGGCGCAAGCCTGAACCACCGCCAGGGCTGCTCACCTGGCTGCTCACCCGGCTGGATATTGCCATGGGGGTCAAGACAACTCGCTGCTGCTCGTCCTGACGCCAAATGGCAAAACCTGGTCAGATGCCGTGTCTTGGCGGTTGTTGGGCTGGTACATGGTGATGTCCCTCCTGGGT  14400
 H  N  E  R  K  P  E  P  P  P  G  L  L  T  W  L  M  S  I  D  V  K  Y  Q  I  W  K  F  G  V  I  F  T  D  N  S  F  L  Y  L  G  W  Y  M  V  M  S  L  L  G  4800

CACTACAACAACTTCTTCCGCAAGTTCTACAACAAGAGCGAGGATGAGGACCCAGACATGAAGTGTGATGATGACATGACCTGTTACATGTATGTGGGTGTCCGGGCAGGCGGCATTGGGGGCATTGGGGACGAGATCGAG  14550
 H  Y  N  N  F  F  A  A  H  L  L  D  I  A  M  G  V  K  T  L  R  T  I  L  S  S  V  T  H  N  G  K  Q  L  V  M  T  V  G  L  L  A  V  V  V  L  Y  T  4850

GTGGTGGCCTTCAACTTCTTCCGGAAGTTCTACCGGCAGTCCTGGTGTCTTTGACATCACCTTCTTCTTTGTGATCGTGCTGCTTGCAATCATCCAGGGTCTGATCATTGATGCCTTTGGGGAACTCCGAGACCAACAAGAGCAAGTCGAGAGAA  14700
 V  V  A  F  N  F  F  R  K  F  Y  N  K  S  E  D  E  D  E  P  D  M  K  C  D  D  M  T  C  Y  L  F  H  M  Y  V  G  V  R  A  G  G  I  G  D  E  I  E  4900

GACCCAGCAGGAGATGAATATGAGCTCTACCGGGTCGTGGTCTTTGACATCACCTTCTTCTTTGTGATCGTGCTGCTTGCAATCATCCAGGGTCTGATCATTGATGCCTTTGGGGAACTCCGAGACCAACAAGAGCAAGTCGAGAGAA  14850
 D  P  A  G  D  E  Y  E  L  Y  R  V  V  V  F  D  I  T  F  F  F  F  V  I  V  L  L  A  I  I  Q  G  L  I  I  D  A  F  G  E  L  R  D  Q  Q  E  Q  V  R  E  4950
```

FIG. 2J.

```
GATATGAGACCAAGTGCTTCATCTGTGCAGCGAGATTACTTTGATACAGACACCACCGGTTCGAGACCACCACCGCTAGAGGAGCACAACTGGCCAATTACATGTTTTTCCTGATGTATCTGATAAACAAGGAGACAGAA  15000
 D  M  E  T  K  C  F  I  C  G  I  S  D  Y  F  D  T  T  P  H  G  F  E  T  H  T  L  E  E  H  N  L  A  N  Y  M  F  F  L  M  Y  L  I  N  K  D  E  T  E         5000

CACACGGGTCAGGAGTCTTATGTCTGAAGATGCTGGAGATAGAGATACCAAGAGAGAATGTACCAAGACAGTACGCTTAGCTGAGACCAGTATGAGGACCGAAGCAGTATTCCTGAAGACTATGAGGACCAGTATGAGGACCACCCCCAGCTGGCCGCCACCCCACCCCTCAGTGCCTTG  15150
 H  T  G  Q  E  S  Y  V  W  K  M  Y  Q  E  R  C  W  D  F  F  P  A  G  D  C  F  R  K  Q  Y  E  D  Q  L  S  ***                                                   5035

TTTTCACGACAAGCCCCTTAGCCCCCCCAAACCTCCCCCAAGGCAGCTAGGGGAGCAGTGACCATGCAGTGGAGAATAAAGTCTCTGCTACACCCCT  15249
```

```
                                                                    T                           C
1811 GTTCCCTGTGTGTGTGCAATGGTGCCGTGCGCTCCAACCAAGATCTCATTACTGAGAACTTGCTGCCTGGC 1884
604  C  S  L  C  V  C  N  G  V  A  V  R  S  N  Q  D  L  I  T  E  N  L  L  P  G  628
                                        C
```

```
GACAAGCATGGAGGAGAACCACAAGgtgggcctctcatccctccaattctgcactcttgatcttcccaccccctcttcactcttacctgactcctctg
 D  K  H  G  R  N  H  K
ccacatgcttctagctcaatacaaagtctcaaactcctgttcttgttttttgtttttatggctgaactgtgcaaatgaagtttccagcaagggg tgaaccagagctatagtgctgctggcctacaccacacagctccatcaacaagccagatccgagtcgtgtctgccactcacagtcatgcaatacag atccttaaccactgagcgaggccaggagcgaacctgcaacctcacgaatactagtggtttgtaaccactgagccacaatggaactcctcaaag tcattcttaaatgcattctgggccccgatatgcttcctagatctttgaagtgttttctaaatgtctaatgcaggcggctgcatatacaogct ccagtttgccacacagtcctaccagtcccactgaattaattattctaaccacctcatgtatggacaaatcccactggccgccgaagatgcacgttggtg accccgccatcagaacctgtcttggtctcgtgctctcgcactgaccggcctttcacttcttgcctccgacttctcacccctgctccgtctctc ctttcctcctctgctgatgccgatccatcccctcaccagcccctggtctccaccagacctttcttgaccttgatctccctgtgtcatcctgacct tcccgcttcaccaccctcctgatccacccctcctgactcaccagcggtttccacccacagtgccctcacacctggcttccacctggttcccacctggttccacctggttcccacctc cccgcaagtgccctcacacctgacctgaccctagGTCCTGGATGTCCTGTGTGTCCTGTGTGTGCAATGGTGTGCCGTCCTCCAA
                            V  L  D  V  L  C  V  C  N  G  V  A  V  R  S  N
                                                                        T    C CCAAGATCTCATTACTGAGAACTTGCTCCCCTGGCCGAGTTCTCTGCAGACTTCACAAACCTCATCAACTATGTCACCAGgtctgccccaacctttgac
 Q  D  L  I  T  E  N  L  L  P  G  R  E  L  L  Q  T  N  L  I  N  Y  V  T  S cccagagcttagaacctccaccacccgccgactcaggagactccactccggtgaatgccttcctccaccccgtccctgactaatgccagtc
```

FIG.6B.

cccacccctgtgtggtgcttgtgtcccagcttgtcccctgctttcttctattcctggctttctactcttcccctgctttctcctgtctcttctctc tttctgtgttgctctctttgtctctgtcatctctatttctcctccatctctcccagtctttttcccagtctctctgtctttgagtgtctctctg tctgtctctgcctctctttctctgcctctttctcctgtctctgtcctgtctctccagtgctctctccatgctctcggtatgtgtctttccctctccc cccagccttccctctgctgctcctccagccctgctctctccagccctcatcctctgtccattctcctgtccatttcctctgcagCATCCGCCCAACATCTTTGTGGG
                                                                                                 I  R  P  N  I  F  V  G

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 15378 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
( B ) CLONE: Porcine RYR1 Gene ( v i i i ) POSITION IN GENOME:
( C ) UNITS: bp ( x i ) SEQUENCE DESCRIPTION: SEQ ID NO:1:

| | | | | | | |
|---|---|---|---|---|---|---|
| CCCCGCGGGT | GCCTCTGGGG | TTCCCAGAGG | TCTCCGACCC | CAGCCGCCCC | CGGCCCGCCC | 60 |
| GCCCGCCCAG | CCTGCGGCCC | CCTCCTCCTA | TTCCCTGACC | TCAGCCCCGG | CTCCTCGGGC | 120 |
| CTCGACATCA | TGGGTGACGG | AGGAGAGGGC | GAAGATGAGG | TCCAGTTTCT | GCGGACAGAC | 180 |
| GACGAGGTGG | TCCTGCAGTG | CAACGCTACG | GTGCTCAAGG | AGCAGCTCAA | GCTCTGCCTG | 240 |
| GCCGCCGAGG | GCTTCGGCAA | CCGCCTCTGC | TTCCTGGAAC | CCACCAGCAA | CGCCCAGAAT | 300 |
| GTGCCCCCCG | ATCTGGCCAT | CTGCTGCTTC | GTCCTGGAGC | AGTCCCTGTC | CGTCCGAGCC | 360 |
| CTGCAGGAGA | TGCTGGCCAA | CACCGTGGAG | GCCGGCGTGG | AGTCATCCCA | GGGCGGGGGC | 420 |
| CATAGGACGC | TCTTGTATGG | CCACGCCATC | CTGCTCCGGC | ACGCGCACAG | TGGCATGTAT | 480 |
| CTGAGCTGCC | TCACCACCTC | CCGTTCCATG | ACTGACAAGC | TGGCCTTCGA | CGTGGGACTG | 540 |
| CAGGAGGATG | CGACAGGAGA | GGCCTGTTGG | TGGACTACAC | ACCCGGCCTC | CAAGCAGAGG | 600 |
| TCGGAAGGAG | AGAAGGTTCG | AGTAGGGGAT | GACCTCATCC | TCGTCAGTGT | CTCCTCTGAG | 660 |
| CGTTACCTGC | ACCTGTCGAC | AGCCAGTGGG | GAGCTCCAGG | TTGACGCCTC | CTTCATGCAG | 720 |
| ACACTGTGGA | ACATGAACCC | CATCTGCTCT | GGCTGTGAAG | AAGGCTATGT | GACTGGGGGT | 780 |
| CACGTCCTCC | GCCTCTTTCA | CGGACACATG | GATGAGTGCC | TGACCATCTC | CCCCGCTGAC | 840 |
| AGTGATGACC | AGCGCAGACT | TGTCTACTAC | GAGGGTGGAT | CTGTGTGCAC | CCACGCCCGC | 900 |
| TCCCTCTGGA | GACTGGAACC | GCTGAGAATC | AGCTGGAGTG | GGAGCCACCT | GCGCTGGGGC | 960 |
| CAGCCGCTTC | GCATCCGGCA | TGTCACCACC | GGGAGGTACC | TGGCGCTCAT | CGAGGACCAG | 1020 |
| GGCCTGGTGG | TGGTTGATGC | CAGCAAGGCC | CACACCAAGG | CCACCTCCTT | CTGTTTCCGC | 1080 |
| ATTTCCAAGG | AGAAGCTGGA | TACGGCCCCC | AAGCGGGACG | TGGAGGGCAT | GGGCCCCCCT | 1140 |
| GAGATCAAGT | ATGGGGAGTC | ACTGTGCTTC | GTGCAGCATG | TGGCCTCGGG | CCTGTGGCTT | 1200 |
| ACCTATGCTG | CCCCAGACCC | CAAGGCCCTG | CGGCTCGGCG | TGCTCAAGAA | GAAGGCCATT | 1260 |
| CTGCACCAGG | AAGGCCACAT | GGACGATGCA | CTGTCACTGA | CCCGCTGTCA | GCAGGAGGAG | 1320 |
| TCCCAGGCGG | CCCGCATGAT | CTATAGCACT | GCTGGCCTCT | ACAACCACTT | CATCAAGGGC | 1380 |
| CTGGACAGCT | TCAGCGGAAA | GCCACGGGGC | TCTGGGCCC | CGGCTGGCAC | AGCGCTACCC | 1440 |
| CTCGAGGGCG | TCATCCTGAG | CCTGCAGGAC | CTCATCGGCT | ACTTTGAGCC | GCCCTCGGAA | 1500 |
| GAGCTGCAGC | ACGAGGAGAA | GCAGAGCAAG | CTGCGCAGCC | TGCGCAACCG | CCAGAGCCTC | 1560 |
| TTCCAGGAGG | AGGGGATGCT | CTCCCTGGTC | CTGAATTGCA | TTGACCGCCT | AAATGTCTAC | 1620 |

```
ACCACTGCTG CCCACTTTGC TGAGTTTGCA GGAGAGGAGG CAGCCGAGTC CTGGAAAGAG   1680
ATTGTGAACC TGCTGTATGA GATCCTGGCC TCTCTGATCC GTGGCAATCG TGCCAACTGT   1740
GCCCTTTTCT CCAACAACTT GGATTGGCTG GTCAGCAAGC TGGATCGACT GGAGGCCTCC   1800
TCAGGGATCC TGGAGGTGCT GTACTGTGTC CTGATTGAGA GTCCTGAGGT CCTGAACATC   1860
ATCCAGGAGA ACCACATCAA GTCCATCATC TCCCTTCTGG ACAAGCATGG GAGGAACCAC   1920
AAGGTGCTGG ATGTCCTGTG TTCCCTGTGT GTGTGCAATG GTGTGGCCGT GTGCTCCAAC   1980
CAAGATCTCA TTACTGAGAA CTTGCTCCCT GGCCGCGAGC TTCTGCTGCA GACAAACCTC   2040
ATCAACTATG TCACCAGCAT CCGCCCCAAC ATCTTTGTGG CCGAGCAGA GGGCACCACA   2100
CAGTACAGCA AATGGTACTT TGAGGTCATG GTGGACGAAG TGGTTCCATT CCTGACAGCT   2160
CAGGCCACCC ACCTGCGGGT GGGCTGGGCC CTCACCGAAG CTACAGCCC CTACCCTGGG   2220
GGCGGCGAGG GCTGGGGCGG CAACGGGGTC GGCGATGACC TCTATTCCTA CGGCTTTGAC   2280
GGGCTGCATC TCTGGACAGG ACACGTGCCA CGCCTGGTGA CTTCCCCAGG GCAGCACCTT   2340
CTGGCCCCCG AGGACGTGGT CAGCTGCTGC CTGGACCTCA GCGTGCCGTC CATCTCCTTC   2400
CGCATCAACG GCTGCCCCGT GCAGGGCGTC TTCGAGGCCT TCAACCTCAA CGGGCTCTTC   2460
TTCCCCGTCG TCAGCTTCTC GGCCGGTGTC AAGGTGCGGT TCCTCCTTGG GGGCCGCCAC   2520
GGCGAATTCA AGTTCCTCCC TCCGCCTGGC TACGCCCCTT GCCACGAGGC TGTGCTCCCA   2580
CGAGAGCGAC TCCGTCTGGA ACCCATCAAG GAGTATCGGC GAGAAGGGCC CCGGGGACCC   2640
CACCTGGTGG CCCCAGCCG CTGCCTCTCA CACACCGACT TTGTGCCCTG CCCGGTGGAC   2700
ACTGTCCAGA TTGTCCTGCC TCCCCATCTG GAGCGTATCC GGGAGAAGCT GGCAGAGAAC   2760
ATCCATGAAC TCTGGGCGCT GACGCGCATC GAGCAGGGCT GGACCTATGG CCCGGTTCGG   2820
GATGACAATA AGCGGCTGCA CCCGTGTCTC GTGGACTTCC ACAGCCTCCC GGAGCCCGAG   2880
AGGAATTACA ACCTGCAGAT GTCGGGGGAG ACGCTCAAGA CTCTGCTGGC GCTGGGCTGC   2940
CACGTGGGCA TGGCGGACGA GAAGGCAGAG GACAACCTGA GGAAGACGAA ACTCCCCAAG   3000
ACGTACATGA TGAGCAATGG GTACAAGCCA GCGCCACTGG ACCTGAGCCA TGTGAGACTG   3060
ACGCCTGCGC AGACCACGCT GGTGGACCGG CTGGCGGAGA ACGGGCACAA CGTGTGGGCC   3120
CGAGACCGAG TGGCCCAGGG CTGGAGCTAC AGTGCTGTGC AGGACATCCC AGCGCGCCGC   3180
AACCCTCGCC TCGTGCCCTA CCGCCTGCTA GACGAGGCCA CCAAGCGCAG CAACCGGGAC   3240
AGCCTTTGCC AGGCTGTGCG CACCCTGCTG GGCTACGGCT ACAACATCGA GCCGCCCGAC   3300
CAGGAGCCCA GTCAGGTGGA GAGCCAGTCT CGCTGGGACC GTGTGCGCAT CTTCCGGGCT   3360
GAGAAGTCCT ATGCGGTGCA GAGCGGCCGC TGGTACTTCG AGTTCGAGGC CGTCACCACG   3420
GGCGAGATGC GAGTGGGCTG GCGCGGCCT GAGCTGCGGC TGATGTGGA CTGGGAGCC   3480
GATGAGCTGG CCTATGTCTT CAATGGGCAC CGGGGTCAGC GCTGGCACTT GGGCAGCGAA   3540
CTGTTTGGGC GTCCCTGGCA GTCGGGCGAT GTGGTGGGCT GCATGATCGA CCTCACAGAG   3600
AACACCATTA TCTTCACGCT CAACGGCGAG GTCCTCATGT CCGACTCGGG CTCTGAAACC   3660
GCCTTCCGGG ATATCGAGGT TGGGGATGGC TTCCTGCCCG TCTGCAGCTT GGGACCTGGC   3720
CAGGTGGGCC ACCTGAACCT GGGCCAGGAT GTGAGCTCCC TGCGGTTCTT TGCCATCTGC   3780
GGCCTCCAGG AAGGTTTTGA GCCATTCGCC ATCAACATGC AGCGTCCCGT CACTACCTGG   3840
TTCAGCAAAA GCCTTCCCCA GTTTGAGGCC GTGCCCTCG AGCATCCCCA CTACGAGGTG   3900
TCTCGTGTGG ACGGCACCGT GGACACGCCC CCTGCCTGC GCCTGACCCA CCGCACCTGG   3960
GGCTCCCAGA ACAGTCTGGT GGAGATGCTC TTTCTCCGGC TGAGCCTCCC TGTCCAGTTC   4020
CACCAGCACT TCCGCTGCAC CGCAGGGGCC ACCCCCTGG CACCACCTGG CCTGCAGCCC   4080
```

```
CCTGCTGAGG ATGAGGCCCG GGCAGCAGAA CCTGATCCCG ACTATGAAAA CCTGCGCCGC    4140
TCAGCTGGGC GCTGGGGCGA GGCTGAGGGC GGCAAAGAAG GAACTGCCAA GGAGGGGGCA    4200
CCCGGGGGCA CTGCCCAGGC TGGGGTAGAG GCCCAGCCTC CCAGGGCAGA AAATGAGAAG    4260
GATGCTACCA CAGAGAAGAA CAAGAAGAGA GGGTTCCTAT TCAAGGCCAA GAAGGCTGCC    4320
ATGATGACCC AGCCACCGGC CACCCCGACT CTGCCCAGAC TCCCTCACGA GGTGGTGCCT    4380
GCTGATGACC GCGATGACCC TGACATCATC CTCAACACCA CCACGTACTA TTACTCGGTG    4440
AGGGTCTTCG CTGGCCAGGA GCCCAGCTGC GTGTGGGTGG CTGGGTCAC CCCTGACTAC     4500
CACCAGCACG ACATGAACTT CGACCTCACC AAGGTCCGGG CGGTGACGGT GACCATGGGG    4560
GATGAGCAGG GCAACATCCA CAGCAGCCTC AAGTGCAGCA ACTGCTACAT GGTGTGGGGT    4620
GGAGACTTTG TGAGCCCCGG GCAGCAGGGC CGGATCAGCC ACACAGACCT TGTCATCGGC    4680
TGCCTGGTGG ACTTGGCTAC TGGGCTTATG ACCTTCACCG CCAACGGCAA AGAGAGCAAC    4740
ACCTTTTTCC AGGTGGAACC CAACACAAAG CTGTTTCCAG CCGTCTTTGT CCTGCCCACA    4800
CACCAGAACG TCATCCAGTT TGAGCTGGGG AAGCAGAAGA ACATCATGCC GCTGTCCGCT    4860
GCCATGTTTC TGAGCGAGCG CAAGAACCCG GCCCCGCAGT GCCCGCCCCG GCTCGAGATG    4920
CAGATGCTGA TGCCCGTGTC GTGGAGCCGC ATGCCCAACC ACTTCCTGCG GGTGGAGACC    4980
CGCCGTGCCG GCGAGCGGCT TGGCTGGGCG GTGCAGTGTC AGGAGCCACT GACCATGATG    5040
GCACTGCACA TCCCTGAAGA GAACCGATGC ATGGACATCC TGGAGCTGTC CGAGCGCTTG    5100
GACCTGCAGC AGTTCCACTC GCACACCCTC CGCCTCTACC GCGCTGTGTG CGCCCTGGGC    5160
AACAACCGCG TGGCGCATGC GCTGTGCAGC CACGTGGACC AGGCGCAGCT GCTGCACGCC    5220
CTGGAGGACG CGCACCTGCC CGGCCCTCTG CGCGCAGGTT ACTACGACCT CCTCATCAGC    5280
ATCCACCTGG AAAGCGCCTG CCGCAGCCGC CGCTCCATGC TCTCTGAGTA CATCGTCCCC    5340
CTCACGCCGG AGACCCGCGC CATCACTCTC TTCCCGCCTG GAAAAGGAC GGAAAACGGT     5400
CCCCGCCGCC ACGGCCTGCC CGGTGTCGGC GTCACCACCT CGCTGAGGCC TCCGCACCAT    5460
TTCTCAGCCC CCTGTTTTGT GGCAGCCCTG CCAGCTGTTG GAGCGGCCGA AGCCCCGGCC    5520
CGCCTCAGCC CCAGCATCCC TCTGGAGGCT CTGCGGGACA AAGCACTAAG AATGCTGGGG    5580
GAGGCGGTAC GAGACGGTGG GCAGCACGCA CGCGACCCTG TCGGGGGCTC TGTGGAGTTC    5640
CAGTTTGTGC CCGTGCTCAA GCTCGTGTCC ACCCTGCTGG TGATGGGCAT CTTTGGTGAT    5700
GAGGACGTGA AGCAGATCTT GAAGATGATT GAGCCCGAAG TATTCACTGA GGAAGAAGAG    5760
GAGGAGGAGG AGGAAGAAGA GGAGGAAGAA GAAGATGAGG AGGAGAAGGA GGAGGATGAG    5820
GAGGAGGAGG CACGGGAGAA GGAGGATGAG GAAAAGAGG AAGAGGAGAC AGCAGAAGGG    5880
GAAAAGAAG AATACTTGGA GGAAGGGCTG CTCCAGATGA AGTTACCAGA GTCTGTGAAG    5940
TTACAGATGT GTAATCTGTT GGAGTATTTC TGTGACCAAG AGCTGCAGCA CCGTGTGGAG   6000
TCCCTGGCAG CCTTTGCAGA ACGCTACGTG GACAAGCTCC AGGCCAACCA GAGGGACCGC    6060
TATGGCATCC TCATGAAGGC CTTCACCATG ACCGCTGCCG AGACTGCCCG ACGTACTCGC    6120
GAGTTCCGCT CCCCACCCCA GGAGCAGATC AACATGCTAT TGCACTTCAA AGATGGCGAG    6180
GATGAGGAAG ATTGTCCTCT TCCTGATGAG ATCCGGCAGG ATTTGCTGGA ATTCCATCAA    6240
GACCTGTTGA CTCACTGTGG AATTCAGCTG GAGGGGGAGG AGGAAGAACC AGAGGAAGAA    6300
GCCACCCTGG GCAGCCGCTT GATGAGCCTG TTGGAGAAGG TGCGGCTGGT GAAGAAGAAG    6360
GAGGAGAAAT CCGAGGAGGA GCCACCTGCC GAGGAGAGCA AACCCAGTC ACTGCAGGAG     6420
CTGGTGTCTC ACACAGTGGT GCGCTGGGCC CAAGAGGACT TTGTGCAGAG CCCGGAGCTG    6480
GTACGGGCCA TGTTCAGCCT CCTGCACCGG CAGTACGACG GGCTCGGGGA GCTGCTGCGT    6540
```

```
GCCCTGCCCC GCGCCTACAC CATCTCCCCC TCCTCTGTGG AGGACACCAT GAGCCTACTC    6600
GAGTGCCTCG GCCAGATCCG GTCACTGCTC ATCGTGCAGA TGGGCCCCCA GGAGGAAAAC    6660
CTCATGATCC AGAGCATTGG GAACATCATG AACAACAAAG TCTTCTACCA ACACCCGAAC    6720
TTGATGCGGG CACTGGGCAT GCACGAGACA GTCATGGAGG TCATGGTGAA TGTCCTCGGC    6780
GGCGGGGAGT CCAAGGAGAT CCGCTTCCCC AAGATGGTGA CGAGCTGCTG CCGCTTCCTC    6840
TGCTACTTCT GCCGCATCAG CCGGCAGAAC CAGCGCTCCA TGTTTGACCA CCTGAGCTAC    6900
CTGCTGGAGA ACAGTGGCAT TGGCCTGGGC ATGCAGGGCT CCACGCCCCT GGATGTGGCC    6960
GCTGCCTCCG TCATTGACAA CAACGAGCTG CTTTGGCAT TGCAGGAGCA GGACCTGGAG    7020
AAGGTGGTGT CCTACCTGGC AGGCTGTGGC CTCCAAAGCT GCCCAATGCT CCTGGCCAAA    7080
GGGTACCCGG ACATCGGCTG GAACCCCTGC GGTGGTGAGC GCTACCTGGA CTTCCTGCGC    7140
TTTGCTGTCT TTGTCAATGG TGAGAGCGTG GAGGAGAACG CCAACGTGGT GGTGCGGCTG    7200
CTGATCCGCA AGCCCGAGTG CTTCGGGCCT GCCCTGCGGG GCGAGGGCGG CTCGGGGCTG    7260
CTGGCCACCA TCGAGGAGGC CATCCGCATC TCCGAGGACC CCGCGCGGGA CGGCCCTGGC    7320
GTCCGCAGGG ACCGGCGGCG AGAGCACTTC GGGGAGGAGC CCCCTGAAGA AAACCGGGTG    7380
CACCTGGGAC ACGCCATCAT GTCCTTCTAT GCTGCCTTGA TTGACCTGCT GGGACGCTGT    7440
GCACCAGAGA TGCATCTGAT CCAAGCCGGC AAGGGCGAGG CCCTGCGGAT CCGTGCCATC    7500
CTGCGCTCCC TCGTGCCCCT GGACGATCTC GTGGGCATCA TCAGCCTCCC ACTGCAGATA    7560
CCCACCCTGG GCAAAGACGG GGCTCTAGTA CAGCCAAAGA TGTCAGCATC CTTCGTGCCG    7620
GACCACAAGG CGTCGATGGT GCTCTTCCTG ACCGTGTGT ACGGCATCGA GAACCAGGAC    7680
TTCTTGCTGC ACGTGCTGGA CGTGGGGTTC CTGCCTGATA TGAGGGCGGC CGCCTCGCTG    7740
GACACGGCCA CTTTCAGCAC CACGGAAATG GCACTGGCGC TGAACCGCTA CCTATGCCTG    7800
GCCGTGCTGC CACTCATCAC CAAGTGTGCG CCACTCTTCG CGGGAACCGA GCATCGTGCC    7860
ATCATGGTGG ACTCCATGCT TCACACGGTG TACCGCCTGT CCCGTGGCCG CTCGCTCACC    7920
AAGGCGCAGC GCGACGTTAT CGAGGAATGC CTGATGGCGC TCTGCAGGTA CATCCGCCCG    7980
TCCATGCTAC AGCACCTGCT TCGGCGCCTG GTGTTCGACG TGCCCATCCT TAACGAGTTC    8040
GCCAAGATGC CCCTCAAGCT CCTCACCAAC CACTATGAGC GTTGCTGGAA GTACTACTGC    8100
CTCCCCACAG GCTGGGCCAA CTTCGGAGTC ACCTCGGAGG AAGAGCTGCA CCTCACTCGC    8160
AAACTCTTCT GGGGCATCTT TGACTCGCTG GCCCATAAGA AATATGACCC AGAGCTGTAC    8220
CGCATGGCTA TGCCCTGCCT GTGTGCCATC GCAGGGCCC TGCCCCCCGA CTACGTGGAC    8280
GCCTCATACT CATCCAAGGC TGAGAAAAAG CTACCGTGG ACGCTGAAGG CAACTTCGAT    8340
CCTCGGCCTG TGGAGACTCT CAACGTGATC ATCCCAGAGA AGCTGGACTC CTTCATCAAC    8400
AAGTTTGCCG AGTACACGCA TGAGAAGTGG GCCTTCGACA AGATCCAGAA CAACTGGTCC    8460
TATGGGGAGA ACATAGATGA GGAGCTGAAG ACCCATCCCA TGCTGAGGCC CTACAAGACC    8520
TTTTCAGAGA AGGACAAAGA GATTTATCGC TGGCCCATCA AAGAGTCCTT GAAGGCCATG    8580
ATTGCCTGGG AATGGACGAT AGAGAAAGCC AGGGAGGGTG AGGAGGAGAA GACGGAGAAG    8640
AAAAAAACAC GGAAGATATC CCAAAGTGCC CAGACCTATG ATGCTCGAGA AGGCTACAAC    8700
CCCCAGCCCC CTGACCTCAG CGGCGTTACC CTGTCCCGGG AGCTGCAGGC TATGGCAGAA    8760
CAACTGGCGG AAAATTACCA CAACACGTGG GGACGGAAGA AGAAGCAGGA GCTGGAAGCC    8820
AAGGGTGGTG GGACCCACCC CTTGCTGGTT CCCTACGACA CTCTCACGGC CAAGGAGAAG    8880
GCACGAGATA GAGAGAAGGC CCAGGAGCTG CTGAAGTTCC TGCAGATGAA TGGCTATGCA    8940
GTCACCAGGG GCCTTAAGGA CATGGAACTG GACACATCTT CCATTGAGAA ACGGTTTGCC    9000
```

```
TTTGGCTTCC TGCAGCAGTT GCTGCGCTGG ATGGACATTT CTCAGGAGTT TATCGCCCAC    9060
CTGGAGGCTG TGGTCAGCAG TGGACGAGTG GAAAAGTCCC CCCATGAACA GGAGATAAAA    9120
TTCTTTGCCA AGATCCTGCT CCCTTTGATC AACCAGTACT TCACCAACCA CTGCCTCTAT    9180
TTTCTGTCCA CACCGGCCAA AGTGCTGGGC AGCGGCGGCC ACGCCTCCAA CAAGGAGAAG    9240
GAAATGATCA CCAGCCTCTT CTGCAAGCTG GCCGCTCTTG TCCGTCACCG AGTCTCTCTC    9300
TTTGGGACGG ATGCCCCAGC CGTGGTCAAC TGCCTTCACA TCCTGGCACG TTCCTGGAC     9360
GCGAGGACAG TGATGAAGTC TGGCCCCGAG ATTGTGAAGG CCGGCCTCCG TTCCTTCTTC    9420
GAGAGCGCCT CGGAGGACAT CGAGAAGATG GTGGAGAACC TGCGCCTGGG CAAGGTGTCA    9480
CAGGCGCGCA CGCAGGTCAA GGGCGTGGGC CAGAACCTCA CCTACACCAC CGTGGCCCTG    9540
CTGCCTGTGC TAACCACCCT CTTCCAGCAC ATCGCCCAGC ACCAATTTGG AGACGACGTA    9600
ATCCTGGATG ACGTTCAGGT CTCTTGCTAT CGAACGCTGT GCAGTATCTA CTCTCTGGGA    9660
ACCACCAGGA ACCCTTACGT GGAAAAGCTG CGGCCAGCCC TCGGTGAGTG CCTGGCCCGC    9720
CTGGCAGCAG CCATGCCAGT GGCATTCCTG GAGCCCAGC TGAACGAGTA CAATGCCTGC     9780
TCAGTGTACA CCACCAAGTC TCCCCGGGAG CGGGCCATCC TGGGGCTCCC CAACAGCGTG    9840
GAGGAGATGT GCCCGGATAT TCCGGTGCTG GAGCGGCTCA TGGCAGACAT CGGGGGGCTG    9900
GCCGAGTCGG GGGCCCGCTA CACGGAGATG CCACACGTCA TTGAGATCAC ACTGCCCATG    9960
CTGTGCAGCT ACCTGCCCCG CTGGTGGGAA CGCGGGCCCG AGGCGCCCCC ACCGCCCTG    10020
CCCGCGGGAG CCCCTCCGCC CTGCACAGCT GTCACTTCCG ACCACCTCAA CTCCCTGCTG   10080
GGAAACATCC TGCGGATCAT CGTCAACAAC TTGGGCATCG ACGAGGCCTC ATGGATGAAG   10140
CGGCTGGCCG TGTTCGCCCA GCCCATCGTG AGCCGGGCCC GGCCCGAGCT CCTGCACTCA   10200
CACTTCATCC CCACCATCGG GCGGCTGCGC AAACGGGCCG GAAGGTGGT GGCCGAGGAG    10260
GAGCAGCTGC GCCTGGAGGC CAAGGCAGAA GCCGAGGAAG GGAGCTCCT GGTGCGGGAT    10320
GAGTTCTCTG TGCTCTGCCG GGACCTGTAT GCCCTCTACC CACTGCTCAT CCGCTACGTG    10380
GACAACAACA GGGCACACTG GCTGACGGAA CCCAATCCCA GCGCGGAGGA GTTGTTCCGG    10440
ATGGTGGGCG AGATCTTCAT CTACTGGTCC AAGTCCCACA ACTTCAAGCG CGAGGAGCAG    10500
AACTTTGTGG TCCAGAATGA GATCAACAAC ATGTCATTTC TGACCGCCGA CAACAAGAGC    10560
AAAATGGCCA AGTCGGGTGG CTCAGACCAG GAACGCACCA AGAAGAAGCG CCGGGGGGAC    10620
CGGTACTCTG TGCAGACATC GCTGATCGTG CCACACTCA AGAAGATGCT GCCCATCGGC     10680
CTGAACATGT GTGCGCCCAC CGACCAGGAA CTCATCACGC TGGCCAAGAC CCGCTATGCC    10740
CTGAAAGACA CAGATGAGGA GGTCCGGGAA TTTCTGCAAA ACAACCTTCA CCTTCAGGGA    10800
AAGGTCGAAG GTTCCCCGTC TCTGCGCTGG CAGATGGCCC TGTACCGGGG CCTCCCGGGC    10860
CGCGAGGAGG ACGCTGACGA CCCGGAGAAA ATCGTGCGCA GAGTCCAGGA AGTGTCTGCG    10920
GTGCTCTATC ATCTGGAGCA GATGGAGCAC CCTTACAAGT CCAAGAAGGC CGTGTGGCAC    10980
AAGCTCTTGT CTAAGCAGCG CCGGAGGGCC GTGGTCGCCT GTTTCCGTAT GACCCCGCTG    11040
TACAACCTGC CCACGCACCG GGCCTGTAAT ATGTTCCTGG AAAGCTACAA GGCTGCGTGG    11100
ATCCTGACCG AAGACCACAG TTTTGAGGAC CGCATGATAG ATGACCTTTC AAAAGCTGGT    11160
GAGCAGGAGG AGGAGGAGGA AGAGGTGGAG GAGAAGAAGC GGACCCCCT GCACCAGCTC    11220
GTCCTGCACT TCAGCCGCAC CGCCCTGACC GAAAAGAGCA AACTGGATGA AGATTACTTA    11280
TATATGGCGT ATGCTGACAT CATGGCAAAG AGCTGCCACC TGGAGGAGGG AGGGGAGAAC    11340
GGCGAAGCTC AAGAAGAGGT TGAGGTTTCC TTTGAGGAGA AGGAGATGGA GAAGCAGAGG    11400
CTCCTGTACC AGCAGGCACG GCTGCACAAC CGTGGGGCCG CGGAGATGGT GCTGCAGATG    11460
```

```
ATCAGTGCCT GCAAAGGAGA GACAGGCGCC ATGGTATCGT CCACCCTGAA GCTGGGCATC    11520
TCCATCCTGA ACGGAGGCAA TGCCGATGTG CAGCAGAAAA TGCTGGATTA CCTGAAGGAC    11580
AAGAAGGAAG TTGGCTTCTT CCAGAGTATC CAGGCACTGA TGCAAACCTG CAGCGTCCTG    11640
GATCTCAATG CCTTTGAGAG ACAGAACAAG GCAGAGGGGC TGGGCATGGT GAACGAGGAC    11700
GGAACCGTCA TCAACCGCCA GAACGGAGAG AAGGTCATGG CAGATGATGA ATTCACCCAA    11760
GACCTGTTCC GATTCCTGCA ATTGCTCTGC GAGGGCCACA ATAATGATTT CCAAAACTAC    11820
CTACGGACAC AGACAGGGAA CACAACCACT ATTAACATCA TCATCTGTAC TGTGGACTAC    11880
CTCCTGCGGC TGCAGGAGTC CATCAGTGAT TTCTACTGGT ACTACTCCGG CAAGGATGTC    11940
ATTGAGGAGC AGGGCAAGAG AAACTTTTCC AAGGCCATGT CGGTGGCTAA ACAGGTGTTC    12000
AATAGCCTCA CAGAATACAT CCAGGGTCCC TGCACCGGGA ACCAGCAGAG CCTAGCGCAC    12060
AGTCGCCTCT GGGACGCCGT GGTGGGATTC CTGCACGTGT TCGCCCACAT GATGATGAAG    12120
CTCGCTCAGG ACTCGAGCCA GATCGAGCTG TTGAAGGAGC TGCTGGATCT ACAGAAGGAC    12180
ATGGTGGTGA TGTTGCTGTC GCTACTAGAA GGGAACGTGG TGAACGGCAT GATTGCCCGG    12240
CAGATGGTGG ACATGCTTGT GGAGTCCTCG TCCAACGTGG AGATGATCCT CAAGTTCTTC    12300
GACATGTTCC TGAAACTCAA GGACATCGTG GCTCTGAGG CCTTCCAGGA CTATGTCACT    12360
GACCCCCGGG GTCTCATCTC CAAGAAGGAC TTCCAGAAGG CCATGGACAG CCAGAAGCAG    12420
TTCACCGGTC CGGAAATCCA GTTCCTGCTT TCGTGCTCTG AAGCGGATGA GAACGAGATG    12480
ATCGACTGCG AGGAGTTCGC CAACCGCTTC CAGGAGCCAG CCCGTGACAT TGGCTTCAAC    12540
GTAGCTGTGC TGCTGACCAA CTTGTCGGAG CACGTGCCGC ACGACCCGCG CCTGCGCAAC    12600
TTCCTCGAGC TGGCGGAGAA CATCCTCGAG TACTTCCGGC CCTACCTGGG CCGCATCGAG    12660
ATCATGGGCG CCTCGGGCCG CATCGAGCGT ATCTACTTTG AGATATCGGA GACCAACCGC    12720
GCCCAGTGGG AGATGCCCCA GGTGAAGGAG TCGAAGCGTC AGTTCATCTT CGACGTGGTG    12780
AACGAGGGTG CGAGTCGGA GAAGATGGAG CTCTTCGTGA GCTTCTGCGA GGACACCATC    12840
TTCGAGATGC AGATCGCTGC ACAGATCTCG GAGCCCGAGG GCGAGCCGGA GGAGGATGAG    12900
GACGAGGGCG CGGGCCTGGC GGAGGCGGGC GCTGAGGGCG CGGAGGAGGG CGCGGTGGGG    12960
CCCGAGGGCG CGGCGGGGAC CGCGGCGGCC GGCTTGACGG CGCGGCTGGC AGCGGCCACG    13020
AGCCGGGCTC TGCGCGGCCT CAGCTACCGC AGCCTGCGGC GGCGCGTGCG GCGGCTGCGG    13080
CGGCTCACAG CGCGGGAGGC GGCCACGGCG CTGGCCGCGC TGCTCTGGGC GGCGCTGGCG    13140
CACGCGGGGG CGGCGGGCGC CGGGGCGGCG GCAGGCGCGC TGCGCCTGCT CTGGGGCTCG    13200
CTCTTTGGTG GCGGCCTGGT GGAGGGTGCC AAGAAGGTGA CGGTGACCGA GCTCCTGGCG    13260
GGCATGCCCG ATCCCACGGG CGACGAGGTG CACGGCGAGC AGCCGGCTGG GCCCGGCGGC    13320
GAGGCGGACG GCGAGGGCGC GGGCGAGGGC GCGGGCGAAG CCCTGGAGGG CGCGGGCGAC    13380
GAGGAGGTGG CGGTGCAGGA GGCCGGCCCG GGAGGCGCAG ACGGGCTGT GGCCGTGGCC    13440
GAAGGGGGCC CCTTCCGGCC CGAAGGGGCT GGCGGCCTCG GGACATGGG TGACACGACG    13500
CCTGCGGAGC CGCCCACGCC CGAGGGCTCC CCTATCATCA AGAGGAAGCT GGGGGTGGAT    13560
GGAGAGGAAG AGGAGCTGCC GCCGGAGCCG GAACCGGAGC CGGAGCCAGA GCCTGAGAAA    13620
GCTGATGCTG AGAATGGGGA GAAGGAAGAA GTCCCCAAGC CCCACCAGA GCCCCCAAG    13680
AAGACAGCTC CTCCTCCACC CCCTCCAAAG AAGGAGGAGG GTGGAAGCGG GGGCCTGGAA    13740
TTCTGGGGAG AACTGGAAGT ACAGAGGGTG AAGTTCTTGA ACTACCTCTC CCGGAACTTT    13800
TACACTCTGC GATTCCTTGC CCTCTTCTTG GCATTTGCCA TCAACTTCAT CTTGCTGTTT    13860
TATAAGGTCT CGGACTCTCC ACCAGGGGAG GATGACATGG AGGGCTCAGC AGCCGGGGAC    13920
```

| | | | | | |
|---|---|---|---|---|---|
| CTGTCAGGTG | CAGGCTCTGG | TGGCGGCTCT | GGTTGGGGCT | CCGGGGCCGG | AGAGGAGGTG | 13980 |
| GAAGGCGACG | AGGACGAGAA | CATGGTATAC | TACTTCCTGG | AGGAGAGCAC | GGGCTACATG | 14040 |
| GAGCCCGCCT | TGCGCTGCCT | GAGCCTGCTG | CACACGCTGG | TGGCCTTTCT | CTGCATCATA | 14100 |
| GGCTACAACT | GCCTCAAGGT | GCCCCTGGTG | ATCTTTAAGC | GGGAGAAGGA | ACTGGCCCGG | 14160 |
| AAACTGGAGT | TTGACGGCCT | CTACATCACG | GAGCAGCCCG | AGGATGATGA | CGTGAAGGGG | 14220 |
| CAGTGGGACC | GGCTGGTGCT | CAACACACCG | TCTTTCCCCA | GCAACTACTG | GACAAGTTT | 14280 |
| GTCAAGCGGA | AGGTCCTGGA | CAAGCACGGG | GACATCTACG | GGCGGGAGCG | GATCGCCGAG | 14340 |
| CTGCTGGGTA | TGGATCTGGC | CACGCTGGAG | ATCACAGCCC | ACAACGAGCG | CAAGCCTGAA | 14400 |
| CCACCGCCAG | GGCTGCTCAC | CTGGCTCATG | TCCATCGATG | TCAAGTACCA | GATCTGGAAG | 14460 |
| TTTGGGGTCA | TCTTCACAGA | CAACTCGTTC | CTGTACCTGG | GCTGGTACAT | GGTGATGTCC | 14520 |
| CTCCTGGGTC | ACTACAACAA | CTTCTTCTTC | GCTGCCCACC | TCCTGGACAT | TGCCATGGGG | 14580 |
| GTCAAGACGC | TGCGTACCAT | CCTCTCGTCC | GTCACCCACA | ATGGCAAACA | GCTGGTGATG | 14640 |
| ACCGTGGGCC | TCCTGGCGGT | TGTGGTCTAC | CTGTACACCG | TGGTGGCCTT | CAACTTCTTC | 14700 |
| CGCAAGTTCT | ACAACAAGAG | CGAGGACGAG | GACGAGCCTG | ACATGAAGTG | TGATGACATG | 14760 |
| ATGACGTGTT | ACCTGTTTCA | CATGTATGTG | GGTGTCCGCG | CTGGTGGGGG | CATTGGGGAC | 14820 |
| GAGATCGAGG | ACCCAGCAGG | AGATGAATAT | GAGCTCTACC | GGGTGGTCTT | TGACATCACC | 14880 |
| TTCTTCTTCT | TCGTCATCGT | CATCCTGTTG | GCCATCATCC | AGGGTCTGAT | CATTGATGCT | 14940 |
| TTTGGCGAGC | TCCGAGACCA | ACAAGAGCAA | GTGAGAGAAG | ATATGGAGAC | CAAGTGCTTC | 15000 |
| ATCTGTGGCA | TCGGCAGCGA | TTACTTTGAT | ACGACACCAC | ACGGGTTCGA | GACCCACACG | 15060 |
| CTAGAGGAGC | ACAACCTGGC | CAATTACATG | TTTTTCCTGA | TGTATCTGAT | AAACAAGGAC | 15120 |
| GAGACAGAAC | ACACGGGTCA | GGAGTCTTAT | GTCTGGAAGA | TGTACCAAGA | GAGATGCTGG | 15180 |
| GATTTCTTCC | CGGCTGGCGA | TTGTTTCCGC | AAGCAGTATG | AGGACCAGCT | TAGCTGAGAC | 15240 |
| ACCCCAGCT | GGCCCCGCAC | CCCCACCTCA | AGTGCCTTGT | TTTCACAGCA | AGCCCCTTAG | 15300 |
| CCCCCCAAAC | CCTCCCCCCA | AGGCAGCTAG | GGAGAGGTG | ACCATGCAGT | GGAGAAATAA | 15360 |
| AGTCTGTGCT | ACACCCCT | | | | | 15378 |

( 2 ) INFORMATION FOR SEQ ID NO:2:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Pig RYR1 Gene ( v i i i ) POSITION IN GENOME:
        ( C ) UNITS: bp ( x i ) SEQUENCE DESCRIPTION: SEQ ID NO:2:

| | | | | | |
|---|---|---|---|---|---|
| GTTCCCTGTG | TGTGTGCAAT | GGTGTGGCCG | TGCGCTCCAA | CCAAGATCTC | ATTACTGAGA | 60 |
| ACTTGCTGCC | TGGC | | | | | 74 |

( 2 ) INFORMATION FOR SEQ ID NO:3:

( i ) SEQUENCE CHARACTERISTICS:

(A) LENGTH: 1598 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vii) IMMEDIATE SOURCE:
  (B) CLONE: Pig RYR1 gene (viii) POSITION IN GENOME:
  (C) UNITS: bp (xi) SEQUENCE DESCRIPTION: SEQ ID NO:3:

```
GACAAGCATG GGAGGAACCA CAAGGTGGGC CTCTCATCCC CTCAATTCTG CACTTGATCT    60
TTCCCCACCC CCCCTCTTCA CTCTTACCTG GACTCCTCTG CCACATGCTT CTAGCTCAAT   120
ACAAAGGTCT CAAACTCCTT GTTTTTGTTT TTGTTTTTAT GGCTGAACCT GTGGCAAATG   180
GAAGTTTCCA GGCAAGGGGG TGAACCAGAG CTATAGCTGC TGGCCTACAC CACAGCCTCA   240
TCAACAACGC CAGATCGAG  CCGTGTCTGC CACCTACACC ACAGCTCATG GCAATACCAG   300
ATCCTTAACC CACTGAGCGA GGCCAGGGAT CGAACCTGCA ACCTCACGAA TACTAGTTGG   360
GTTTGTAACC CACTGAAGCC ACAATGGGAA CTCCTCAAAG TCATTCTTAA ATGGATTCTG   420
GGCCCCCGAT ATGCTTTCTT AGATCTTTGA AGTGTTTTCT AAATGTCTAA TGTAAATGCA   480
GGCGGCTGCA TATACACGCT CCAGTTTGCC ACAGGTCCTA CCAGTCCCGA CTGAATTAAT   540
TATTTCTAAC CACCTCATGT ATGGACAACA TCCACCTGGC CCCGAAGATG CACGTTGGTG   600
ACCCCGCCC  ATCCAGAACC TCGTCTTGGT CTCCGTGCTC TCGCACTGAC CCGGCCTTTC   660
ACTCTTGCCT CCGACTTCTC ACCCCTTGCT CCCGTCTCTC CTTTCCTCCT CTGCTGATGC   720
CCGATCCCAT CCCTCACAGC CCCCTGCGTC TCACCAGACC TTTCTCTTTG ACCTTGATCT   780
CCCTGTGTCA TCCCTGACCT TCCCGCTTTC ACCACCTCTT CTCAGTCACA TCCCCACCTC   840
CCACCCTGGG ACATCATCCT TCTGGCTTCC CACCCTGGGT CTTCCATGGA CCACACCCTC   900
CCCGCAAGTG CCCTCACACC TTGACCTCTG ACCTTGACCC CTAGGTGCTG GATGTCCTGT   960
GTTCCCTGTG TGTGTGCAAT GGTGTGGCCG TGCGCTCCAA CCAAGATCTC ATTACTGAGA  1020
ACTTGCTCCC TGGCCGCGAG CTTCTGCTGC AGACAAACCT CATCAACTAT GTCACCAGGT  1080
CTGGCCCCCC AACCTTTGAC CCCAGAGCTA GAACCCTCCA CCACCCCGCC CCGACTCAGA  1140
GACTCCACTC CGGTGAATGG CCCTTCCTCC GTCCCCACC  CCCGGACTTA ATGCCAGTCC  1200
CCACCCCTGT CGTGCTTGTC CCAGCTTGTC CCTGGCTTCT TACTTCTCTT ACCCTTCTTC  1260
CCCAAACTCT TTCTCCCTCT GTCTCTTCCT CTTTCTCTCT TTCTGTGTTT GCTCTCTTTG  1320
TCTGTCTATC TATTTCTCCT CCATCTCTTT TTCCAGGTCT TTCTCTCATC TCTCTTCTCT  1380
GTCTTTTGAC GTCTCTCTGT CTGTCTCTGC CTCTGCTTTC TCTCTCTGTG TCTCTGTCTC  1440
CATGGCTCTG CCTTTCCGTT TTTCCTGCGT ATGTGTCTCT TTGTCTTTTT CCCTCTCCCC  1500
CCCAGCCTTC CCTCCAGCCT GGCTCTCTTC TCCAGCCCTC CTCATCCTCC TCTTCTGTCC  1560
CATTTCTCCT GCAGCATCCG CCCCAACATC TTTGTGGG                          1598
```

DIAGNOSIS FOR PORCINE MALIGNANT HYPERTHERMIA

FIELD OF THE INVENTION

This invention relates to the animal disease malignant hyperthermia (MH), to the cloning and characterization of a gene associated with MH in swine, and to the development of DNA and antibody-based methods for detecting individual pigs susceptible to MH.

BACKGROUND OF THE INVENTION

Malignant hyperthermia (MH) is a hypermetabolic myopathy which is triggered in genetically-susceptible human and animal individuals by potent, volatile anesthetics such as halothane [Denborough and Lovell (1960) Lancet 2, 545: Harrison et al. (1968) Brit. Med. J. 3:594–595] or by depolarizing muscle relaxants such as succinycholine [Harrison et al. (1969) Brit. J. Anaesthesia 41:844–855]. In swine, it is also referred to as porcine stress syndrome [Topel (1968) Mod. Vet. Pract. 49:40–41; 59–60] because it may be triggered by exertional [Ludvigsen (1953) Internat. Vet. Congr. Stockholm 1:602–606] thermal [Forrest et al. (1968) J. of Appl. Physiol. 24:33–39], anoxic [Lister et al. (1970) Am. J. Physiol. 218:102–107], or mechanical [Gronert (1980) Anaesthesiol. 44:36–43] stressors as well as anesthesia [Hall et al (1966) Brit. Med. J. 4:1305]. A similar stress syndrome may occur in MH-susceptible (MHS) humans [Wingard (1974) Lancet 2;1450–1451] and dogs [O'Brien et al. (1983) Can. Vet. J. 24:172–177]. MH is characterized by the peracute development of contracture and maximal rate of metabolism in muscle. These have been proposed to occur due to an uncontrollable and sustained elevation of myoplasmic calcium [Britt and Kalow (1970) Can. Anesthetists Soc. J. 17:316–330: Lopez et al. (1985) Biophys. J. 47:313a], which is known to activate the contractile apparatus and metabolic machinery of skeletal muscle [Martonosi (1984) Physiol. Rev. 64:1240–1319).

The hyperactivity of muscle which occurs during MH results in the depletion of ATP and glycogen stores and the excessive formation of carbon dioxide, lactic acid and heat. This thermogenesis, in conjunction with peripheral vasoconstriction, leads to hyperthermia. The rapid rate of aerobic metabolism, by depleting blood oxygen, causes cyanosis [Gronert (1980) Anaesthesiol. 53:395–423]. During MH, glycogenolysis, rhabdomyolysis and acidemia cause the release of large amounts of potassium from muscle and liver [Hall et al. (1980) Brit. J. Anaesthesiol. 52:11–17 ] into the vascular compartment. The resultant hyperkalemia contributes to the development of cardiac dysrhythmia and subsequent heart failure [Britt (1983) in "Complications in Anesthesiology" F. K. Orkin and L. H. Cooperman (eds) Lippincott, pp. 290–313].

Major revenue loss in the swine, pork and bacon industries occurs because of stress-induced MH deaths, usually during transport to the slaughterhouse. This occurs in homozygotes which make up 1 to 2% of swine and is referred to as porcine stress syndrome (PSS). Greater loss occurs due to the development of inferior quality meat after slaughter of MHS homozygote or heterozygote swine, which make up 10 to 30% of the population.

Activities and environmental stressors, which may trigger MH, include transport, restraint, mating, farrowing, fighting, vigorous exercising, and hot, humid weather [Mitchell and Heffron (1982) Adv. Food Res. 28:167–230]. The neural stimulation of muscle which occurs during slaughter [McLoughlin (1971) in "Condition and Meat Quality of Pigs" G. R. Hersel-de-heer et al (eds) Pudoc, pp 123–132], and the anoxia [Lister et al (1970) Am. J. Physiol. 215:102–107] which occurs with cardiac failure, are sufficient to trigger hypermetabolism in muscle.

As a result of the excessive rates of production of lactic acid and heat [Lawrie (1960) J. Comp. Pathol. 70:273–295], sarcoplasmic proteins denature, thereby causing a deterioration of the water-binding capacity of muscle. Furthermore, the increased osmotic activity due to end-products of hypermetabolism causes an influx of water from the extracellular space, thereby resulting in hemoconcentration and increased intramyofiber water content [Berman et al (1970) Nature 220:653–655]. The muscle becomes pale, soft and exudative, sour-smelling and loose-textured [Briskey (1964) Adv. in Food Res. 13:89–178]. The shrinkage due to water loss during storage, transport and processing of the carcass is the major cause of wholesale losses at pork packing plants [Smith and Lesser (1982) Anim. Prod. 34:291–299]. Shorter shelf-life and decreased organoleptic acceptability contribute to retail losses. Other causes of lost revenue with MHS swine are their decreased average daily weight gain, conception rates, litter sizes and boar breeding performance [Webb (1980) Vet Record 106:410–412; Carden et al (1985) Anim. Prod. 40:351–358.

In 1972, revenue loss in the United States due to porcine MH was estimated to be at least a quarter of a billion dollars annually [Hall (1972) Proc. of Pork Quality Symp. (R. G. Cassens et al eds) pp. ix–xii]. Since the late 1960s and the mid 1970s, the incidence of MH in North American swine populations is reported to have decreased approximately twofold [Grandin (1980) Internat. J. Studies in Anim. Product 1:313–317). This decrease occurred as pig producers and meat packers modified their swine breeding programs and swine- and pork-management practices in order to decrease the incidence of MH. This was achieved by reducing the use of heavily muscled swine as breeding stock, reducing pre-slaughter stress on market hogs and increasing carcass chilling rates [Topel (1981) Proc. Work Planning Meeting of FSE/DSD, Ottawa, Agric. Can. 1–12].

Occurrence of MH is sporadic in all animal species except for swine, where, because of an association with heavy muscling, the disease has become endemic and in some countries has reached epidemic proportions [Webb (1980) Vet. Record 106:410–412; Mitchell and Heffron (1982) Ad. Food Res. 18:167–230]. In swine, the incidence of MH-susceptibility is breed and strain-dependent, ranging from less than 1% to greater than 90% of the herd. Increased prevalence of this disease, especially in European countries, is postulated to be a reflection of genetic improvement programs based entirely on performance and production parameters such as depth of back fat, muscularity, and carcass yields.

For Dutch and German strains of Pietrain and Poland China, and German and Belgium strains of Landrace swine. 68 to 94% of individuals were found to be MHS homozygotes and heterozygotes. By contrast, less than 10% of swine in North American herds are found to have susceptibility to MH. Because these figures are based on a diagnostic test (halothane challenge test) with poor sensitivity, they underestimate the incidence of pale, soft and exudative pork [Webb (1980;1981) supra]. Furthermore, swine and carcass management practices at slaughter affect the incidence and degree of pale, soft, exudative pork from MHS swine [Topel (1981) supra]. On the other hand, these figures overestimate the occurrence (less than 1% in North America) of stress-induced MH-deaths, which may be largely eliminated by 'stress-free' management practices [Topel (1981) supra].

In Canadian swine, the prevalence of MH gene homozygosity is up to 6% for Canadian Landrace and 1% for Yorkshire swine [D'allaire et al (1982) Can. Vet. J. 23 168), the most important breeds. Based on recent data indicating that 1.9% of Ontario swine are homozygous for MH and a Mendelian inheritance pattern, the prevalence of heterozygotes would be 24%. Administration of succinycholine in the halothane challenge test detects many heterozygotes.

The high fatality rate of MH, the recognition of its heritability, and its association with inferior quality pork, have prompted the development of diagnostic tests for susceptibility to MH in swine. Halothane challenge testing is used extensively in the swine industry to detect susceptibility. Major limitations of this test, however, include its low sensitivity [Nelson et al. (1983) J. Anesthesia Analgesia 62:545-552; Seeler et al (1983) supra; Webb et al. (1986) Anim. Prod. 42:275-279] and the high number of fatalities which may occur. In a typical test, two to three month old pigs are physically restrained and forced to inhale 3 to 5% halothane in oxygen through a face mask for several minutes. Those developing extensor muscle rigidity during the test are diagnosed as MHS. While the onset of MH signs is delayed by prior tranquillization [McGrath et al. (1981) Am. J. Vet. Res. 42:195-198], thermal, exertional, pharmacological, or psychological stresses will speed its onset [Van den Hende et al. (1976) Brit. J. Anaesthesia 48:821-829; Seeler et al. (1983) supra].

The caffeine [Kalow et al. (1970) supra] and halothane [Ellis et al (19-1) Brit. J. Anaesthesia 43:721-722] contracture tests are considered to be the most definitive preanesthetic diagnostic tests for MH-susceptibility [European Malignant Hyperpyrexia Group, 1984, Brit. J. Anaesthesia 57:983-990]. They are used extensively in man and have been applied successfully in swine [Gronert (1979) Anaesthesia Analgesia 58:367-371], horses [Waldron-Mease and Rosenberg (1979) Vet. Res. Commun. 3:45-50] and dogs [O'Brien et al. (1983) supra].

In veterinary medicine, contracture tests are seldom used because of cost, the trauma involved and the need for appropriate equipment and expertise. In these tests. muscle is excised, placed in oxygenated physiological saline, and connected to a force-displacement strain gauge. Isometric tension of the muscle is transduced into an electronic signal and recorded by a polygraph. To demonstrate its viability, the muscle is made to twitch continuously by applying electrical stimuli. Caffeine or halothane is then added to the bathing solution in increasing amounts. Muscle from MHS individuals is hypersensitive to the contracture-producing effects of these drugs. They increase the baseline tension of MHS muscle more, and at a lower concentration, than occurs for normal muscle [Britt, 1979, Int. Anaesthesia Clin. 17:63-96].

Diagnosis of MH-susceptibility may be facilitated by various indirect blood tests for MH, such as:

(1) haplotyping swine for the MH-gene-linked marker loci for H [Rasmusen and Christian (1976) Science 191:947-948) and S (Rasmusen (1981) *Anim. Bood Groups in Biochem. Genet.* 12:207-209] blood groups, erthyrocyte pnosphohexose isomerase and 6-phosphogluconate dehydrogenase [Jorgensen et al. (1976) *Acta Vet. Scand.* 17:370-372], and serum protein postalbumin-2 [Juneja et al. (1983) *Anim. Blood Groups in Biochem. Genet* 14:27-367;

(2) erythrocyte osmotic fragility tests [King et al 1976, *Ann. Genet. Select. Anim.* 48:537-540];

(3) hyperlactatemia and homoconcentration following intravenous injection of low dosages of halothane [Gregory and Wilkins (1984) *I. Sci. Food Agric.* 35:147-153];

(4) post-exertional alterations in blood parameters, such as hyperlactatemia, homoconcentration, or elevated catecholamines [Ayling et al. (1985) *Brit. J. Anaesthesia* 57:983-990; D'Allaire and DeRoth (1986) *Can J. Vet. Res.* 50:78-83; Rand and O'Brien (1986) *Am. J. Vet. Res.* 190:1013-1014];

(5) enzymatic [Schanus et al. (1981) *Prog. Clin. Biol. Res.* 55, 323-336] and thermochemiluminescent [Kiel and Erwin (1984) *Anal. Biochem.* 143:231-236) assays for antioxidant system deficiency;

(6) electron microscopic detection of hypertrophied open canalicular systems and energy dispersive microanalytic detection of decreased surface membrane calcium in platelets [Basrur et al. (1983) *Scanning Elect. Microsc.* 5:209-214];

(7) abnormal halothane-induced purine nucleotide profiles of platelet-rich plasma [Solomons and Masson (1984) *Acta. Anaesth. Scand.* 27:349-355];

(8) abnormal halothane-induced increase in cytosolic calcium of isolated lymphocytes [Klip et al. (1986) *Biochem Cell Biol.* 64:1181-1189].

These tests lack sensitivity, specificity, reproducibility and/or have not been widely evaluated [Britt (1985) supra; Lee et al (1985) *Anaesthesiol.* 63:311-315; O'Brien et al. (1985) *Am. J. Vet. Res.* 46:1451-1456; Webb (1981) supra].

Tests which assay for the hypermetabolic and/or degenerative changes occurring in 'triggered' MH muscle include tests for ATP-depletion using in vitro biochemical assays [Harrison et al. (1969) *Brit. J Anaesthesia* 41:844-845] or in vivo 31-phosphorus nuclear magnetic resonance spectroscopy [Roberts et al. (1983) *Anaesthesiol.* 59:A230]; increased calcium efflux from isolated mitochondria [Cheah and Cheah (1981) *Biochim. Biophys. Acta* 634:40-49]; increased oxygen consumption and muscle twitch response following local ischemia [Jones et al. (1981) *Anesthesia Analgesia* 60:256-257 ] or decreased calcium uptake by histologic sections [Allen et al. (1980) Anesthesiol. 53:S251] or isolated sarcoplasmic reticulum [O'Brien (1986) *Can. J. Vet Res.* 50:329-337]. These tests have not been standardized nor widely evaluated. Furthermore, they may not be specific since they are indirect, measuring changes occurring secondarily to the underlying molecular defect.

A calcium-release sensitivity test performed on isolated muscle sarcoplasmic reticulum [O'Brien (1986) *Can. J. Vet. Res.* 50:318-329] is apparently a biochemical correlate of the physiological caffeine and halothane contracture tests, although it may be one to two orders of magnitude more sensitive.

Recently direct analysis of the Ca$^{2+}$ release channel protein has revealed differences that may correlate directly with the disease:

(1) the Ca$^{2+}$ release channel of the sarcoplasmic reticulum (ryanodine receptor) from MHS pigs has a higher affinity for ryanodine binding and requires higher concentration of calcium to inhibit ryanodine binding [Mickelson et al (1988) *J. Biol. Chem.* 263:9310–9315]

(2) patterns of tryptic digestion of the ryanodine receptor, as analyzed with a specific antibody, are altered in MHS swine [Knudson et al (1990) *J. Biol. Chem.* 265:2421–2424];

(3) in single channel recordings, MHN Ca$^{2+}$ release channels were inactivated by pCa less than 4whereas MHS channels remained open for significantly longer times, demonstrating an altered Ca$^{2+}$ release channel inactivation [Fell et al (1990) *Biophys J.* 50:471–475]

Calcium-release sensitivity tests and tests of the structure and function of the ryanodine receptor have not yet been used for medical or commercial purposes.

The calcium release channel of the sarcoplasmic reticulum (ryanodine receptor) is a large protein that spans the gap between the transverse tubule and the sarcoplasmic reticulum. The channel is activated by ATP, calcium, caffeine, and micro-molar ryanodine and inhibited by ruthenium red, tetracaine, calmodulin, high Mg$^{2+}$ and ryanodine (hence the name "ryanodine receptor") [Lai et al. (1988) *Nature* 331:315–319].

DNA encoding the human and rabbit skeletal muscle ryanodine receptors (RYR1) [Zorzato et al. (1990) *J. Biol. Chem.* 265:2244–2256] and the cardiac muscle ryanodine receptor (RYR2) [Otsu et al (1990) *J. Biol. Chem.* 265:13472–13483] has been cloned and sequenced. The deduced amino acid sequences of the RYR1 gene product comprise 5032 amino acids. The predicted protein structure suggests that the calcium release channel contains up to 12 transmembrane domains lying in the C-terminal portion of the molecule. The remainder of the protein is predicted to constitute the "foot" portion which spans the gap between the transverse tubule and the sarcoplasmic reticulum. Potential binding sites for calcium, calmodulin, ATP and other modulators of calcium channel function are also believed to be present in both RYR1 and RYR2 molecules between residues 2600 and 3000. Genetic linkage between the ryanodine receptor (RYR1) and MH genes has been determined in humans [MacLennan et al. (1990) *Nature* 343:359–361]. These observations strongly support the view that the ryanodine receptor is involved in malignant hyperthermia and that a defect in the calcium release channel might be the basic defect in animals, including humans, with MH.

The gene responsible for halothane sensitivity (HAL) has been found to segregate in pigs with a number of other genetic markers including S (S locus affecting expression of A-0 red blood antigens), Phi (glucose phosphate isomerase), H (H locus encoding blood group antigens), Po2 (postalbumin-2) and PgD (6-phosphogluconate dehydrogenase) [Rasmussen and Christian (1976) supra; Rasmussen (1981) supraJorgensen et al (1976) supra; Juneja et al (1983) supra]. It is, therefore, assumed that these genes are linked on pig chromosome 6p11-q21 [Horbitz et al. (1990) *Genomics* 8:243–248]. The human RYR1 gene has been localized to chromosome 19q13.1 and shown to be syntenic with these same genes [MacKenzie et al. (1990) *Am. J. Hum. Genet.* 46:1082–1089]. Linkage between the human RYR1 gone on chromosome lgq13.1 and the MH gene has been established in humans [MacLennan et al. (1990) supra].

We have discovered that the ryanodine receptor gene is the gene that is defective in porcine MH. This invention relates to the isolation and sequence analyses of cDNAs encoding normal and mutant porcine skeletal muscle sarcoplasmic reticulum calcium release channel proteins (alternatively referred to as ryanodine receptors) and determination that a mutation in the RYR1 gene in MHS strains segregates with the MH phenotype in pigs, such as Yorkshire. Pietrain, Landrace and Duroc strains and, predictably in all other heavily muscled strains (e.g. Poland China; hampshire). The discovery that the porcine RYR1 gene is the gene responsible for MH and the discovery of diagnostic DNA probes from the porcine RYR1 gene forms the basis, according to an aspect of the invention, for a definitive DNA and/or antibody-based diagnostic test for MH.

SUMMARY OF THE INVENTION

According to an aspect of the invention, substantially purified DNA sequence encoding porcine RYR1 and its normal and mutant functional equivalents characterized by:

i) the cDNAs encoding a protein having 5035 amino acids and a molecular weight of approximately 564,000 daltons;

ii) the DNA having a length of approximately 15.3 kb; and iii) isolated from chromosome 6 of pigs.

According to another aspect of the invention, substantially purified normal and mutant porcine cDNAs have the sequences encoding the amino acid positions 1 to 5035 of FIG. 2.

According to another aspect of the invention, DNA probes include fragments of the DNA encoding the normal and mutant porcine ryanodine receptor protein.

According to a further aspect of the invention the use of the DNA probes in mutational analysis determines if a porcine subject is homozygous or heterozygous for susceptibility to malignant hyperthermia.

According to another aspect of the invention, the use of the DNA probes in a one-step PCR-based diagnosis of MHS mutation in pig genomic DNA is provided.

According to another aspect of the invention, at least seventeen polymorphisms exist in normal and mutant porcine cDNAs as presented in FIG. 2, such polymorphisms being useful in genetic analysis involving the ryanodine receptor.

According to another aspect of the invention, substantially purified normal and mutant porcine ryanodine receptor proteins are free of any foreign porcine protein. The proteins have molecular weights of approximately 564,000 daltons and amino acid sequences as presented in FIG. 2.

According to another aspect of the invention, substantially purified antibodies specific to protein sequences of the pig ryanodine receptor protein are disclosed. The antibodies may be either polyclonal antibodies or monoclonal antibodies. Such antibodies are useful in immunological assays to determine if a pig is susceptible to malignant hyperthermia.

BRIEF DESCRIPTION OF THE DRAWINGS

Aspects of the invention are demonstrated and described with respect to the drawings wherein:

Figure 2A:
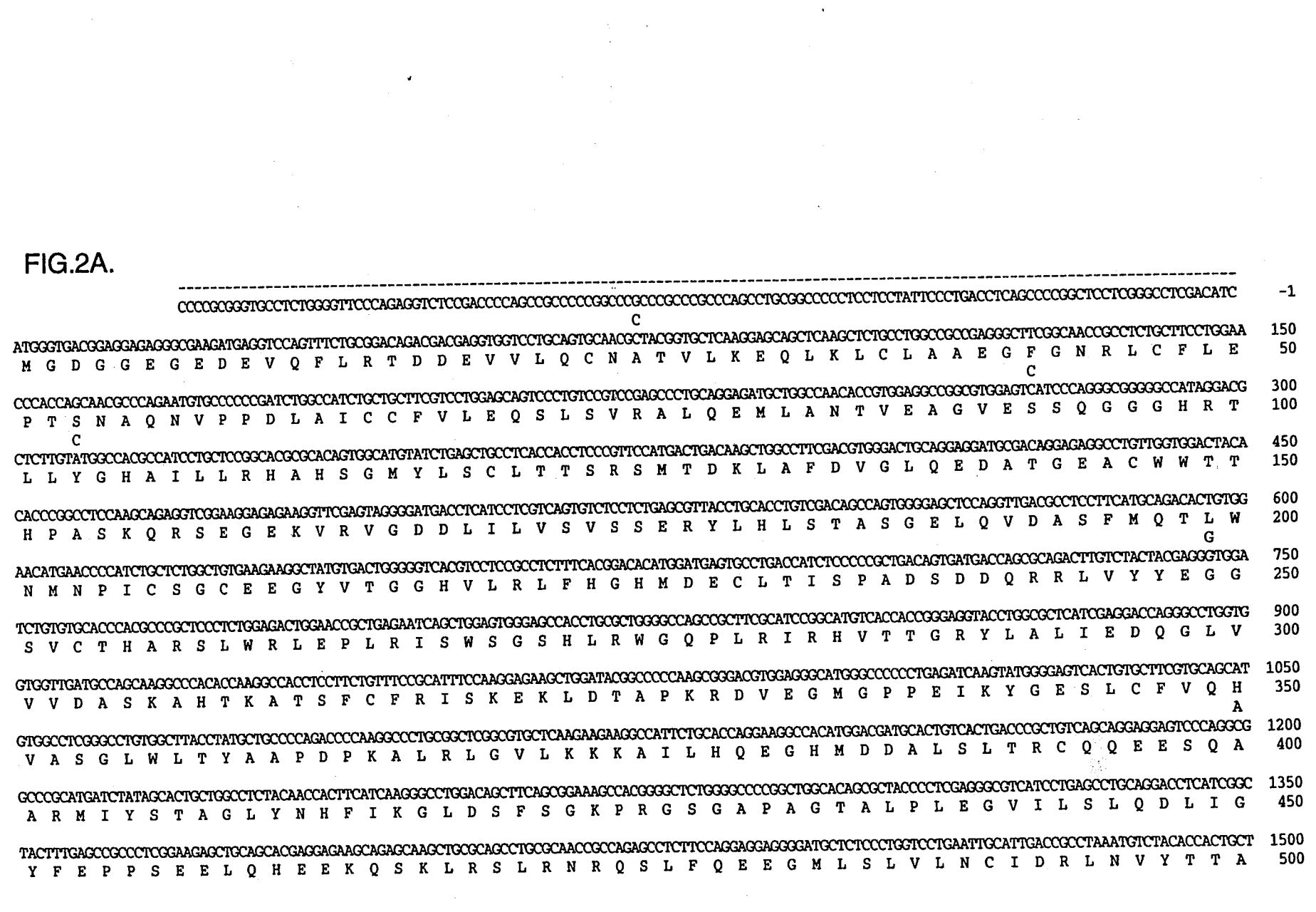
Figure 2B:
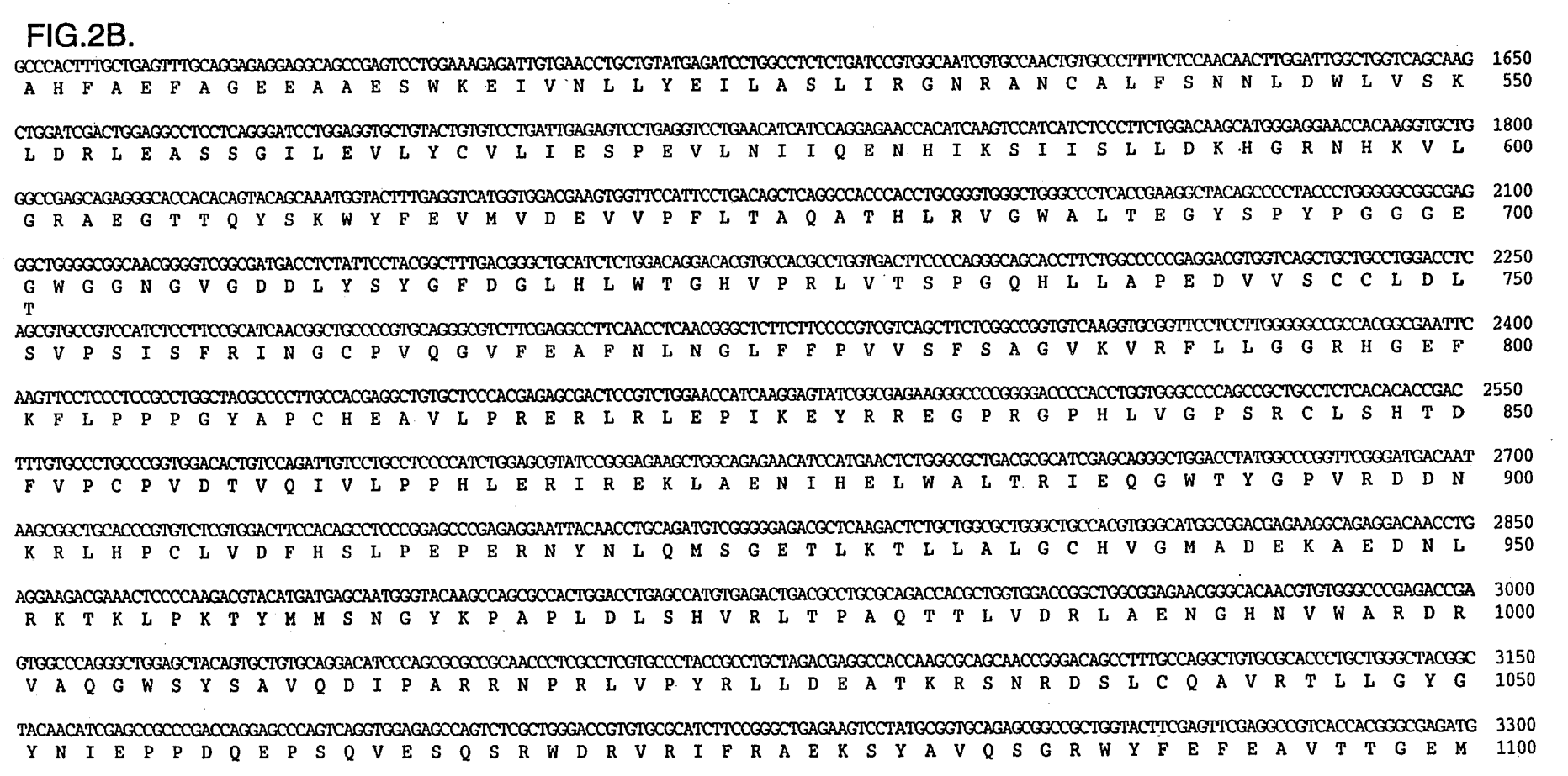
Figure 2C:
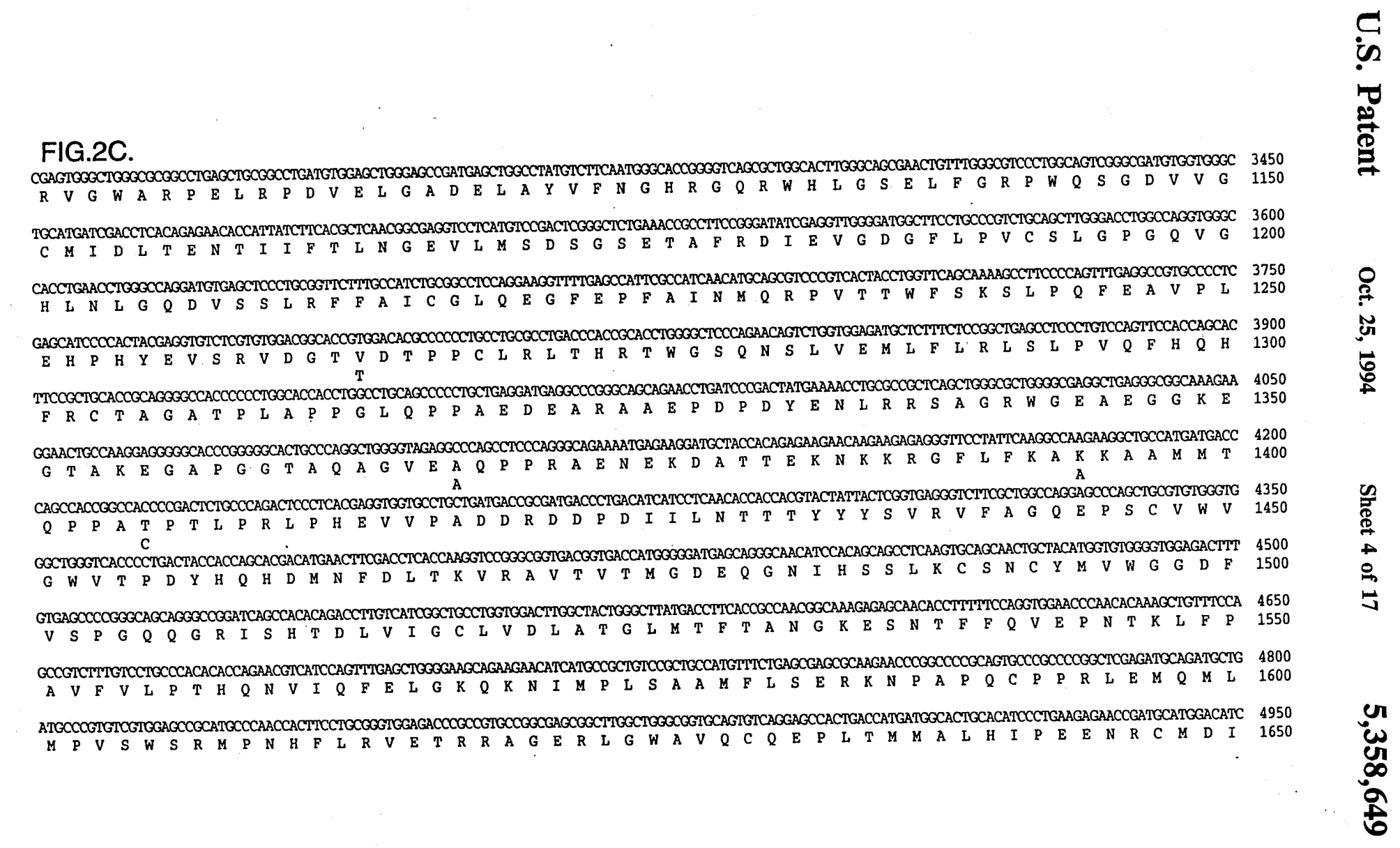
Figure 2D:
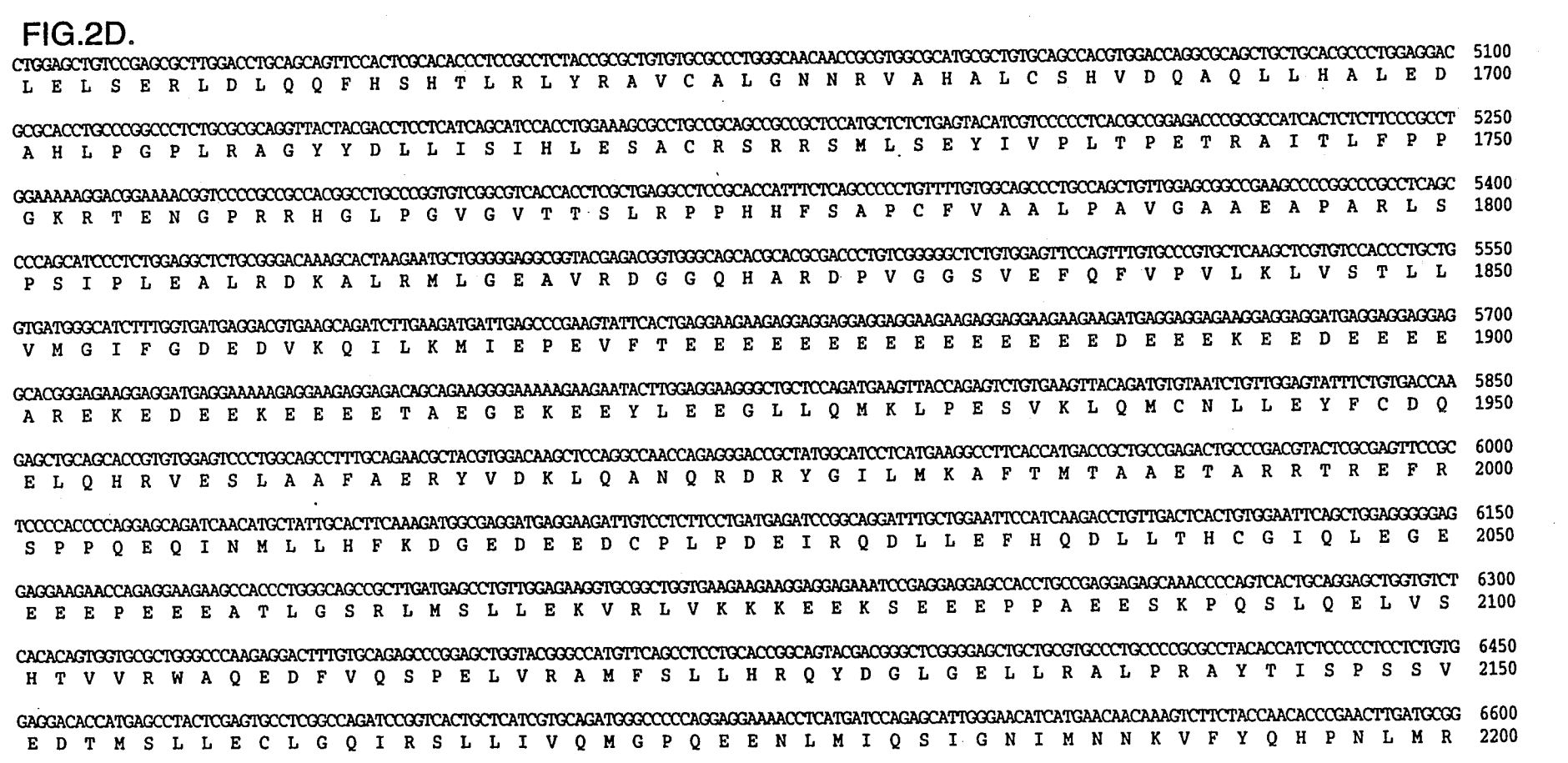
Figure 2E:
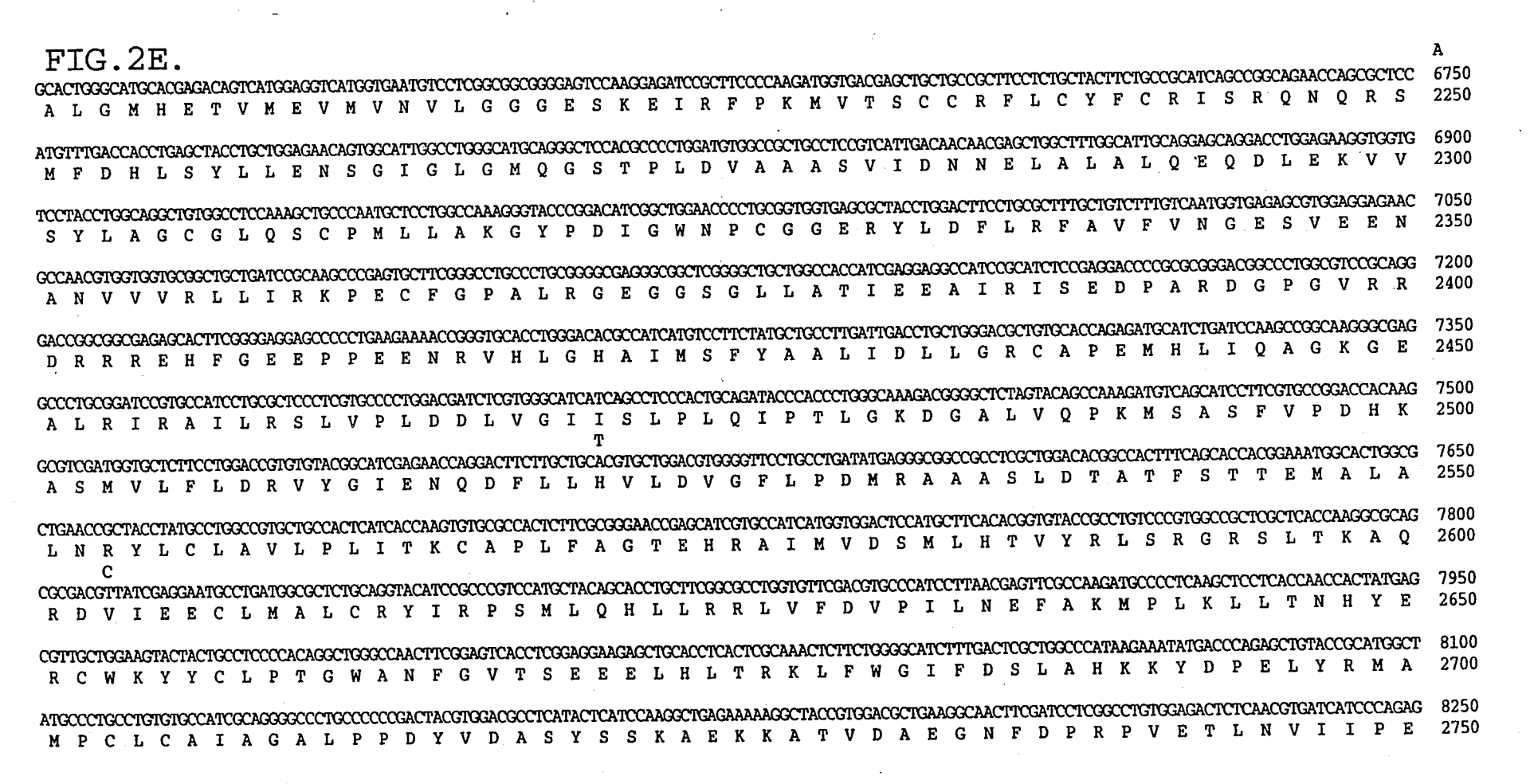
Figure 2F:
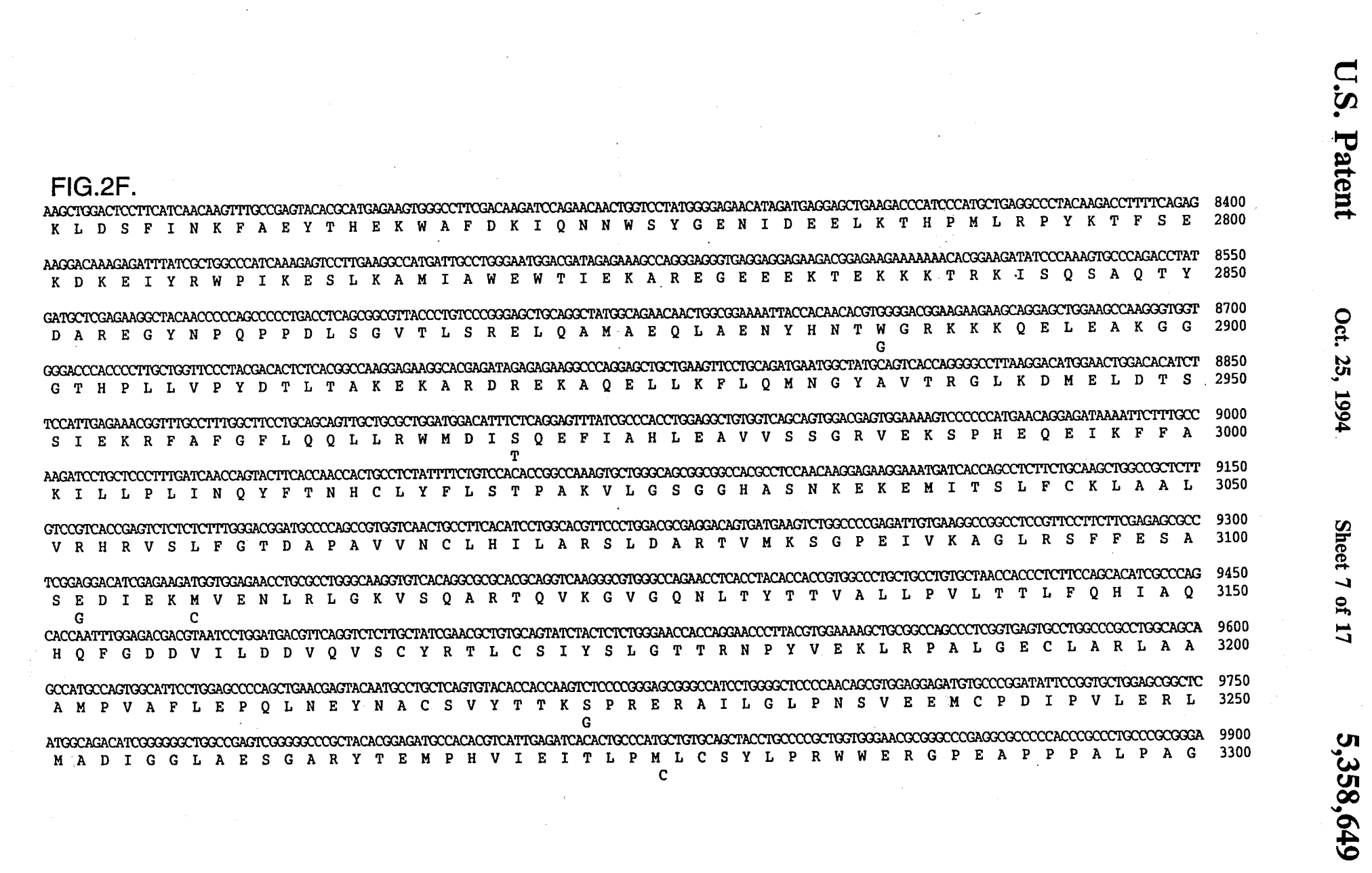
Figure 2G:
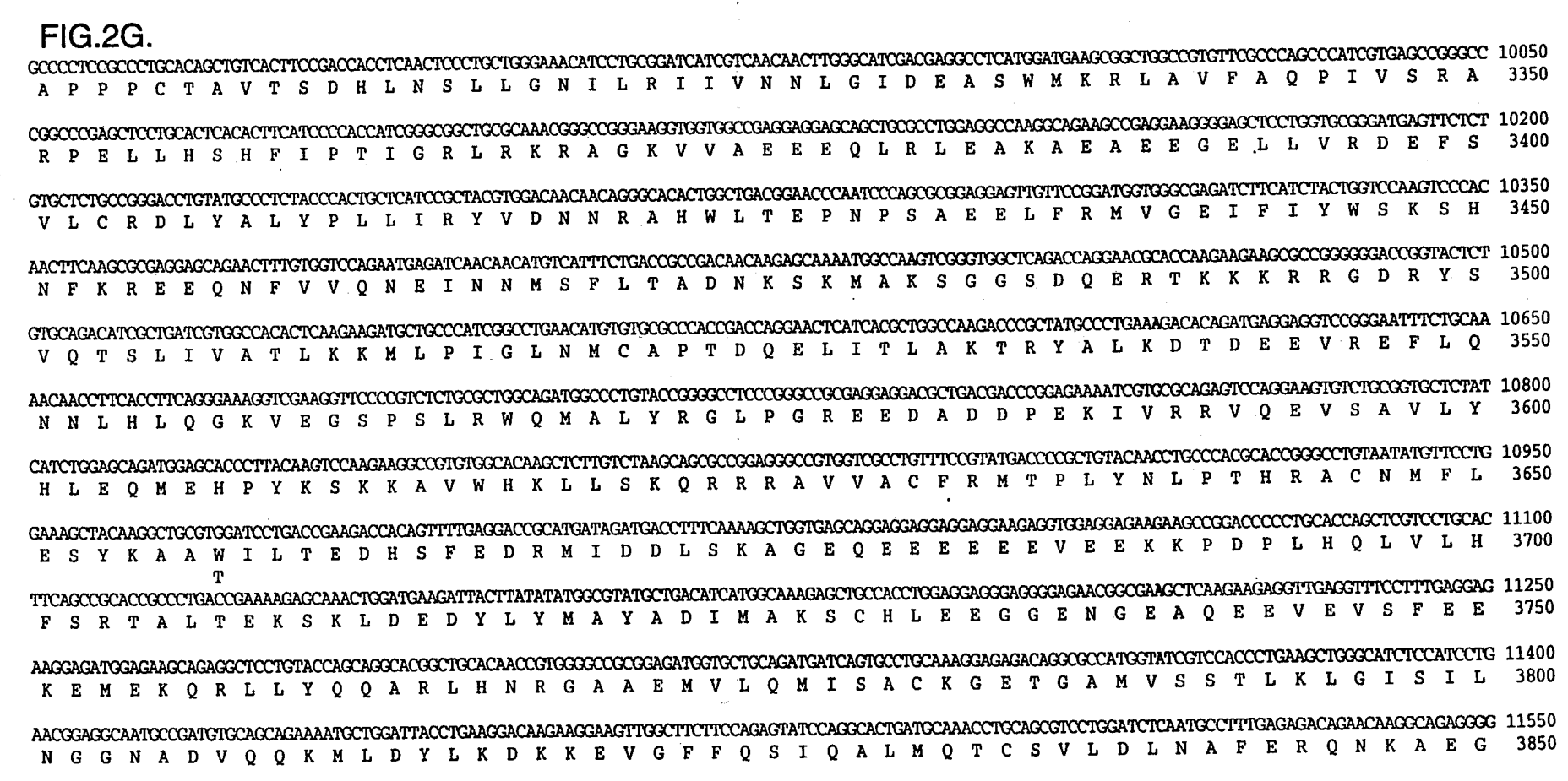
Figure 2H:
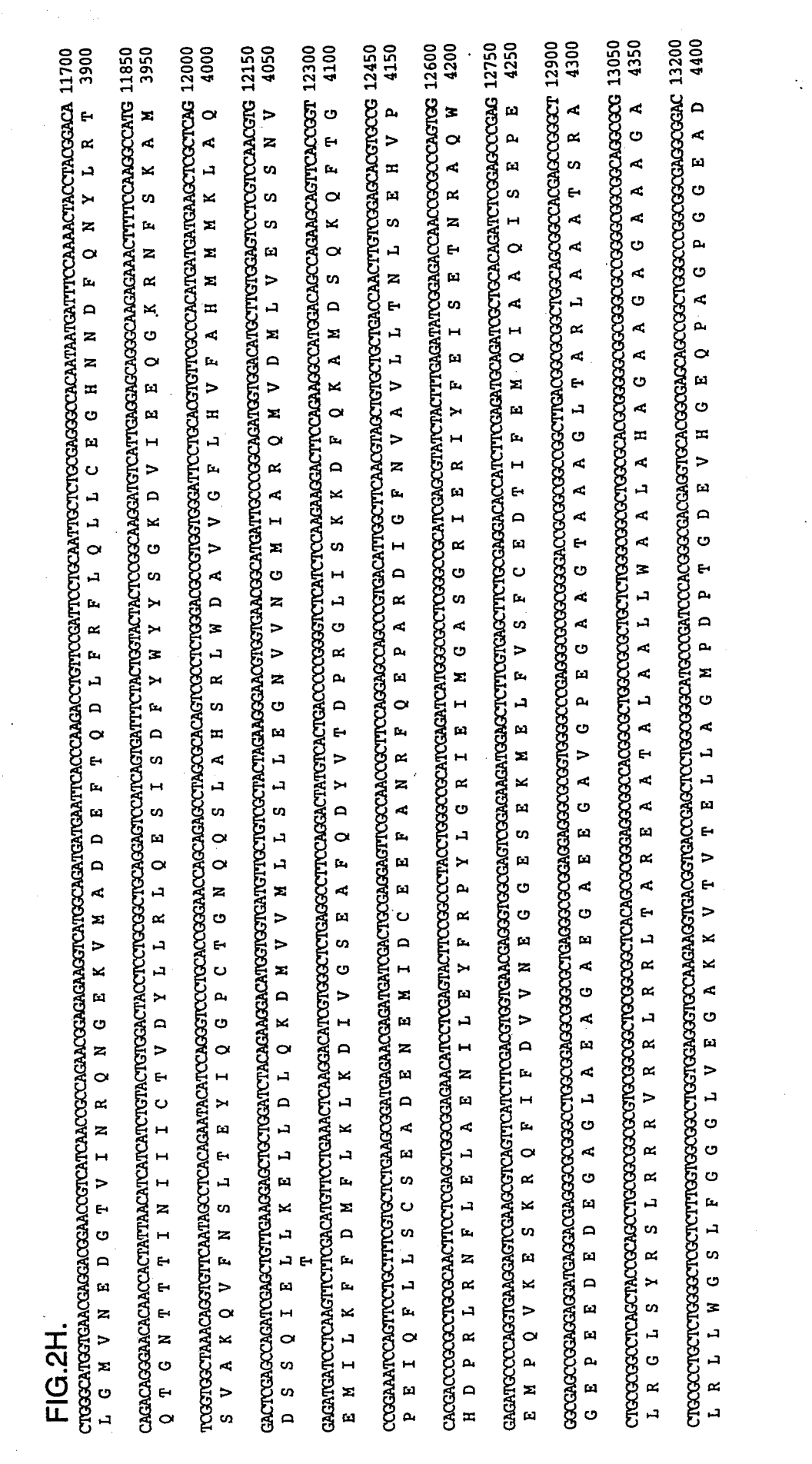

FIG. 2 is the nucleotide sequence (second row) and the deduced amino acid sequence (third row) of MH mutant porcine ryanodine receptor cDNA and the nucleotide sequence (first row) of polymorphisms in the cDNA sequence and the normal amino acid arginine 615 of (fourth row);

FIG. 4. (A) Nucleotide and deduced amino acid sequences of part of the exon in which the single arginine 615 to cysteine mutation was located. The forward primer used in PCR amplification corresponded to the sequence of nucleotides 1811 to 1834, which are overlined, while the reverse primer was complementary to nucleotides 1861 to 1884, which are also overlined. The alteration of the normal sequence GCGC1845 to the mutant sequence GTGC1845 led to the deletion of a Hin PI restriction endonuclease site in the mutant sequence. A second polymorphism (C in Yorkshire or G in Pietrain at position 1878) is also noted.

FIG. 5 (B) Detection of the C to T mutation at position 1843 by Hin PI restriction endonuclease cleavage in the 74 bp PCR product from porcine genomic DNA (21). Cleavage of the product generates 41 and 33 bp fragments. Lanes 1 and 2, Hin PI digestion of one allele (Poland China); lanes 3 and 4, digestion of both alleles (Duroc) and lanes 5 and 6, lack of digestion (n/n Pietrain).

FIG. 5 (C) Detection of the A to G polymorphism at position 4332 by Ban II restriction endonuclease cleavage of a 160 bp PCR product from porcine genomic DNA (21). Cleavage of the product generated 124 and 36 bp fragments. Lanes 1 and 2, Ban II digestion of one allele (Duroc); lanes 3 and 4, lack of digestion (N/N Yorkshire); and lanes 5 and 6, digestion of both alleles (n/n Poland China).

FIG. 5 (D) Detection of the G to A polymorphism at position 13878 by Rsa I restriction endonuclease cleavage of a 227 bp PCR product from porcine genomic DNA (21). Cleavage of the product generated 111 and 116 bp fragments which move in the acrylamide gel as a single band. Lanes 1 and 2, digestion of one allele (N/n Yorkshire x Pietrain); lanes 3 and 4, digestion of both alleles (N/N Landrace); and lanes 5 and 6, lack of digestion (n/n Landrace).

FIG. 6 - Nucleotide and deduced amino acid sequences of a part of the porcine ryanodine receptor gene in which the MH mutation is located. Capital letters indicate exon sequences, whereas small letters indicate intron sequences. The deduced amino acid sequences are indicated for exon sequences. The locations of the primers used for PCR amplification of the 1.6 kb genomic sequence are doubly overlined. The locations of primers used for the amplification of the 659 bp fragment are singly overlined. The box indicates the location and nature of nucleotide and amino acid alterations causative of MH. The constant HgiAI restriction endonuclease sites are underlined; the polymorphic HgiAI site is underlined with a hatched line.

DETAILED DESCRIPTION OF THE INVENTION

Figure 1:
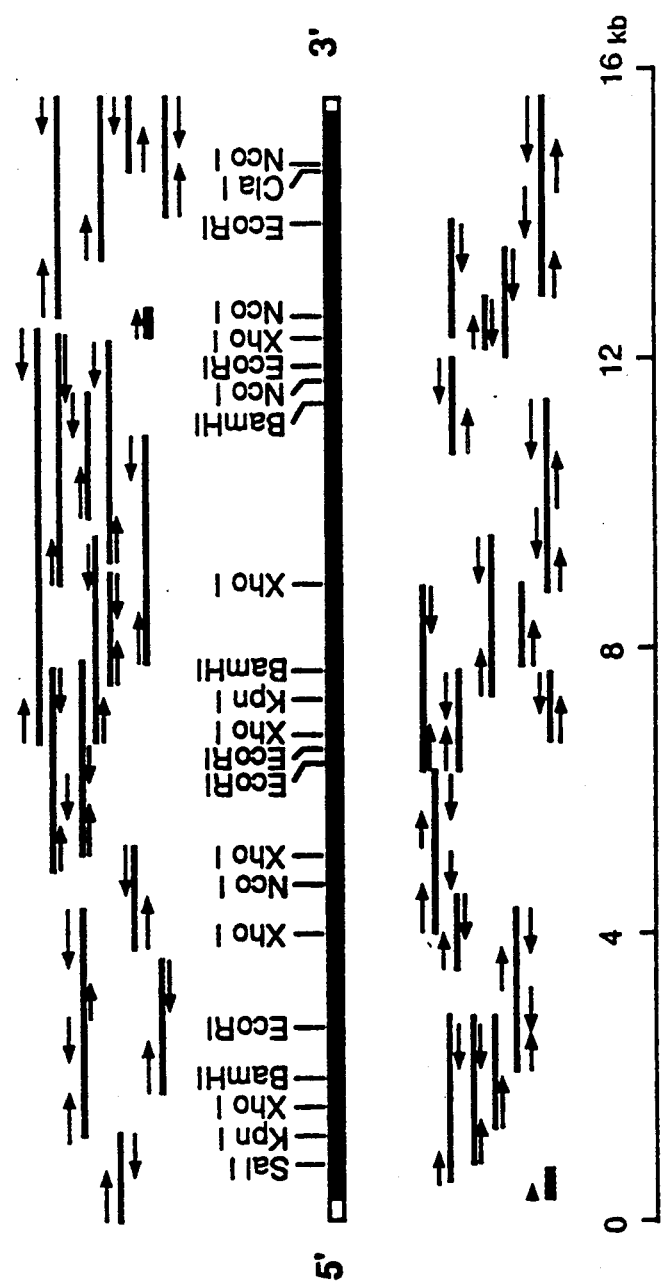
FIG. 1 is a schematic drawing showing the restriction endonuclease map for the MH mutant and normal porcine ryanodine receptors.

The restriction endonuclease map and sequencing strategy for the MH mutant and normal porcine RYR1 is shown in FIG. 1. More specifically, restriction endonuclease map and cloning, and sequencing strategies for cDNAs encoding for ryanodine receptor are from MH (Pietrain strains) and normal (Yorkshire strain) skeletal muscles. A series of linear clones were isolated from a Pietrain strain skeletal muscle cDNA library in lambda gt10. These clones are illustrated in the upper half of FIG. 1. A second series of cDNA clones was isolated from a Yorkshire strain skeletal muscle cDNA library in lambda ZAP. These clones are illustrated in the lower half of FIG. 1. The long central filled bar illustrates the size of the coding sequence, while the open bars at either end represent the sizes of 5' and 3' untranslated sequences. The locations of 6 basepair restriction endonuclease sites are noted. Short intermediate bars indicate the sizes and locations of cDNA clones isolated and sequenced from MH (upper) and normal (lower) cDNA libraries. For the MHS sequence (upper), arrows indicate the extent and direction of most, but not all, of the cDNA sequencing that was carried out. Sequencing in both directions was carried out for 93.3% of the sequence following subcloning of portions of the larger clones (not indicated). Sequencing in one direction of four independent clones was carried out for nucleotides-129 to 831 and of five independent clones for nucleotides 12502-12567. For the MHN sequence (lower) only the overlaps and duplications indicated were sequenced more than once. Short hatched bars indicate two regions where cDNAs were isolated and sequenced from polymerase chain reactions (PCR) [Saiki, R. K. et al Science 239:487-491 (1988)]. The lower thin bar is a marker indicating the size of the cDNA in kilobase pairs.

To obtain pig cDNA libraries, mRNAs were isolated from frozen muscle of the homozygous MH pig (Pietrain strain) and the homozygous normal pig (Yorkshire strain) [MacLennan and DeLeon (1983) *Methods Enzymol.*]. cDNA libraries were constructed using standard protocols supplied by the manufacturers of standard cDNA cloning kits.

The normal and mutant pig cDNA clones, it was discovered, could be obtained by screening the cDNA libraries with human RYR1 cDNA fragments [Zorzato et al. (1990) supra] to obtain clones covering the entire sequence. The nucleotide sequence for human cDNA is published [Zorzato et al. (1990) supra] and hence is readily available to the public. It is understood by those skilled in the art, that any library prepared from porcine skeletal muscle according to established methods should be representative of the RNA species present in the tissue and should, therefore, be the source of porcine ryanodine receptor clones.

Pigs predisposed to MH have functional excitation/contraction coupling in the absence of triggering agents, although the $Ca^{2+}$ release channel appears to have a hypersensitive gating mechanism [O'Brien, J. P., *J. Mol. Cell. Biochem.* 93:53-59 (1990)]. Accordingly, it was unlikely that the RYR1 gene, potentially causative of MH, would be altered by major deletions or premature stop codons. In order to test the postulate that a point mutation or short deletion would exist in the RYR1 gene that would be causal of porcine MH, we sequenced full length ryanodine receptor cDNA fragments from both an MH Pietrain pig and an MH normal (MHN) Yorkshire pig as already noted in FIG. 1. Sequencing of the Pietrain ryanodine receptor cDNA demonstrated the absence of a deletion or an internal stop codon. A comparison of the porcine amino acid sequence with published amino acid sequences for human [Zorato et al *J. Biol. Chem* 265:2244-2256 (1990)] and rabbit [Zorzato et al, supra; Takeshima et al *Nature,* 339:439-445 (1990)] showed about 180 differences between rabbit and pig, between human and pig, or between human and rabbit, and about 90 unique amino acid differences for each of the three sequences.

FIG. 2 is the nucleotide sequence (second row) and deduced amino acid sequence (third row) of the MH mutant (Pietrain strain) porcine ryanodine receptor cDNA, FIG. 2 is also the nucleotide sequence (first row) and deduced amino acid sequence (4th row) of the normal (Yorkshire) porcine ryanodine receptor cDNA (only differences from Pietrain are recorded for the Yorkshire sequence). The nucleotide and amino acid designations are in keeping with international convention and are well understood by those skilled in the art. Specifically, the nucleotide and deduced amino acid sequences of cDNAs encoding MH and normal porcine skeletal muscle ryanodine receptors are listed. Nucleotides are numbered positively in the 5' to 3' orientation beginning with residue 1 of the ATG codon for the initiator methionine and negatively for the 5' untranslated region, beginning from the 5' side of residue 1. Amino acids are numbered positively beginning at the initiator methionine codon. Each group of lines has 4 components: i) the normal nucleotide sequence where it differs from the MH sequence (17 polymorphisms are noted); ii) the nucleotide sequence of the MHS ryanodine receptor cDNA; iii) the deduced amino and sequence of the MHS cDNA; iv) the amino acid sequence of the normal ryanodine receptor where it differs from MHS. The single amino acid substitution, cysteine 615 (MHS) for arginine 615 (MHN), is boxed.

In order to detect a point mutation in the Pietrain RYR1 gene, we sequenced a full length cDNA from the Yorkshire breed for comparative purposes. We detected the already noted 17 polymorphisms between the two breeds which are identified in FIG. 2. Only one of the polymorphisms, replacement of C1843 in the cDNA from the MHN breed with T1843 in the cDNA from the MHS breed led to an alteration in the amino acid sequence from arginine 615 in the MHN animal to cysteine 615 in the MHS animal.

The deduced amino acid sequence of the open reading frame is numbered from 1 to 5035. The 3' untranslated region, beginning after the TGA termination codon, is 144 bp long. A canonical polyadenylation signal AATAAA [Proudfoot and Brownlee (1976) *Nature* 263:211-214] is found 16 bases upstream of the polyadenylation site and this is followed closely by a TG-rich sequence, characteristic of sequences between the polyadenylation signal and the polyadenylation site [McLauchlan et al (1985) *Nucleic Acids Res.,* 13:1347-1368]. The initiator methionine is 15105 bp upstream of the termination codon. The initiator methionine codon is present in the longer sequence ACATCATGG (SEQ ID No. 1, positions 125 to 133) which closely resembles the consensus initiation sequence, AC(A)TCATGG [Kozak (1984) *Nature* 308:241-246]. The normal and mutant porcine cDNA sequences of FIG. 2 encode proteins of 5035 amino acid with predicted molecular weights of approximately 564,743.

It is understood that the term substantially pure as used herein means that the isolated and purified DNA or protein is free of any foreign animal DNA or protein. It is also understood that, with reference to disclosed and claimed DNA or protein sequences, various functional equivalents exist which are due to substitutions in variable regions of the DNA sequence or protein which do not affect the essential function of the DNA sequence or protein sequence.

Proof that the cDNAs coded for normal and mutant porcine ryanodine receptor proteins was based on their colinearity and high degree of sequence identity (greater than 95%) with published sequences of rabbit and human [Zorzato et al. (1990) supra] and pig [Harbitz et al (1990) supra] RYR1 cDNAs. Proof that the gene giving rise to the cDNA is located on pig chromosome 6 is provided by a comparison of this sequence with a partial sequence localized to pig chromosome 6 by in situ hybridization [Harbitz et al (1990) supra).

Although 17 nucleotide sequence differences are noted between normal and pig sequences, only one, the alteration of C to T at position 1843, leads to a change in amino acid sequence from arginine 615 to cysteine 615. These nucleotide and resulting amino acid sequence changes in the RYR1 gene are causative of the predisposition to MH.

The porcine ryanodine receptor sequence is typical of other RYR1 gene products. The deduced amino acid sequence is slightly longer than the human and rabbit sequences (5035 vs. 5032 amino acids), but its molecular weight of 564,743 is similar to that of both skeletal [Takeshima et al (1990) supra; O'Brien J. P. et al, *Can. J. Vet. Res.* 54:8392 (1990)] and cardiac [Otsu et el, (1990) supra, Furuichi et al *Nature* 342:32-38 (1989)] forms. The short 3'untranslated sequence of 144 bases has a canonical polyadenylation signal 16 bp upstream of the polyadenylation site. Analysis of the predicted structure of the molecule shows the same features recognized in earlier analyses of other ryanodine receptors [Zorzato et al (1990) supra; O'Brien et al (1990) supra; Otsu et al *J. Biol Chem.* 265:13472-13483 (1990) ].

Arginine 615 lies in the NH2-terminal ⅛ of the $Ca^{2+}$ release channel protein and is part of a long hydrophilic cytoplasmic domain which includes at least the first 4000 residues in the molecule. Mignery and Sudhof [supra] have demonstrated that the InsP3 binding region lies in the NH2-terminal quarter of the InsP3 receptor. The InsP3 and ryanodine receptors are homologous [Furuichi et al supra] and there is partial sequence identity between the InsP3 binding region of the InsP3 receptor and the region of the ryanodine receptor surrounding arginine 615. Thus it is reasonable to assume that arginine 615, like the homologous residue in the InsP3 receptor, lies in a region of the ryanodine receptor that is concerned with the binding of regulators of $Ca^{2+}$ release channel gating.

Analysis of the sequence surrounding arginine 615 suggests that it lies within a beta strand domain comprised roughly of amino acids 520 to 830 [Zorzato et al (1990) supra]. The relatively hydrophobic sequence immediately preceding arginine 615 contains an interesting repeat motif of 2 hydrophobic, 1 hydrophilic and 2 hydrophobic residues (IVNLL522; LASLI530; LVSKL551; ILEVL564; VLNII578; IISLL590; LLDVL603; VCNGV612). The sequence after arginine 615 contains at least 9 predicted beta strands which end at the beginning of a tandem repeat structure [Zorzato et al (1990) supra] between residues 842 and 1015.

Alteration of an Arg-Ser bond in the MHN sequence to a Cys-Ser bond in the MHS sequence deletes a tryptic cleavage site in the MHS protein. Knudson et al [(1990) supra] have reported an alteration in the early tryptic cleavage pattern of the ryanodine receptor protein in which a 99 kDa tryptic peptide in MHS pigs replaces an 86 kDa tryptic peptide in MHN pigs. This alteration would be consistent with the deletion of a tryptic cleavage site in the abnormal 99 kDa fragment which would give rise to 86 and 13 kDa tryptic fragments in the normal sequence. The Arg to Cys mutation that we have detected is, according to our discovery, responsible for the altered tryptic cleavage pattern observed by Knudson et al [(1990) supra]. The fact that the tryptic cleavage pattern alteration is so readily evident at such early times of digestion suggests that the Arg-Ser 616 bond is exposed to trypsin. Arginine 615 is therefore located on the surface of the $Ca^{2+}$ release channel, even though this was not predicted by Marks et al [*J. Biol. Chem.* 1990) 265:13143-13149].

It is not yet clear how the mutation of Arginine 615 causes MH susceptibility. Studies of the physiological function of the MHS $Ca^{2+}$ release channel show that it is opened by $Ca^{2+}$, ATP and caffeine at concentrations several fold lower than those required for the MHN channel and that its inhibition by $Mg^{2+}$ is dampened [O'Brien, P. J. (1987) supra, O'Brien, P. J. (1986) supra and O'Brien, P. J. (1990) supra]. Thus at comparable concentration of these triggering agents, $Ca^{2+}$ release rates are higher for the sarcoplasmic reticulum from MHS than from MHN individuals [Mickelson et al supra]. Moreover, high affinity ryanodine binding to the $Ca^{2+}$ release channel, which occurs in the open channel configuration [Fleischer et al, *Proc. Natl. Acad. Sci. USA* (1985) 82:7256-7159], has an altered $Ca^{2+}$ dependency, presumably related to the extent of $Ca^{2+}$ channel opening. Altered $Ca^{2+}$ dependence of $Ca^{2+}$ release channel inactivation (closing) has also been demonstrated [Gill et al (1990) *Biophys. J.* 50:471-475]. These observations are consistent with the postulate that the MH mutation leads to channel gating which is hypersensitive to triggering agents [O'Brien, P. J. (1987) supra, O'Brien, P. J. (1986), O'Brien P. J. (1990) supra and O'Brien et al (1990) supra]. This postulate is further supported by analogy with a homologous $Ca^{2+}$ release channel. The inositol 1, 4, 5 trisphosphate (IP3) receptor [G. A. Mignery, and T. C. Sudhof, EMBO J. 9, 3893 (1990)] has demonstrated that IP3 binds to the to the NH2-terminal quarter of the IP3 receptor in a region homologous between the two receptors. There is 31% sequence identity between the 39 amino acids surrounding arginine 615. This homologous region is a strong candidate site for ligand binding in both receptors.

It is not fully understood why the mutation leads to the sustained channel opening, characteristic of the disease, when the MHS individual is exposed to inhalational anaesthetics or other MH triggering agents or to stress. A plausible explanation, which is understood to be non-limiting to this invention, is that MH triggering agents such as anaesthetics or stress-induced neuromuscular and endocine stimulation directly alter the intracellular concentrations of physiological channel gating agents such as $Ca^{2+}$, ATP, calmodulin or $Mg^{2+27}$ to the point where they will trigger opening of the hypersensitive MHS channel, but not of the MHN channel. Once opened, the MHS channel will also respond poorly to $Ca^{2+}$- and $Mg^{2+}$- induced inactivation [Gill et al (1990) supra], thereby remaining open to induce muscle contracture, hypermetabolism and, ultimately, fever.

The relationship between the MH mutation in swine and the MH mutation in humans is also not fully understood. In all respects except inheritance, the pig and human diseases are believed to be analogous Britt (1987) supra]. MH susceptibility has been proposed to be inherited in a dominant pattern in people and in a recessive pattern in swine [Britt (1987) supra and Denborough et al (1960) supra]. This postulate is probably invalid since the porcine halothane challenge test used in swine aenetic studies has been designed to detect homozygotes and to spare the lives of heterozygotes. By contrast, the conditions for detection of MH in humans either in vivo inhalation of high levels of halothane for prolonged periods in the presence of succinyl oholine; or in vitro halothane/caffeine contracture tests [Britt (1987) supra] detects human heterozygotes (homozygous MH humans are rare). Inheritance is, therefore, described as dominant. A comparable test can detect pigs heterozygous for the mutation also, thereby leading to a change in the designation of the swine inheritance pattern from recessive to dominant, the same designation as for humans. If MH susceptibility is similar in pigs and humans, it is likely that mutations in the same structural and functional domain of the RYRI gene will be causative of the disease in both species.

The site of the MHS mutation, as exposed on the surface, is a potential target for the binding of site directed, differential antibodies that can be used in the development of an antibody-based diagnostic assay for that could be carried out on the protein from isolated muscle fractions or in tissue sections.

In order to provide evidence that the amino acid sequence alternation is causative of MH, we carried out diagnosis of the association of the T1843 mutation with the MHS phenotype in a variety of pigs of deferring susceptibility status. Blood or muscle samples were isolated from 149 individual pigs at the University of Guelph for DNA based diagnosis at the University of Toronto. Tissue samples were numbered, but not otherwise identified for the Toronto study. Subsequently, 27 of these same tissue samples were provided for an additional blind repeat test. Of the 149 samples, 48 homozygous MHS Pietrain, 9 homozygous MHN Yorkshire, 2 heterozygous Yorkshire and 20 heterozygotes resulting from MHS Pietrain by MHN Yorkshire crosses had been subjected to diagnosis of MH susceptibility by the halothane challenge O'Brien et al (1990>supra], the caffeine/halothane contracture test [O'Brien et al (1990) supra] or the $Ca^{2+}$ release channel activity test [O'Brien et al, Can. Vet. Res 50:318–328 (1986)], as well as by full knowledge of the genetic background of the parental animals.

Genomic DNA was isolated from these animals and a 75 bp sequence, lying within a single exon, was amplified by the polymerase chain reaction (PCR) [Saiki et al Science 239:487–491 (1988)]. The forward primer used in PCR amplification corresponded to nucleotides 1811 to 1834 in FIG. 2. The reverse primer was complementary to nucleotides 1861 to 1884 in FIG. 2.

A 17-mer oligonucleotide sequence of the composition 5'-TGGCCGTGCGCTCCAAC-3' (Seq ID No. 2, positions 25 to 41) (probe 17-C) (nucleotide positions 1835 to 1851; SEQ ID No. 1) and a 15-mer oligonucleotide of the composition 5'-GGCCGTGTGCTCCAA-3' (SEQ ID No. 2, positions 26 to 41 with a substitution of T at base pair position 33) (probe 15-T) nucleotide positions 1836 to 1850; SEQ ID No. 1) were synthesized, end labelled with =P and used as probes [Maniatis et al Molecular Cloning: A Laboratory Manual (Cold Spring Harbor Laboratory, New York, 1982)] to detect the presence of normal and mutant alleles in the various breeds.

Figure 5A:
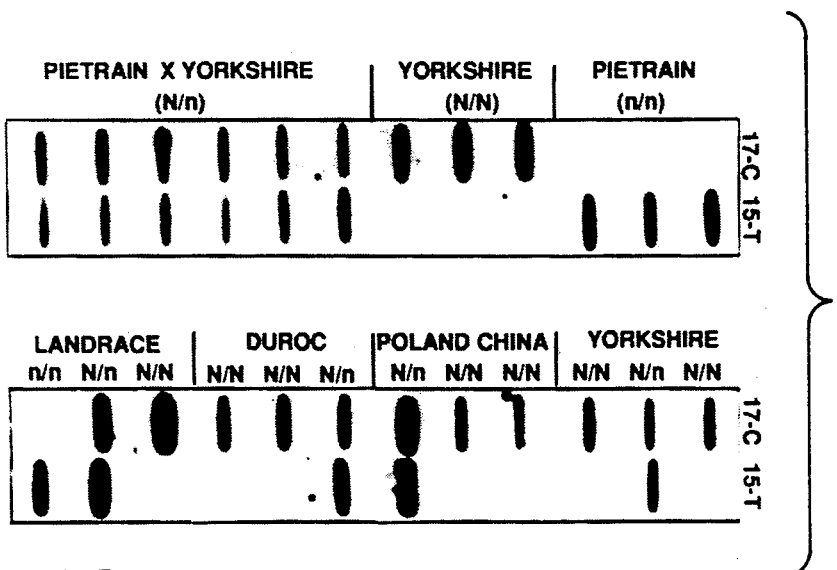
FIG. 5. (A) Detection of the arginine 615 to cysteine mutation by oligonucleotide hybridization. Autoradiographs show the binding of the two specific oligonucleotide probes to the 74 bp PCR amplified product identified in FIG. 1 from n/n Pietrain, N/N Yorkshire, or heterozygous N/n individuals from Pietrain/Yorkshire crosses (left), and of individuals from Yorkshire, Poland China, Duroc and Landrace herds (right). Oligonucleotide probe 17-C detected the MHN DNA sequence and oligonucleotide probe 15-T detected the MHS DNA sequence. Both probes bind to heterozygote sequences.
Figure 5B:
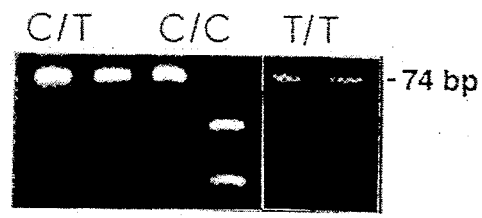

These two oligonucleotides were used as differential hybridization probes to detect the presence of C and T alleles in the various breeds as shown in FIG. 5A. In view of the mutation deleting a Hin P1 site, as specifically noted in FIG. 4, reliance of this loss of site was used in the same PCR product as a restriction enzyme test, the results of which are shown in FIG. 5B.

Figure 3:
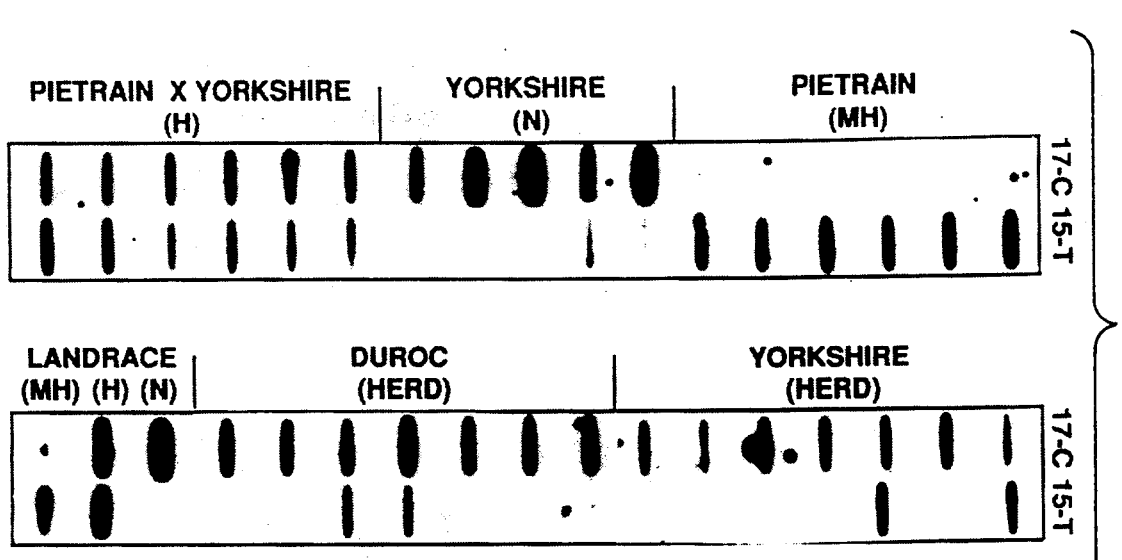
FIG. 3 is a series of slot blot tests to detect the presence of normal and mutant alleles in various identified breeds.

FIG. 3 is an autoradiograph illustrating the diagnosis of homozygous MH susceptible, homozygous normal and heterozygous MH susceptible/normal alleles in Pietrain, Landrace, Duroc and Yorkshire pigs. These DNAs are slot blotted [Tlsty et al (1982) in "Gene amplification" (R. C. Schimke ed.) CSH Laboratory Press pp. 231–238] onto BA85 nitrocellulose paper as described by the manufacturer (Scnleicher and Schuell) baked for 2 hours at 80°, prehybridized for 2 hours and hybridized for 4 hours with one or the other of two =P-labelled oligonucleotide probes in a solution containing 6×SSC 0.1% sodium dodecyl sulfate and 10×Denharts solution. The first probe, of the composition (probe 17-C), binds selectively to the normal sequence at 61° in the presence of 6×SSC and 0.1% SDS while the second, of the composition (probe 15-T) binds selectively to the corresponding MH susceptible sequence at 55° in the same buffer. Heterozygous DNAs will bind both probes at the two different temperatures. In FIG. 3, we illustrate that these two probes will differentiate homozygous homozygous MHN and heterozygous genotypes in Pietrain, Yorkshire and Yorkshire/Pietrain crosses. Of the 149 animals in which DNA based diagnosis was compared with standard methods of diagnosis of MH susceptibility, there was high level of agreement between the two methods (See Table 1). The study therefore proves that the T1843 for C1843 mutation in the DNA sequence, leading to a cysteine 615 for arginine 615 substitution in the amino acid sequence, is correlated with MH susceptibility in Pietrain and Yorkshire swine. The conclusion that this mutation is causative of MH susceptibility is therefore fully justified.

Study of the correlation between phenotyloic and genotypic diagnosis is complicated by the lack of a well defined phenotypic test for the N/n (heterozygous MH) genotype and by the fact that a low percentage of animals reacting to the commonly used halothane challenge test are of the N/n genotype while a low percentage of those that do not react are of the n/n genotype (homozygous MH) [P. J. O'Brien, Vet. Res. Commun. 11:527 (1987); P. J. O'Brien, A. Klip, B. A. Britt, B. I. Kalow, Can. J. Vet. Res. 54:83 (1990); P. J. O'Brien et al., Am. J. Vet. Res. 46:1451 (1985)]. The T/T allelic pair was found at nucleotide 1843 in each of 48 pietrain animals from an inbred herd. All breeding stock used in development of this herd had been shown to be n/n by testing of progeny using the halothane challenge test or the halothane/caffeine contracture test [P. J. O'Brien, A. Klip, B. A. Britt, B. I. Kalow. Can. J. Vet. Res. 54:83 (1990); P. J. O'Brien et al., Am. J. Vet. Res. 46:1451 (1985]. Of these 48, 11 were diagnosed in this study as n/n in a halothane/caffeine contracture test and 6 in the test for hypersensitive mating of the $Ca^{2+}$ release channel (S. T. Ohnishi, S. Taylor. G. A. Gronert, FEBS Lett. 161:103 (1983); P. J. O'Brien, Mol. Cell. Biochem. 93:53 (1990)]. The C/C allelic pair was found in 36 of 43 and the C/T allelic pair in 7 of 43 Yorkshire animals from a closed herd, also inbred for 10 years for halothane resistance, but originating in commercial stock in which 0.78% have been found to be positive for the halothane challenge test Pietrain and Yorkshire swine were obtained from closed herds with inbreeding programs controlled for more than 10 years. Selection of Pietrain breeders was based on production of offspring positive for either the halothane challenge test or the halothane=and caffeine contracture test, the reference tests for diagnosis of MH susceptibility [P. J. O'Brien, Vet. Res. Commun. 11:527 (1987); B. A. Britt, in Malignant Hyperthermia, B. A. Britt, ed. (Martinus Nijhoff, Boston, 1987), pp. 11–42; P. J. O'Brien, A. Klip, B. A. Britt. B. I. Kalow, Can. J. Vet. Res. 54:83 (1990)]. Selection of Yorkshire breeders was based on negative halothane challenge tests and production of offspring negative for this test. In the halothane and caffeine contracture tests, swine were considered MH-susceptible if a 1 g increase in tension (CSC) occurred with less than 4 mM caffeine or if more than 0.5 g tension developed with 5% halothane; normal if CSC was greater than 7 mM and halothane produced less than 0.2 g increase in tension; and heterozygous if CSC was between 5 and 6 [P. J. O'Brien, B. I. Kalow, N. Ali, L. A. Lassaline, J. H. Lumsden, J. H. Am. J. Vet. Res. 51:1038 (1990)]. To confirm the presence of a functional defect in the ryanodine receptor in MHS swine, microassays for hypersensitive gating of the $Ca^{2+}$ release channel [S. T. Ohnishi, S. Taylor, G. A, Gronert, FEBS Lett. 161:103 (1983); P. J. O'Brien, Mol. Cell. Biocnem. 93:53 were performed on isolated skeletal muscle sarcoplasmic reticulum. Half-maximal Ca-release occurred at less than 2 mM caffeine for all Pietrains and at greater than 7 mM caffeine for all Yorkshires. The estimate of the allele frequency of 8.8% for 24 Duroc swine unrelated to known reactor swine is based on the assumption that it is similar to that of Ontario Yorkshire swine [D. C. Seeler, W. M. McDonell, P. K. Basrur, Can. J. Comp. Med. 47. 284 (1983). This estimate was modified to 31.3%, however, for a group of 8 Durocs, 6 of which were the offspring of 2 which had produced both reactor and non-reactor offspring and were, therefore, heterozygotes. The combined T allele frequency for 32 Durocs, therefore, was estimated to be 14.4%]. Of the animals studied, 9 were diagnosed as N/N by the halothane/caffeine contracture test and found to be C/C in the DNA based test. Two had intermediate halothane/caffeine contracture test results and were tentatively diagnosed as N/n and shown to De C/T in the DNA based test. The finding of a T allele frequency of 8.1% in this inbred herd was correlated with the earlier finding of 8.8% for the allele in the Yorkshire population from which the herd was derived and 9.@% based on our present halothane/caffeine contracture test results for 11 animals [Pietrain and Yorkshire swine were obtained from closed herds with inbreeding programs controlled for more than 10 years. Selection of Pietrain breeders was based on production of offspring positive for either the halothane challenge test or the halothane and caffeine contracture test, the reference tests for diagnosis of MH susceptibility [P. J. O'Brien, Vet. Res. Commun. 11:527 (1987); B. A. Britt, in Malignant Hyperthermia, B. A. Britt, ed. (Martinus Nijhoff, Boston. (1987), pp. 11–42; P. J. O'Brien, A. Klip, B. A. Britt, B. I. Kalow, Can. J. Vet. Res. 54:83 (1990)]. Selection of Yorkshire breeders was based on negative halothane challenge tests and production of offspring negative for this test. In the halothane and caffeine contracture tests, swine were considered MH-susceptible if a 1 g increase in tension (CSC) occurred with less than 4 mM caffeine or if more than 0.5 g tension developed with 5% halothane: normal if CSC was greater than 7 mM and halothane produced less than 0.2 g increase in tension; and heterozygous if CSC was between 5 and 6 [P. J. O'Brien, B. I. Kalow, N. Ali, L. A. Lassaline, J. H. Lumsden, J. H. Am. J. Vet. Res. 51:1038 (1990)]. To confirm the presence of a functional defect in the ryanodine receptor in MHS swine, microassays for hypersensitive gating of the $Ca^{2+}$ release channel [S. T. Ohnishi, S. Taylor. G. A. Gronert, FEBS Lett. 161:103 (1983); P. J. O'Brien, Mol. Cell@ Biochem. 93:53 (1990);] were performed on isolated skeletal muscle sarcoplasmic reticulum. Half-maximal ca-release occurred at less than 2 mM caffeine for all Pietrains and at greater than 7 mM caffeine for all Yorkshires. The estimate of the allele frequency of 8.8% for 24 Duroc swine unrelated to known reactor swine is based on the assumption that it is similar to that of Ontario Yorkshire swine [D. C. Seeler, W. M. McDonell, P. K. Basrur, Can. J. Comp. Med. 47. 284 (1983). This estimate was modified to 31.3%, however, for a group of 8 Durocs, 6 of which were the offspring of 2 which had produced both reactor and non-reactor offspring and were, therefore, heterozygotes. The combined T allele frequency for 32 Durocs, therefore, was estimated to be 14.4%]. Of 14 animals derived from crosses of Pietrain X Yorkshire, all had the C/T genotype, as did 5 proven halothane resistant Landrace animals resulting from the mating of animals from inbred halothane resistant and halothane sensitive lines. A single Poland China pig, diagnosed as n/n by both breeding and halothane/caffeine contracture testing, had the T/T phenotype. The DNA based test was also applied to 71 animals from commercial herds in which a low frequency of halothane susceptible animals was known to exist, but in which the N/n and N/N animals were not distinguished phenotypically. It was found that 11 C/T and 21 C/C genotypes among 32 Durocs, resulted in a frequency for the T allele of 17.2%, where the predicted frequency was 14.4% and a T allele frequency of 9.1% in 11 Poland China where the T allele frequency was predicted to be comparable to that in Yorkshires (8.8%). No T alleles were found in 20 Hampshire pigs, correlating with the fact that MH Hampshire have never been reported in Canada. Eight Landrace halothane reactors were analyzed where N/n and n/n could not be distinguished phenotypically and 5 C/T and 3 T/T genotypes were found. Estimates of allele frequency based on phenotypic analyses were highly correlated with genotypic analysis (P<0.0001).

TABLE I (a) Agreement Between Diagnosis of MH Susceptibility by Caffeine and Halothane Hypersensitivity Tests and Diagnosis by DNA-based Test

| Diagnosis | Swine tested | Tests done | P value |
|---|---|---|---|
| N/N versus | 9 | 12 | $10^{-12}$ |
| N/n or /n/ | 77 | 107 | |
| n/n versus | 48 | 68 | $10^{-4}$ |
| N/N or N/n | 93 | 104 | |
| N/n versus | 15 | 23 | $10^{-7}$ |
| N/N or n/n | 57 | 81 | |

P values indicate the statistical significance for agreement of all diagnoses as determined by Cochran's Q-test for agreement of categorial data.
N/N = homozygous normal phenotype
n/n = homozygous MH phenotype
N/n = heterozygous MH phenotype (b) Correlation of estimates of MH gene frequency in different herds by different hypersensitivity tests and by the DNA-based test

| Herd | Swine Tested | MH Gene Frequency hypersensitivity test | Estimate DNA-probe test |
|---|---|---|---|
| Inbred Pietrain (P) | 48 | 1.00 | 1.00 |
| Normal Yorkshires | 9 | 0.00 | 0.00 |
| Heterozygous Yorkshires (Y) | 2 | 0.50 | 0.50 |
| P X Y crossbreds | 14 | 0.50 | 0.50 |
| Y with no homozygous MHS pigs | 43[a] | 0.09 | 0.08 |
| Halothane reactive MHS Landrace | 8 | 0.50–1.0 | 0.68 |
| Halothane resistant MHS Landrace | 5 | 0.50 | 0.50 |
| Duroc with no homozygous MHS but producing | 31 | 0.50–0.15 | 0.10 |

TABLE I-continued homozygous MHS pigs

The P value for correleation of estimates of MH gene frequency is $10^{-12}$ as determined by David's r-test for correlation.
[a]Estimate of gene frequency by caffeine hypersensitivity tests is based on 11 animals.

We extended the study to a herd of Yorkshires (32 animals), believed to be free of MH, and to representatives of herds of Duroc (31 animals) and Landrace (19 animals) breeds in which MHS susceptible animals had been detected by the halothane challenge test. DNA based diagnosis of the individuals from all of these herds revealed the presence of heterozygotes for the MH mutation (FIG. 2). DNA based diagnosis of these animals was not verified by other specific symptomatic tests. The study clearly illustrates that diagnosis by a DNA based test is feasible for Pietrain, Yorkshire, Duroc and Landrace breeds, all of which are characterized as lean, heavily muscled pigs.

The fact that the probes are useful for the diagnosis of MM in four major breeds of lean, heavily muscled pigs strongly suggests that the MM gene in these strains has a single common origin and that it has been introduced into these breeds from a common source.

Figure 5C:
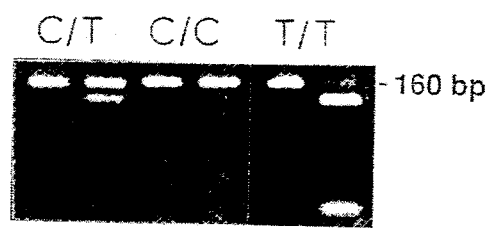
Figure 5D:
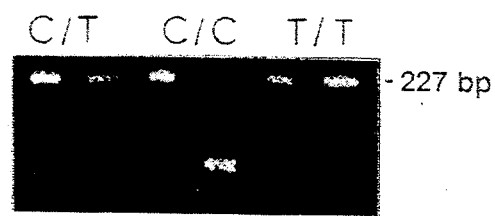

To see if the mutation is associated with a specific halotype in all breeds we analysed the cosegregation of the mutation at nucleotide 1843 with a polymorphism at nucleotide residue 4332 (Table II) which alters a Ban II site within a 160 bp exon in the ryanodine receptor gene (FIG. 5C) and of a polymorphism at nucleotide 13878 (Table II) which alters an Rsa I site within a 261 bp exon (FIG. 5D). By analogy with the human gene (M. Phillips, J. Fujii and D. H. MacLennan, unpublished), the Ban II site is about 35 Kbp and the Rsa I site 145 kbp downstream of the Hin P1 site.

The Hin P1 cleavage site, incorporating nucleotide 1843, is absent in inbred Pietrain DNA, the Ban II cleavage site is present and the Rsa I cleavage site is absent, so that the MH Pietran haplotype is Hin P1 Ban II+ Rsa I. Data presented in Table III show that all diagnosed n/n individuals from Pietrain, Landrace and Poland China breed carried only the Hin P1 Ban II+ Rsa I haplotype. The Ban II−/− and Rsa I+/+ allelic pairs were excluded from all Him P1+/− individuals, tentatively identified as N/n, so that all Hin P1+/− individuals in Yorkshire, Duroc, Landrace and Poland China breeds contained a potential Hin P1− Ban II+ Rsa I− haplotype. In Him P1+/+ individuals, tentatively identified an N/N in each of the six breeds, the Hin P1+/+ genotype coexisted with several combinations of Ban II and Rsa I polymorphisms, including Ban II+/+, Rsa I−/−, the genotype that was found for these two polymorphisms in all Hin p1−/− animals, and the Ban II−/− Rsa I+/+ genotype, excluded from the Hin P1+/− genotype. On the basis of these results, a common origin for the chromosome containing the T allele and, by association, a common ancestry for all the MH animals in all five breeds, as indicated.

Knowledge of this molecular alteration associated with MH and with specific RYR1 haplotype has allowed us to develope a simple, accurate, and non-invasive test for the altered RYR1 gens that will make it possible to eliminate this gene from each of these breeds if that is desired. The high frequency of MH susceptibility in Pietrain, Yorkshire, Poland China, Duroc and Landrace breeds of swine, however, may result from the widespread selection for leanness and muscularity in breeding stock. A clear demonstration of an association between a defective RYR1 gens and lean body mass might make it advantageous to reintroduce the defective RYRI gene selectively into breeding stock (1) to yield F1 generation N/n market animals which might all have superior lean body mass (1) and acceptable meat quality (23).

TABLE II

| Nucleotide (Amino Acid) | Yorkshire | Pietrain |
| --- | --- | --- |
| 276 (92) | TCC (Ser) | TCA (Ser) |
| 1843 (615) | CGC (Arg) | TGC (Cys) |
| 1878 (626) | CTG (Leu) | CTC (Leu) |
| 3942 (1314) | GGT (Gly) | GGC (Gly) |
| 4332 (1444) | GAA (Glu) | GAG (Glu) |
| 4365 (1455) | CCC (Pro) | CCT (Pro) |
| 6738 (2246) | CAA (Gln) | CAG (Gln) |
| 7563 (2521) | CAT (His) | CAC (His) |
| 7809 (1603) | GTC (Val) | GTT (Val) |
| 8811 (2937) | GCG (Ala) | GCA (Ala) |
| 9033 (3021) | ACT (Thr) | ACA (Thr) |
| 9456 (3152) | CAG (Gln) | CAA (Gln) |
| 9471 (3157) | GTC (Val) | GTA (Val) |
| 9822 (3274) | ACG (Thr) | ACA (Thr) |
| 9982 (3328) | CTG (Leu) | TTG (Leu) |
| 11121 (3707) | ACT (Thr) | ACC (Thr) |
| 12171 (4057) | TTT (Phe) | TTC (Phe) |
| 13877 (4626) | GTG (Val) | GTA (Val) |

TABLE III

| | Haplotype/genotype | | | Breed | | | | | | |
| --- | --- | --- | --- | --- | --- | --- | --- | --- | --- | --- |
| | HinPI | BanII | RsaI | Pietrain | Yorkshire | Poland China | Duroc | Landrace | Hampshire | Total |
| T/T | − | + | − | 18/18 | — | 2/2 | — | 4/4 | — | 24/24 |
| C/T | +/− | +/− | +− | — | 6/9 | 5/6 | 8/10 | 4/11 | — | 23/36 |
| | +/− | +/+ | +/− | — | — | 1/6 | — | — | — | 1/36 |
| | +/− | −/− | +/− | — | — | — | — | — | — | — |
| | +/− | +/− | +/+ | — | — | — | — | — | — | — |
| | +/− | +/+ | +/+ | — | — | — | — | — | — | — |
| | +/− | −/− | +/+ | — | — | — | — | — | — | — |
| | +/− | +/− | −/− | — | 1/9 | — | 1/10 | 1/11 | — | 3/36 |
| | +/− | +/+ | −/− | — | 2/9 | — | 1/10 | 6/11 | — | 9/36 |
| | +/− | −/− | −/− | — | — | — | — | — | — | — |
| C/C | +/+ | +/− | +/− | — | — | 1/4 | 3/8 | — | 5/20 | 9/45 |
| | +/+ | +/+ | +/− | — | — | — | — | — | — | — |
| | +/+ | −/− | +/− | — | — | — | — | — | — | — |
| | +/+ | +/− | +/+ | — | 2/12 | — | — | — | — | 2/45 |
| | +/+ | +/+ | +/+ | — | — | — | — | — | — | — |
| | +/+ | −/− | +/+ | — | 4/12 | 3/4 | 4/8 | 1/1 | 2/20 | 14/45 |
| | +/+ | +/− | −/− | — | — | — | 1/8 | — | — | 1/45 |
| | +/+ | +/+ | −/− | — | 6/12 | — | — | — | 13/20 | 19/45 |
| | +/+ | −/− | −/− | — | — | — | — | — | — | — |

Table II.

Polymorphisms noted in the full length cDNA sequences [Poly (A)+ RNA was isolated [D. H. MacLennan and S. de Leon, Methods Enzymol. 96:570 (1983)] from skeletal muscle from a proven N/N Yorkshire pig and from a proven n/n Pietrain pig. Complementary cDNA was synthesized using the cDNA Synthesizing System supplied by Bethesda Research Laboratories (BRL), and cDNA libraries were constructed in λ gtlO (BRL) and λ ZAP (Stratagene) according to the manufacturer. Priming of n/n Pietrain poly(A)+ RNA (10 ug) for cDNA synthesis was carried out with 100 ng oligo d(T)$_{17}$, a 24 nucleotide primer complementary to the human skeletal muscle ryanodine receptor nucleotides 1243 to 1266 (10) and 18 nucleotide primers complementary to rabbit skeletal muscle ryanodine receptor nucleotides 3499 to 3516, 4900 to 4917 and 9123 to 9140 (9). Priming of N/N Yorkshire poly(A)+ RNA (10 ug) was carried out with the same set of oligonucleotides, plus 24 nucleotide sequences complementary to human nucleotides 4000 to 4023, 5859 to 5882 and 11099 to 11122. Restriction endonuclease fragments from the human skeletal muscle ryanodine receptor cDNA were used as probes to screen porcine cDNA libraries with filter washing at 60° [T. Maniatis, E. F. Fritsch, and J. Sambrook, Molecular Cloninc: A Laboratory Manual (Cold Spring Harbor Laboratory, New York (1982)]. The polymerase chain reaction [R. K. Saiki et al., Science 239, 487 (1988)] was used to isolate nucleotides 12502 to 12567 in Pietrain cDNA and nucleotides −24 to 448 in Yorkshire cDNA. All cDNAs were subcloned into the Bluescript vector (Stratagene) for sequence analysis [F. Sanqer, S. Nicklen, A. R. Coulson, Proc. Natl. Acad. Sci. U.S.A. 74:5463 (1977)] with the T7 sequencing kit (Pharmacia). Five independent PCR products were sequenced for detection of potential artifactual sequences] that encode ryanodine receptors from N/N Yorkshire and n/n Pietrain swine. The left column identifies nucleotide numbers in which polymorphisms were found by sequencing (with the exception of nucleotides 1843, 4332 and 13878, these were not confirmed by alternate tests) and amino acids numbers potentially altered. Alteration of nucleotide 1843 deletes a Hin P1 site (GCGC to GTGC); of 4332 creates a Ban II site (GAACCC to GAGCCC); and of 13878 deletes an Rsa I site (GTAC to ATAC) in the MH haplotype. The center (Yorkshire) and right (Pietrain) columns identify the nucleotide polymorphisms (bold) within their respective codons and the effect of the polymorphism on the amino acid encoded. Nucleotides encoding MHN and MHS ryanodine receptors are numbered positively in the 5' to 3orientation, beginning with residue 1 of the ATG initiator methionine. Amino acids are numbered positively beginning with the initiator methionine.

Table III.

Haplotype and genotype analysis of the RYRI gene in six swine breeds. PCR amplified products that surround the mutation at nucleotide 1843 (Hin PI) or polymorphic sites at nucleotides 4332 (Ban II) and 13878 (Rsa I) were analysed for the presence (+) or absence (−) of appropriate restriction endonuclease sites (21). On the basis of the results of Hin P1 digestion, animals were grouped as T/T (proven n/n); C/T (probable N/n); and C/C (probable N/N). The Hin PI− Ban II+ Rsa I− haplotype was identical for the two n/n chromosomes in each individual in each breed, and, therefore, chromosomes were counted individually in the n/n row. The haplotypes of the probable N/n and N/N chromosomes differed among individuals and breeds and were counted as chromosome pairs.

We therefore have a reasonable prediction that the same defective gene will be found in any other breed of pig, especially where MH has been associated with lean body mass, probably by the introduction into the breeding stock of individuals from other breeds carrying the original MH gens. The availability of probes 17-C and 15-T should make it feasible to eliminate the defective RYR1 gene from each of these breeds within a short period, if that is desired by pig breeders.

One major application of the DNA sequence information of the normal and mutant MH genes is in the area of genetic testing, carrier detection and herd diagnosis. Pigs (male and female) carrying mutations in the ryanodine receptor may be detected at the DNA level with the use of a variety of techniques. The genomic DNA used for the diagnosis may be obtained from body cells, such as those present in peripheral blood, urine, saliva tissue biopsy and surgical specimen. The DNA may be used directly for detection of specific sequence or may be amplified enzymatically in vitro by using PCR [Saiki et al. Science 230:1350–1353, (1985), Saiki et al. Nature 324:163–166 (1986)] prior to analysis. RNA or its cDNA form may also be used for the same purpose. Recent reviews of this subject have been presented by Caskey, [Science 236:1223-8 (1989)] and by Landegren et al [Science 242:229–237 (1989)].

The detection of specific DNA sequence may be achieved by methods such as hybridization using specific oligonucleotides [Wallace et al. Cold Spring Harbour Symp. Quant. Biol. 51:257–261 (1986)], direct DNA sequencing [Church and Gilbert, Proc. Nat. Acad. Sci. USA 81:1991–1995 (1988)], the use of restriction enzymes [Flavell et al. Cell 15:25 (1978), Geever et al Proc. Nat. Acad. Sci. USA 78:5081 (1981)], discrimination on the basis of electrophoretic mobility in gels with denaturing reagent [Myers and Maniatis, Cold Spring Harbour Sym. Quant. Biol. 51:275–284 (1986)], temperature gradient gel electrophoresis, RNase protection [Myers, R. M., Larin, J., and T. Maniatis Science 230:1242 (1985)], chemical cleavage [Cotton et al Proc. Nat. Acad. Sci. USA 85:4397–4401, (1985)] and the ligase-mediated detection procedure [Landegren et al Science 241:1077 (1988)].

Oligonucleotides specific to normal or mutant sequences are chemically synthesized using commercially available machines, labelled radioactively with isotopes (such as $^{32}$P) or non-radioactively (with tags such as biotin [Ward and Langer et al. Proc. Nat. Acad. Sci. USA 78:6633–6657 (1981)], and hybridized to individual DNA samples Immobilized on membranes or other solid supports by dot-blot or transfer from gels after electrophoresis. The presence or absence of these specific sequences are visualized by methods such as autoradiography or fluorometric (Landegren et al, 1989, supra) or colorimetric reactions [Gebeyehu et al Nucleic Acids Research 15:4513–4534 (1987)]. As is appreciated by those skilled in the art, the sequence length of the oligonucleotides is sufficient to ensure hybridization of the probe. Usually the oligos of subject material are approximately 12 to 20 bp and up; for example, the specific 15-C and 17-T probes of the preferred embodiment of the invention.

Sequence differences between normal and mutants may be revealed by the direct DNA sequencing method of Church and Gilbert (supra). Cloned DNA segments may be used as probes to detect specific DNA segments. The sensitivity of this method is greatly enhanced when combined with PCR [Wrichnik et al, *Nucleic Acids Res.* 15:529–542 (1987); Wong etal, *Nature* 330:384–386 (1987); Stoflet et al, *Science* 239:491–494 (1988)]. In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Sequence alterations may occasionally generate fortuitous restriction enzyme recognition sites which are revealed by the use of appropriate enzyme digestion followed by conventional gel-blot hybridization [Southern, *J. Mol. Biol.* 98: 503 (1975)]. DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

The discovery of a unique mutation in the pig ryanodine receptor gene has uncovered that the mutation deletes a HinPI restriction enzyme site and creates a HgiAI site at nucleotide position 1843, (hereinafter referred to as site 1). HinPI digestion of the mutant sequence would not result in cleavage at nucleotide position 1843 while digestion with HgiAI would. This leads to a restriction enzyme recognition site for DNA analysis. As can be appreciated, this region of the gene may be amplified by PCR techniques. The cDNA, as shown in FIG. 2, consists of several exons, with the intron information deleted. As is appreciated by those skilled in the art, intron information to either or both sides of the exon containing position 1843 may be used in the PCR amplification of this portion of the genomic DNA. It is also possible to select a portion of the intron which would carry a clearable HinPI or HgiAI site (hereinafter referred to as site 2). Site 2 would act as a built-in control to monitor whether the conditions for each restriction endonucleous digestion were appropriate. Thus for HinPI, 100% digestion of site 2 combined with 100% digestion of site 1 would indicate homozygous normal; 100% digestion of site 2 combined with 0% digestion of site 1 would indicate homozygous MH: 100% digestion of site 2 combined with 50% digestion of site would indicate a heterozygo. Less than 100% of site 2 would require a repeat digestion. For HgiAI, 100% digestion at sites 2 and 1 would indicate homozygous 100% digestion at site 2 and 0% digestion at site 1 would indicate homozygous normal; 100% digestion at site 2 and 50% digestion at site I would indicate a heterozygate; partial digestion would require a repeat digestion.

We tested for the presence of the mutation either by oligonucleotide hybridization or by analysis of restriction endonuclease digestion patterns because the mutation deletes a HinPI site and, simultaneously, creates a HgiAI site in the porcine gens. The use of restriction endonuclease digestion as the basis for genotype analysis is superior to oligonucleotide hybridization because it is simpler, cheaper and less hazardous, and because it has the potential for greater accuracy, particularly in cases where samples are partially contaminated. We recognized the desirability, however, of improving our restriction endonuclease based test for the mutation in two ways. First, it was important to obtain a larger DNA fragment that would absorb more stain so that fragments and subfragments would be more readily visualized following gel electrophoresis. Second, since the test must differentiate digestion of one allele for heterozygotes from partial digestion of normal or MH genotypes, a "built in control" digestion site which should always be 100% digested would be an important feature of a simple but reliable test.

Our strategy in achieving these goals was to isolate and sequence intron DNA lying between the exon containing the mutation site and its two flanking exons. We then designed PCR primers that would allow amplification of fragments between 500 and 1000 bp which would contain either a constant HinPI or HgiAI site in the porcine RYRI gens which would be sufficiently distant from the polymorphic mutation site that cleavage at one or both sites could be readily detected following gel electrophoresis. The pig intron sequences flanking the exon containing the mutation site, were PCR amplified with appropriate primers within the predicted flanking porcine exons. Genomic DNA was isolated from the blood of a Yorkshire pig. The forward primer [5'-ATCTCTAGAGACAAGCATGGGAG-GAACCACAAG-3'-GACAAGCATGGGAG-GAACCACAAG-3'] corresponded to nucleotides 1771 to 1794 (SEQ ID. NO. 1, positions 7901 to 1924) while the reverse primer having the reverse complement of 5'-CATCCGCCCCAACATCTTTGTGGG-3' (SEQ ID NO. 1, positions 2058 to 2081) corresponded to nucleotides 1929 to 1952 in pig ryanodine receptor cDNA [Fujii et al., "Identification of a Mutation in the Porcine Ryanodine Receptor Associates with Malignant Hyperthermia". *Science*, 253:448–451, 1991]. Nine nucleotides constituting an *XbaI* restriction endonuclease site which facilitates subcloning can be added to the 5' end of the primer. Amplification was carried out in the PCR buffer provided by Perkin Elmer Cetus, containing 1 mM $MgCl_2$ and 100 ng each of primers, for 35 cycles using a step program of denaturation at 94° C. for 1 min, annealing at 55° C. for 2 min and extension at 72° C. for 3 min in a DNA Thermal Cycler (Perkin-Elmer Cetus). The 1.6 kbp PCR product which we obtained was digested with appropriate restriction endonucleases and subcloned into the Bluescript Vector. Sequencing of the subclones was performed on both strands as described above. The pig genomic sequence lying between the exon containing the mutation and its flanking exons is shown in FIG. 6.

Figure 7:
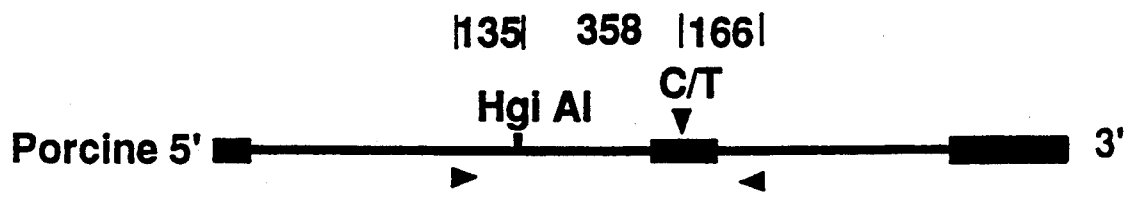
FIG. 7 - Diagrammatic representation of digestion patterns for the porcine genomic fragments obtained by PCR amplification. Thick horizontal lines represent exons, connected by thin horizontal lines representing introns. Horizontal arrows indicate location of forward and reverse primers. Vertical arrows indicate polymorphic (C/T) sequences giving rise to polymorphic restriction endonuclease sites. Thin vertical lines indicate constant restriction endonuclease sites. The sizes of the fragments resulting from digestion with HgiAI are indicated above the line representing the porcine gene.

The exon which contains the mutation site was 134 bp long. The nucleotide sequences observed at 5' donor and 3' acceptor splice sites in each of the four introns were in agreement with the consensus sequences reported previously (Breathnach and Chambon, "Organization and Expression of Eucaryotic Split Genes Coding for Proteins", *Annu. Rev. Biochem.*, 50:349–383, 1981). The mutation of the sequence GCGCTC to GTGCTC deletes a HinPI site and creates a HgiAI restriction endonuclease site in pig (Fujii et al., supra; Otsu et al., "Cosegregation of Porcine Malignant Hyperthermia and a Probable Causal Mutation in the Skeletal Muscle Ryonodine Receptor Gene in Backcross Families", *Genomics* 11 in press, 1991). In pig, a constant HgiAI site was located 358 bp upstream of the polymorphic mutation site. Accordingly, primers to be used in the MH detection assay were chosen so that the PCR products would include these sites as internal controls for restriction endonuclease digestion. Diagrammatic representation of the amplified pig PCR products is presented in FIG. 7.

A pig sequence of 659 bp between nucleotides overlined in FIG. 6 was amplified for analysis by HgiAI digestion from genomic DNA from homozygous MH, heterozygous MH and homozygous normal pigs (Fujii et al. supra). The amplification buffer contained 1 mM $MgCl_2$, 200–500 ng of pig genomic DNA and 100 ng each of the forward (5'-TCCAGTTTG-CCACAGGTCCTACCA-3') (SEQ ID NO. 3, positions 500 to 523) and reverse primers having the reverse complement of 5'-ACTCAGAGACT-CCACTCCGGTGAA-3' (SEQ ID NO. 3, positions 1134 to 1157). Amplification conditions were those defined above, except that the annealing temperature was 53° C.

Figure 8:
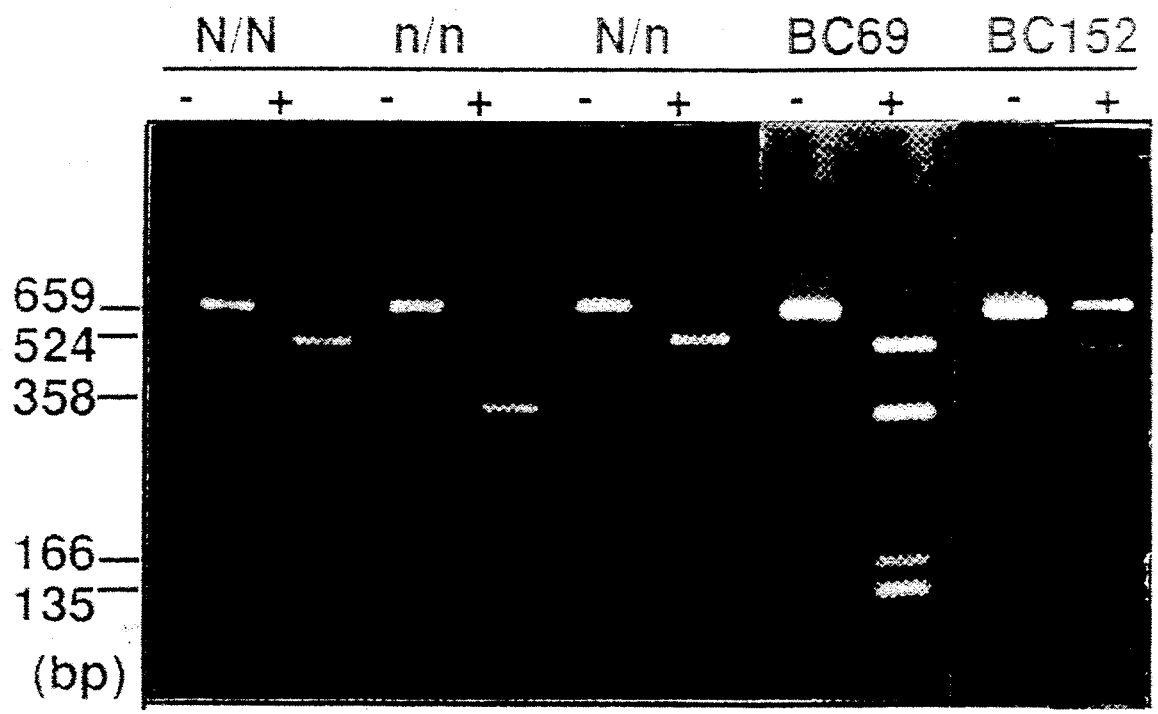
FIG. 8 - Detection of the pig C1843 to T mutation by amplification and subsequent digestion of the amplified product with HgiAI. A 659 bp PCR product was amplified from genomic DNA from N/N Yorkshire, n/n Pietrain, N/n Yorkshire x Pietrain and n/n British Landrace pigs. In each case, the first lane (−) represents the PCR amplified product, while the second lane (+) represents the same product after digestion with HgiAI. Since the mutation of C1843 to T creates a HgiAI site, digestion of the N/N genotype with HgiAI generates 524 and 135 bp fragments from the constant HgiAI site and 358, 166, 135 bp fragment from the n/n genotype, through a combination of digestion of the constant and polymorphic HgiAI sites. Fragments of 524, 358, 166 and 135 bp fragments are generated in a N/n genotype from a combination of full digestion of the constant HgiAI site and of one allele at the polymorphic HgiAI site, but no digestion of the other allele at the polymorphic HgiAI site. Note the differences in relative intensity of the four bands. In the case of BC69, 524, 358, 166 and 135 bp fragments are also generated from a pig diagnosed as n/n by halothane challenge and haplotype testing. In this case, however, contamination of the sample with N/n DNA leads to retention of some of the 524 bp band. Contamination is detected by the abnormal intensities of the various bands (compare BC69 with N/n). With BC152, we illustrate partial digestion of the 659 bp band. In this case a second, complete digestion led to diagnosis of this sample as n/n.

In FIG. 8 we illustrate the HgiAI restriction endonuclease digestion patterns derived from the 659 bp products amplified from normal (N/N), homozygous MH (n/n) and heterozygous (N/n) porcine genotypes, from DNA from a n/n individual BC69 (Otsu et al., supra) contaminated either manually or naturally (possible chimaerism; McFee et al., "An Intersex Pig with XX/YY Leucocyte Mosaicism, *Can. J. Genet Cytol.*, 8:502–505, 1966) with N/n DNA, and from n/n DNA partially digested by HgiAI. In each case, the first lane (−) represents the PCR amplified product and the second lane (+) represents the same product after digestion with HgiAI. DNA from the N/N individual gave bands of 524 and 135 bp when digested with HgiAI, while DNA from the n/n individual gave bands of 358, 166 and 135 bp, with the 166 bp band of slightly greater intensity than the 135 bp band. Digestion of DNA from the heterozygous individual gave bands of 524, 358, 166 and 135 bp. In this case, the intensity of the 358 bp band was less than that of the 524 bp band and the intensity of the 166 bp band was less than that of the 135 bp band. In sample BC69, contamination of n/n DNA with a lesser amount of N/m DNA was detectable after digestion because the 358 bp band was of about equal intensity with the 524 bp band and the 166 bp band was of only slightly lower intensity than the 135 bp band. Thus it is possible to detect contamination of samples by comparison of band intensities. With sample BC152, we illustrate a case where remnants of the 659 bp band containing the constant HgiAI site indicate incomplete digestion of a n/n DNA, requiring a repeat analysis.

While these modifications in PCR amplification and restriction endonuclease digestion make the diagnostic test for porcine MH more accurate and reliable, its adaptation to large scale testing requirements may be enhanced by the following. We have evaluated the rapid isolation of genomic DNA from porcine blood by the method of Kawasaki (1990 "Sample Preparation from Blood, Cells, and other Fluids" In: "PCR Protocols" (Innis, M. A., Gelfend, D. H., Sninsky, J. J. and White, T. J.) pp 142–152, Academic Press, N.Y.). Fifty $\mu l$ of EDTA-treated blood were added to 0.5 ml of a solution of 10 mM Tris-HCl, 0.1 mM EDTA, pH 8.0, (TE) in a 1.5 ml Eppendorf centrifuge tube and spun for 10 sec. The pellet was washed 3 times with 0.5 ml of TE by vortexing and spinning and resuspended in 100 $\mu l$ of gelatin-free Perkin Elmer Cetus PCR buffer containing 0.5% Tween 20 and 100 $\mu g/ml$ of Proteinase K. After incubation at 56° C. for 30 min to complete digestion and 10 min at 95° to inactivate the protease, 10 $\mu l$ of this solution was used for PCR amplification, as outlined above. The product was indistinguishable from the product obtained from DNA isolated conventionally (Miller et al., "A Simple Salting Out Procedure for Extracting DNA from Human Nucleated Cells", *Nucleic Acids Res.*, 16:1215, 1988).

We have also evaluated the potential of agerose rather than acrylamide gels for separation of the various fragments, since the use of horizontal agerose gels is more readily adapted to large scale analysis than the use of thin vertical acrylamide gels. We have found that the use of a 3% Nu Sieve 3:1 Agarose gel (FMC Bioproducts) in TBE buffer, pH 8.5, (Manjarls et al., "Molecular Cloning, a Laboratory Manual", Cold Spring Harbor Laboratory Press, Cold Spring Harbor, N.Y., 1982) provides adequate separation of the bands between 940 and 135 bp that are generated in these tests. These bands can be detected by staining with ethidium bromide added to the sample buffer.

These additional refinements provides a rapid, accurate, non-invasive, inexpensive, DNA based test for detection of a probable causative mutation for MH in both porcine and human genomic DNA. The test can be used for reliable, large scale screening for MH in populations of both species.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, the PCR product with the 1 bp substitution is clearly distinguishable from the normal sequence on an 8% non-denaturing polyacrylamide gel. DNA fragments of different sequence compositions may be distinguished on denaturing formamide gradient gel in which the mobilities of different DNA fragments are retarded in the gel at different positions according to their specific "partial-melting" temperatures [Myers, supra]. In addition, sequence alterations, may be detected as changes in the migration pattern of DNA heteroduplexes in non-denaturing gel electrophoresis, as have been detected for the 1 bp mutation and in other experimental systems [Nagamine et al, *Am. J. Hum. Genet*, 45:337–339 (1989)]. Alternatively, a method of detecting a mutation comprising a single base substitution or other small change could be based on differential primer length in a PCR. For example, one invariant primer could be used in addition to a primer specific for a mutation. The PCR products of the normal and mutant genes can then be differentially detected in acrylamide gels.

Sequence changes at specific locations may also be revealed by nuclease protection assays, such as RNase (Myers, supra) and S1 protection [Berk, A. J., and P. A. Sharpe, *Proc. Nat. Acad. Sci. USA*, 75:1274 (1978)], the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized [Saiki et al, *Proc. Natl. Acad. USA*, 86:6230–6234 (1989)]. A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

In summary, the screening method comprises the steps of:
  providing a biological sample of the subject to be screened; and providing an assay for detecting in the biological sample, the presence of at least a member from the group consisting of the normal porcine ryanodine receptor (RYR1), normal RYR1 products, an MH mutant RYR1, MH mutant RYR1 products and mixtures thereof.

The method may be further characterized by including at least one more nucleotide probe which is a different DNA sequence fragment of, for example, the DNA of FIG. 2, or a different DNA sequence fragment of pig chromosome 6 and located to either side of the DNA sequence of FIG. 2.

A kit, according to an embodiment of the invention, suitable for use in the screening technique and for assaying for the presence of the RYR1 gene by an immunoassay comprises:
  (a) an antibody which specifically binds to a gene product of the RYR1 gene;
  (b) reagent means for detecting the binding of the antibody to the gene product; and
  (c) the antibody and reagent means each being present in amounts effective to perform the immunoassay, The kit for assaying for the presence for the RYR1 gene may also be provided by hybridization techniques. The kit comprises:
  (a) oligonucleotide sequences for PCR priming of the appropriate porcine genomic sequence;
  (b) oligonucleotide probes which specifically bind to the RYR1 gene;
  (c) reagent means for detecting the hybridization of the oligonucleotide probes to the RYR1 gene; and
  (d) the probes and reagent means each being present in amounts effective to perform the hybridization assay.

A significant use for this invention is determining whether elimination of the defective gene might also decrease lean body mass in the various pig breeds. It is possible that there is an association between a defective RYR1 gene and lean body mass, since the hypersensitive excitation-contraction coupling, which is characteristic of MHS animals [O'Brien (1987) supra; O'Brien (1986) supra and O'Brien (1990) supra], is analogous to chronic function overload [O'Brien et al (1991) Can. J. Physol Pharmacol 69] which results in muscle hypertrophy. Furthermore, this may divert energy to Ca$^{2+}$ pumping and muscle contraction and away from fat storage. If this were the case, then it would be advantageous to reintroduce the defective RYR1 gene selectively into breeding stock. For example, crosses of MH/MH X N/N would yield F1 generation market animals which might all have superior lean body mass and acceptable meat quality [Elizondo et al (1977) J. Anim. Sci. 45:1272–1279]. The availability of the probes, according to this invention, for accurate diagnosis of breeding stocks now make such a breeding program feasible.

It is also feasible to develop polyclonal or monoclonal antibodies against the specific peptide sequences surrounding the mutation leading to MH so that these differential antibodies can be used to detect differences in normal and mutant ryanodine receptor proteins. It is likely that all MH swine will have the same or another section of the protein sequence either altered or missing. It is possible to express specific DNA sequences in biological systems [e.g. Clarke et al (1990) J. Biol. Chem. 65:17405–17408] to make either unique peptide sequences or to express the sequences from a fused gene which will make a fusion peptide. It is also possible to synthesize peptides chemically and to link them to other proteins. Any of these peptide forms can be potential antigens for the production of specific antibodies. Thus antibodies raised to the altered sequence (mutant MH) will show positive immunostaining on muscle sections in MH pigs and heterozygous pigs, since they will react with the antigen in the muscle. No staining should be observed in normal porcine individuals but antibodies raised against the normal sequence will stain normal muscle. Heterozygous pigs should be distinguished from homozygous affected pigs because they will always react with the antibody raised against the normal peptide. Similarly, these reactions could be observed with the more sensitive technique of immunoblotting [Towbin et al. (1979) Proc. Natl. Acad. Sci. USA 76:4350–4354] of extracts of muscle protein.

As mentioned, antibodies to epitopes of the porcine RYR1 protein are raised to provide extensive information on the characteristics of the protein and other valuable information which includes:

1. To enable visualization of the protein in cells and tissues in which it is expressed by immunoblotting ("Western blots") following polyacrylamide gel electrophoresis. This allows an estimation of the molecular size of the mature protein including the contribution from the cells of post-translationally added moieties including oligosaccharide chains and phosphate groups, for example. Immunocytochemical techniques including immunofluorescence and immuno-electronmicroscopy can be used to establish the subcellular localization of the protein in cell membranes. The antibodies can also be used to provide another technique in detecting any of the other RYR1 mutations in perhaps other pig breeds which result in the synthesis of a protein with an altered size.

2. Antibodies to distinct domains of the protein can be used to determine the topological arrangement of the protein in the cell membrane. This provides information on segments of the protein which are accessible to externally added modulating agents for purposes of drug therapy.

3. The structure-function relationships of portions of the protein can be examined using specific antibodies. For example, it is possible to introduce into cells antibodies recognizing each of the charged cytoplasmic loops which join the transmembrane sequences as well as portions of the nucleotide binding folds and the R-domain. The influence of these antibodies on functional parameters of the protein provide insight into cell regulatory mechanisms and potentially suggest means of modulating the activity of the defective protein in an MH pig.

4. Antibodies with the appropriate avidity also enable immunoprecipitation and immuno-affinity purification of the protein. Immunoprecipitation will facilitate characterization of synthesis and post translational modification including ATP binding and phosphorylation. Purification will be required for studies of protein structure and for reconstitution of its function, as well as protein based therapy.

It is possible to raise polyclonal antibodies specific for both fusion proteins containing portions of the RYR1 protein and peptides corresponding to short segments of its sequence. Monoclonal antibodies can be similarly raised to other domains of the RYR1 protein. It is preferred, as is appreciated by those skilled in the art, that the protein fragment should contain approximately 75 to 100 amino acids of the subject material.

As with the generation of polyclonal antibodies, immunogens for the raising of monoclonal antibodies (mAbs) to the RYR1 protein may be via bacterial fusion proteins [Smith et al, *Gene* 67:31 (1988)] containing portions of the RYR1 polypeptide or synthetic peptides corresponding to short (12 to 25 amino acids in length) segments of the sequence. The essential methodology is that of Kohler and Milsrein [*Nature* 256:495 (1975)3.

Balb/c mice are immunized by intraperitoneal injection with 500 μg of pure fusion protein or synthetic peptide in incomplete Freund's adjuvant. A second injection is given after 14 days, a third after 21 days and a fourth after 28 days. Individual animals so immunized are sacrificed one, two and four weeks following the final injection. Spleens are removed, their cells dissociated, collected and fused with Sp2/O-Ag14 myeloma cells according to Gefter et al, *Somatic Cell Genetics* 3:231 (1977). The fusion mixture is distributed in culture medium selective for the propagation of fused cells which are grown until they are about 25% confluent. At this time, culture supernatants are tested for the presence of antibodies reacting with a particular RYR1 antiten. An alkaline phosphatase labelled anti-mouse second antibody is then used for detection of positives. Cells from positive culture wells are then expanded in culture, their supernatants collected for further testing and the cells stored deep frozen in cryoprotectant-containing medium. To obtain large quantities of a mAb, producer cells are injected into the peritoneum at $5 \times 10^6$ cells per animal, and ascites fluid is obtained. Purification is by chromatography on Protein G- or Protein A-agarose according to Ey et al, *Immunochemistry* 15:429 (1977).

Reactivity of these mAbs with the RYR1 protein is confirmed by polyacrylamide gel electrophoresis of membranes isolated from epithelial cells in which it is expressed and immunoblotted [Towbin et al, *Proc. Natl. Acad. Sci. USA* 76:4350 (1979)].

In addition to the use of monoclonal antibodies specific for each of the different domains of the RYR1 protein to probe their individual functions, other mAbS, which can distinguish between the normal and mutant forms of RYR1 protein, are used to detect the mutant protein in muscle cells.

Antibodies capable of this distinction are obtained by differentially screening hybridomas from paired sets of mice immunized with a peptide fragment containing the arginine at amino acid position 615 or cystsine at amino acid position 615.

Antibodies to normal and MH versions of RYR1 protein and of segments thereof are used in diagnostically immunocytochemical and immunofluorescence light microscopy and immunoelectron microscopy to demonstrate the tissue, cellular and subcellular distribution of RYR1 within the muscle of MH pigs, carriers and non-MH individuals.

Other modes of expression in heterologous cell system also facilitate dissection of structure-function relationships. The complete RYR1 DNA sequence ligated into a plasmid expression vector is used to transfect cells so that its influence on ion fluxes in the cell can be assessed. Plasmid expression vectors containing part of the normal RYR1 sequence along with portions of modified sequence at selected sites can be used in vitro mutagenesis experiments performed in order to identify those portions of the RYRI protein which are crucial for regulatory function.

The DNA sequence can be manipulated in studies to understand the expression of the gene and its product, and, to achieve production of large quantities of the protein for functional analysis, antibody production, and pig therapy. The changes in the sequence may or may not alter the expression pattern in terms of relative quantities, tissue-specificity and functional properties. The partial or full-length cDNA sequences, which encode for the subject protein, unmodified or modified, may be ligated to bacterial expression vectors such as the pRIT [Nilsson et al. *EMBO J.* 4:1075–1080 (1985)], pGEX [Smith and Johnson, *Gene* 67: 31–40 (1988)] or pATH [Spindler et al. *J. Virol.* 49: 32–141 (1984)] plasmids which can be introduced into *E. coli* cells for production of the corresponding proteins which may be isolated in accordance with the standard protein purification procedures. The DNA sequence can also be transferred from its existing context to other cloning vehicles, such as other plasmids, bacteriophages, cosmids, animal virus, yeast artificial chromosomes (YAC) [Burke et al. *Science* 236:806–812, (1987)], somatic cells, and other simple or complex organisms, such as bacteria, fungi [Timberlake and Marshall, *Science* 244:1313–1317 (1989)], invertebrates, plants [Gasser and Fraley, *Science* 244:1293 (1989)], and pigs [Pursel et al. *Science* 244:1281–1288 (1989)].

For expression in mammalian cells, the cDNA sequence may be ligated to heterologous promoters, such as the simian virus (SV) 40, promoter in the pSV2 vector [Mulligan and Berg, *Proc. Natl. Acad. Sci USA*, 78:2072–2076 (1981)] and introduced into cells, such as monkey COS-1 cells [Gluzman, *Cell*, 23:175–182 (1981)] to achieve transient or long-term expression. The stable integration of the chimeric gene construct may be maintained in mammalian cells by biochemical selection, such as neomycin [Southern and Berg, *J. Mol. Appln. Genet.* 1:327–341 (1982)] and mycopnoenolic acid [Mulligan and Berg, supra].

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it), or a mini gene (a cDNA with an intron and its own promoter) is introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the simian virus (SV)40 or long terminal repeat (LTR) of the Rous Sarcoma virus and polyadenylation and splicing signal from SV are readily available [Mulligan et al *Proc. Natl. Acad. Sci. USA* 78:1078–2076, (1981); Gorman et al *Proc Natl. Acad. Sci USA* 79: 6777–6781 (1982)]. The level of expression of the cDNA can be manipulated with this type of vector, either by using promoters that have different activities (for example, the baculovirus pAC373 can express cDNAs at high levels in *S. frungiperda* cells [M. D. Summers and G. E. Smith in, Genetically Altered Viruses and the Environment (B. Fields, et al, eds.) vol. 22 no 319-328, Cold Spring Harbour Laboratory Press, Cold Spring Harbour, N.Y., 1985] or by using vectors that contain promoters amenable to modulation, for example the glucocorticoid-responsive promoter from the mouse mammary tumor virus [Lee et al, *Nature* 294.:228 (1982)]. The expression of the cDNA can be monitored in the recipient cells 24 to 72 hours after introduction (transient expression).

In addition, some vectors contain selectable markers [such as the gpt [Mulligan et Berg supra] or neo [Southern and Berg *J. Mol. Appln. Genet* 1:327-341 (1982)] bacterial genes that permit isolation of cells, by chemical selection, that have stable, long term expression of the vectors (and therefore the cDNA) in the recipient cell. The vectors can be maintained in the cells as episomal, freely replicating entities by using regulatory elements of viruses such as papilloma [Sarver et al *Mol. Cell Biol.* 1:486 (1981)] or Epstein-Barr (Sugden et al *Mol. Cell Biol.* 1:410 (1985)]. Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product [Alt et al. *J. Biol. Chem.* 253:1357 (1978)].

The transfer of DNA into eukaryotic, in particular human or other mammalian cells for purposes of disease study is now a conventional technique. The vectors are introduced into the recipient cells as pure DNA (transfection) by, for example, precipitation with calcium phosphate [Graham and vander Eb, *Virology* 52:466 (1973) or strontium phosphate [Brash et al *Mol. Cell Biol.* 2:2013 (1987)], electroporation [Neumann et al *EMBO J* 1:841 (1982)], lipofection [Felgner et al *Proc Natl. Acad. Sci USA* 84:7413 (1987)], DEAE dextran [McCuthan et al *J. Natl Cancer Inst.* 41:351 1968)], microinjection [Mueller et al *Cell* 15:579 1978)], protoplast fusion [Schafner, *Proc Natl. Aca. Sci USA* 72:2163] or pellet guns [Klein et al, *Nature* 327:70 (1987)]. Alternatively, the cDNA can be introduced by infection with virus vectors. Systems are developed that use, for example, retroviruses [Bernstein et al. *Genetic Engineering* 7:235, (1985)], adenoviruses [Ahmad et al *J. Virol* 57:267 (1986)] or Herpes virus [Spaere et al *Cell* 30:295 (1982)].

These eukaryotic expression systems can be used for many studies of the MH gene and the RYR1 product, not only as associates with pigs, but also to provide insight into human MHS. These include, for example: (1) determination that the gene is properly expressed and that all post-translational modifications necessary for full biological activity have been properly completed; (2) production of large amounts of the normal protein for isolation and purification (3) to use cells expressing the RYR1 protein as an assay system for antibodies generated against the RYR1 protein or an assay system to test the effectiveness of drugs, (4) study the function of the normal complete protein, specific portions of the protein, or of naturally occurring or artificially produced mutant proteins. Naturally occurring mutant proteins exist in pigs with MH while artificially produced mutant protein can be designed by site directed sequence alterations. These latter studies can probe the function of any desired amino acid residue in the protein by mutating the nucleotides coding for that amino acid.

The recombinant cloning vector, according to this invention, then comprises the selected DNA of the DNA sequences of this invention for expression in a suitable host. The DNA is operatively linked in the vector to an expression control sequence in the recombinant DNA molecule so that normal RYR1 polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli*, Pseudomonas, *Bacillus subtilis, Bacillus stearothermophilus* or other bacilli; other bacteria; yeast; fungi; insect; mouse or other animal; or plant hosts; or human tissue cells.

It is appreciated that for the mutant DNA sequence similar systems are employed to express and produce the mutant product.

The DNA sequence disclosed herein can be manipulated in order to achieve expression and production of larger quantities of the protein for functional analysis and antibody production. Partial or full length cDNA sequences, which encode porcine RYR1 may be ligated to bacterial expression vectors (for example, pRIT, pGEX, or pATH). The DNA can also be transferred from its existing context to other cloning vehicles, such as other plasmids, bacteriophages cosmids, animal virus, yeast artificial chromosomes, somatic cells, and other simple or complex organisms, such as bacteria, fungi, invertebrates, or plants. The cDNA- sequence (or portions thereof) or a mini gene can be introduced into eukaryotic expression vectors by standard techniques. The expression vectors can also be introduced into recipient cells by conventional techniques, including transfection, calcium or strontium phosphate precipitation, electroporation, microinjection, protoplast fusion, or virus vectors.

Antibodies to various epitopes of the porcine RYR1 protein can be raised to provide extensive information on the characteristics of the protein and other valuable information which can be used in immunoassays. The antibodies may be raised to fusion proteins containing defined portions of the porcine RYR1 polypeptide or may be raised to protein fragments which are prepared by chemical synthesis. As already noted, fusion proteins may be developed by expression of vectors in suitable hosts. As to the chemical synthesis of the proteins or peptides, this is well within the skill of those knowledgeable in the art.

With the purified fusion protein, which may be achieved by affinity chromatography, the protein fragments can be injected into rabbits. Sera from the rabbits immunized with the protein fragments are screened in accordance with standard techniques to raise polyclonal antibodies.

DNA sequences may also be subjected to site: directed mutagenesis for comparative functional expression studies [eg. Maruyama and MacLennan (1988) *Proc. Natl. Acad. Sci. USA* 85:3314–3318). If the nature of the human and pig mutations are different, it may be desirable to create animal models which more closely resemble each human and pig mutation. This could be achieved by site directed mutagenesis in conjunction with homologous recombination in embryonic stem cells, or by use of retrovirus vectors to create transgenic animals.

Our discovery of an altered nucleotide sequence allows us to conduct a one-step, allele-specific PCR-based diagnosis [Ballabio et al *Nature* 343:220 (1990)] of MH from pig genomic DNA. Application of the one-step, allele-specific PCR techniques to detect mutations has already been exemplified in Ballabio et al (supra). In that particular application, forward primers were selected to detect the Δ508 mutation in the cystic fibrosis gene. Each allele-specific primer had at its 3' end a sequence corresponding to the normal allele or to the ΔF508 allele. Thus in such a test, nucleotides at the 3' end of forward or reverse primers impart allele specificity to priming. Similarly, with selected primers for differential detection of the MH allele, either forward or reverse, the MH normal and mutated sequences are included towards the 3' end, as with the Ballabio et al (supra) technique.

As a second example, probes 17-C and 15-T, or modification of these probes to increase their temperature sensitivity of hybridization, could be used as forward PCR primers with appropriate reverse PCR primers selected from FIG. 2. Probe 17-C hybridizes to genomic DNA thereby permitting PCR amplification of the MHN sequence, but not the MHS sequence at temperatures near 61° C. Conversely, probe 15-T hybridizes to genomic DNA thereby permitting PCR amplification of the sequence, but not the MHN sequence, at temperatures near 55° C. Successful application of these primers, in separate reactions with the same genomic DNA, would yield one product for 17-C with MHN DNA and no product for 15-T; no product for 17-C and a product for 15-T with MHS DNA; and products for both 17-C and 15-T with heterozygous DNA. The diagnosis would be complete following gel electrophoresis and analysis of the presence or absence of a PCR product. Appropriate controls may be used in this diagnosis.

It is therefore appreciated that, in accordance with standard PCR techniques, a rapid, economical assay is provided to detect the presence of the T1843 mutation. As is appreciated, the remaining forward or reverse primer may be located elsewhere along the RYR1 gene within standard PCR amplification distances. The invention therefore contemplates any forth of PCR amplification technique where the forward or reverse primer sequence includes either the normal C1843 base the mutant T1843 and the normal surrounding RYR1 sequence as exemplified with primers 15-T and 17-C.

The 17 polymorphisms that we have discovered are potentially useful in further analysis of MH or other genetic diseases involving the ryanodine receptors (for example central core disease in humans has been linked to the RYR1 gene: J. Mulley, personal communication). Such polymorphisms can frequently be demonstrated to give rise to restriction fragment length polymorphisms (RFLPs) which have been useful in analysis of linkage between two genes, one or both of which may give rise to a disease. For example, if another, unknown mutation in the RYR1 gene should be found to give rise to MH, linkage studies using probes for the presence of one or more of the polymorphisms that we have described could provide a useful means for following the inheritance of the disease, indirectly, by the association of the inheritance of a particular benign polymorphism (haplotype) with inheritance of MH (or another disease).

The following Examples are provided to demonstrate preferred techniques for isolating the mutant RYR1 gene and use of such genetic information.

Example 1

Skeletal muscle from a homozygous MHN Yorkshire pig and from a homozygous MHS Pietrain pig was dissected immediately after sacrifice of the animal and frozen in liquid nitrogen. Poly (A)+ RNA was isolated as described earlier [MacLennan et el, *Methods Enzymol.* 96:570–575 (1983)] and cDNA was synthesized using a kit supplied by the Bethesda Research Laboratories (BRL) and cDNA libraries were constructed in λgtl0 (BRL) and λZAP (Stratagene Cloning Systems) using protocols described in their respective kits. Priming of 10 μg of MHS Pietrain strain poly(A)+ RNA for cDNA synthesis was carried out with 100 ng of each of oligo d(T)17, a 24-mer oligonucleotide complementary to human skeletal muscle ryanodine receptor nucleotides 1243–1266 [Zarzato et al supra] and 18-mer oligonucleotides complementary to rabbit skeletal muscle ryanodine receptor nucleotides 9123–9140; 4900–4917 and 3499–3516 [Takeshima et al (1990) supra]. Priming of 10 μg of the normal Yorkshire strain poly(A)+ RNA was carried out with the same set of oligonucleotide, plus 24-mer sequences complementary to human nucleotides 4000–4023, 5859–5882 and 11099–11122. Restriction endonuclease fragments from the human skeletal muscle ryanodine receptor cDNA were used as probes to screen porcine cDNA libraries as described earlier [Maniatis et al (1982) supra, Otsu et al (1990) supra], except that filter washing was at 60°. The polymerase chain reaction was used to isolate nucleotides 12502 to 12567 in MHS Pietrain breed cDNA and nucleotides −24 to 448 in MHN Yorkshire breed cDNA. Basic steps in the reaction were as described previously [Elizondo et al (1977) supra] except that the first strand was synthesized from 1 μg of poly(A)+ RNA from either Pietrain or Yorkshire breed muscle using 5 ng of random primers (Pharmacia). The PCR reaction was carried out with 1/500 of the initial cDNA, using 24-mer oligonucleotide primers based on nucleotides 12400–12423 and 12613–12636 (FIG. 2) for the Pietrain breed amplification and nucleotides −24 to −1 and 597–620 for the Yorkshire breed amplification. The reaction was carried out for 35 cycles in a DNA Thermal Cycler® (Perkin-Elmer Cetus) in 100 μl of the Gene Amp® kit (Perkin-Elmer Cetus) using a step program of annealing at 52° for 2 min; extension at 72° for 3 min and denaturation at 95° for 40 sec with a final cycle of 74 min for extension. cDNA was subcloned into the Bluescript Vector® (Stratagene) for single errand, dideoxy sequence [Sanger et al *Proc. Natl. Acad. Sci. USA* 74:5463–5467 (1977)] analysis using the T7 sequencing kit (Pharmacia). Five independent PCR products were sequenced for detection of potential artifactual sequences.

Example 2

Genomic DNA was isolated from fresh pig blood or frozen pig muscle [Miller et al *Nucleic Acids Res.* 16:1215 (1988)]. A specific region, of 74 bp lying between residues 1811 and 1884 (see overlined sequences in FIG. 2 which identify the PCR primers used in this reaction) was PCR amplified from 2–5 µg of genomic DNA using 100 ng of each primer. The forward primer used in PCR amplification was synthesized by Kronem (Mississauca) and was of the composition 5'-GTTCCCTGTGTGTGTGCAATGGTG-3', corresponding to nucleotides 1811 to 1834 in FIG. 2 (SEQ ID NO. 1, positions 1940 to 1963). The reverse primer was one having the reverse complement of 5'-ATTACT-GAGAACTTGCTCCCTGGC-3' (SEQ ID NO. 1, positions 1990 to 2013) being the reverse complement of nucleotides 1861 to 1884 in FIG. 2. Nine nucleotides which constitute an Xba restriction endonuclease can be added to the 5' end of the primer for ease of subcloning, but this is not a prerequisite for this study. These nine nucleotides can conveniently be left out of future studies. The primers were annealed at 52° for 2 min, extended at 72° for 3 min and denatured at 95° for 40 sec with a final cycle of 7 min for extension in a DNA thermal cycler (Perkin-Elmer Cetus). Part of the PCR product was separated by electrophoresis to assure that synthesis had occurred. An aliquot of 20 µl was incubated for 30 min at 65° with 380 µl of 0.3M NaoH and 30 mM EDTA, neutralized with 400 µl of 2M $NH_4 Ac$ and 400 µl was applied in duplicate to BA85 nitrocellulose filters using a Minifold II Slot Blot ® apparatus (Schleicher and Schuell, Dassel, FGR). The filters were baked for 2 hours at 80° and prehybridized for 2 hours at 45° in a solution of 6×SSC, 1×Denbarr's solution and 0.1% SDS. They were then separated and hybridized in separate containers with 300 ng of either oligonucleotide probe 17-C or 15-T, in 30–50 ml of 6×SSC, 1×Denharts solution and 0.1% SDS at 45° for 4 hours. Oligonucleotide probes were end labelled with $^{32}P$ using [$^{32}P$]ATP and $T_4$ polynucleotide kinase [Maniatis et al (1982) supra]. Filters were washed with shaking 6 times with 50 ml of 6×SSC and 0.1% SDS over the course of 30 min and with 500 ml of the same solution at 61° (probe 17-C) and 55° (probe 15-T) for 20 min. They were then exposed to x-ray film for 1 to 14 hours and diagnosis was made on the basis of differential probe binding. Diagnoses for many of the animals were compared with diagnoses made by standard techniques as outlined below.

Pietrain and Yorkshire swine were obtained from closed herds inbred for more than ten years, and maintained at the Ontario Veterinary College, University of Guelph [O'Brien (1990) supra; O'Brien (1991) supra and MacLennan (1983) supra]. All of the Pietrain and none of the Yorkshire breeding stock in these herds were shown to be positive for the halothane challenge test [O'Brien (1990) supra and Sanger 1977) supra] or to produce offspring that were positive for this test. The frequency of halothane reactors in Ontario Yorkshire swine from which our herd was derived was 0.0078 [Miller (1988) supra]. The test apparently detects more than 90% of MM homozygotes and less than 25% of MH heterozygotes. Based on this test, our Pietrain swine were considered to be homozygous for the MM defect, whereas our Yorkshire herd was considered to be free of homozygotes for the MH defect. MM susceptibility status was verified by the halothane and caffeine contracture tests [O'Brien (1990) supra] and O'Brien (1990) supra], performed on gracilis muscle from 11 individuals from our Yorkshire herd and 25 of our Pietrains. If the caffeine concentration producing a 1 gram increase in tension (CSC) was less than 4 mM if the muscle developed more than 0.5 g tension with exposure to 5% halothane, swine were considered to be MH-susceptible. If the CSC was greater than 7 mM and halothane produced less than 0.2 g increase in tension, swine were considered to be normal. All pietrain swine were considered to be positive, 9 Yorkshires were considered to be positive and 2 Yorkshires with CSC between 5 and 6 were considered to be possible MH heterozygotes. The gene frequency predicted by contracture test results was identical to that predicted by halothane-testing of Ontario Yorkshire swine [Miller (1988) supra]. Microassays for hypersensitivity of the $Ca^{2+}$-release channel were performed on passively-loaded terminal cisternae-enriched preparation isolated from longissimus dorsi muscle of six MH Pietrain and six normal Yorkshire swine [O'Brien (1986) supra and O'Brien (1990) supra]. Compared to normal Yorkshires $Ca^{2+}$-release for the MH Pietrain swine occurred at tenfold lower concentration of channel agohist. At similar concentrations of agohist, $Ca^{2+}$-release occurred at three fold faster and in fourfold larger amounts. In order to obtain heterozygotes for the MH gene, Pietrain were cross-bred to halothane-resistant Yorkshire swine, and halothane-reactive Landrace were cross-bred to halothane-resistant Landrace swine. Swine derived from the latter cross were shown to be halothane-resistant, although parentage studies indicated that they were carriers of the MH gene. The DNA-probe test was also performed on the halothane-reactive offspring derived from corss-breeding halothane-reactive Landrace. These were considered to be likely homozygotes, but a heterozygous state could not be ruled out. Swine that were either homozygous or heterozygous for the MH gene were considered to be MHS. Blood was also collected and analyzed from randomly selected swine from two Duroc herds that had each produce one or two halothane-reactive pigs.

Example 3

Genomic DNA was isolated from fresh pig blood or frozen pig muscle [S. A. Miller, D. D. Dykes, H. F. Polesky, Nucleic Acids Res. 16, 1215 (1988)]. For analysis of the nucleotide 1843 mutation, a 74 bp sequence was amplified with 100 ng of the forward primer 5'-GTTCCCTGTGTGTGTGCAATGGTG-3' (SEQ ID No. 1, positions 1940 to 1963), which corresponds to porcine RYR1 cDNA nucleotides 1811 to 1834 and 100 ng of the reverse primer having the reverse complement of 5'-ATTACTGAGAACTTGCTCCCTGGC-3' (SEQ ID No. 1, positions 1990–2013) corresponding to the reverse complement to RYRI cDNA nucleotides 1861 to 1884. For analysis of the Ban II polymorphism at nucleotide 4332 a 160 bp sequence was PCR amplified with the forward primer 5'-TACTAT-TACTCGGTGAGGGTCTTC-3 (SEQ ID No. 1, positions 4426–4449) which corresponds to RYRI cDNA nucleotides 4297 to 4320 and the reverse primer having the reverse complement of 5'-ATGAGCAGG-GCAACATCCACAGCA-3' (SEQ ID No. 1, positions 4562 to 4585) corresponding to the reverse complement to RYR1 cDNA nucleotides 4433 to 4456. For analysis of the Rsa I polymorphism at nucleotide 13879 a sequence of 227 bp was PCR amplified with the forward primer 5'-ATGACATGGAGGGTTCAGCAGCCG-3' (SEQ ID No. 1, positions 13892 to 13915), which corresponds to RYR1 cDNA nucleotides 13763 to 13786 and the reverse primer having the reverse complement of 5'-ATCATAGGCTACAACTGCCT-CAAG-3' (SEQ ID No. 1, positions 14095 to 14118) corresponding to the reverse complement to RYR1 cDNA nucleotides 13966 to 13989. The primers were annealed at 52° for 2 min, extended at 72° for 3 min and denatured at 95° for 40 sec for 35 cycles, with a final cycle of 7 min for extension in a DNA thermal cycler (Perkin-Elmer Cetus). The $Mg^{2+}$ concentration was 1.5 mM for amplification of the mutant sequence and 1 mM for amplification of the Ban II and Rsa I sequences in the PCR reaction buffer provided by Perkin-Elmer Cetus. For hybridization analysis of the MH mutation, 50–100 ng of DNA were applied in duplicate to BA85 nitrocellulose filters using a Minifold II Slot Blot apparatus (Schleicher and Schuell, Dassel, FRG) according to the manufacturer. Prehybridization and hybridization with the 17 nucleotide sequence 5'-TGGCCGTGCGCTCCAAC-3' (SEQ ID No. 2, positions 25 to 41) (probe 17-C) and the 15 nucleotide sequence 5'-GGCCGTGTGCTCCKA-3' (SEQ ID No. 2, positions 26 to 41 with a substitution of T at base pair position 33) (probe 15-T), end labelled with $^{22}P$, were at 45° in 6×SSC, 1×Denbarr's solution and 0.1% SDS. Filters were washed with shaking six times with 50 ml of 6×SSC and 0.1% SDS over the course of 30 min and once with 500 ml of the same solution at 61° (probe 17-C) and 55° (probe 15-T) for 20 min. After exposure to x-ray film, diagnosis was made on the basis of differential probe binding. Digestion of the PCR products with Hin PI, Ban II or Rsa I were carried out using standard protocols. Sequence analysis of 3–8 subcloned 74 bp PCR products from each of heterozygous Yorkshire, Poland China, Duroc and Landrace individuals confirmed the presence of the C at position 1843 to T in each breed and its absence in a homozygous normal Hampshire animal.

MHS Pietrain and MHN Yorkshire were crossbred to produce heterozygotes. All MHN Yorkshires used in these experiments had been shown to be negative for the halothane challenge test and to produce negative offspring. In the halothane challenge test, 2 to 3 month old pigs are physically restrained and forced to inhale 3% to 5% halothane in oxygen for several minutes [O'Brien et al (1990) supra]. Those developing extensor muscle rigidity are considered MHS. This test detects more than 90% of MH homozygotes and less than 25% of MH heterozygotes. MHS Landrace and MHN Landrace were also cross-bred to produce heterozygotes. All other swine samples were obtained from local herds. Thirteen Landrace swine were studied; eight were positive for the halothane challenge test and five were offspring of swing positive for the halothane challenge test. Blood was collected from randomly selected swine from two Duroc herds that had each produced pigs that had a positive halothane test. All Pietrain swine and no Yorkshire swine in these herds were positive for the halothane challenge test. Susceptibility status of 25 Pietrain and 15 Yorkshire swine was confirmed by the caffeine-halothane contracture test [O'Brien et al (1990) supra and Miller et al (1988) supra], in which muscle was excised, placed in oxygenated physiological saline and connected to a force-displacement strain gauge. Isometric tension was recorded on a polygraph during exposure to progressively increasing amounts of caffeine or to 5% halothane. If the caffeine concentration producing a 1 gram increase in tension was less than 4 mM or if the muscle developed more than 0.5 g tension with exposure to halothane swine were considered to be MHS. All Pietrain pigs were positive for these tests, but 13 of 15 Yorkshire pigs developed 1 g contracture only at concentrations greater than 7 mM, while two had values intermediate to those of the other Yorkshires and the Pietrains. These were considered to be possible MH heterozygotes.

Swine were also tested for $Ca^{2+}$ release channel activity [O'Brien et al (1990) supra]. A terminal cisternae-enriched fraction was passively loaded with $^{45}Ca^{2+}$ and rates and amounts of release were determined at different concentrations of caffeine using a positive-pressure ultrafiltration system and scintillometry. $Ca^{2+}$ release for the MHS Pietrain swine occurred at 10-fold lower concentrations of channel agonist, at threefold faster rates and in a fourfold larger amounts than for the MHN swine.

Example 4

Preparation of Blood Samples for PCR

Detection of C1843 to T mutation is detected in accordance with the following by digestion of amplified DNA with HgiA1 restriction endonuclease.

This procedure dissolves the cytoplasmic membrane and pellets nuclei. Therefore cytoplasmic DNA is lost. Should yield about 20 ug of DNA. The procedure depends on osmotic lysis of cells & pelleting of nuclei & cell debris. Hemoglobin released from RBC's is washed away in several pelleting & washing steps. The hemoglobin is inhibitory of PCR at concentrations as low as 0.8 uM hematin or at less than 1% blood.

1) Mix 500 uL blood with 500 uL "lysis buffer" (see below) in a 1.5 mL Eppendorf microcentrifuge tube.
2) Centrifuge 13,000 g for 10 sec using Eppendorf table-top microcentrifuge Model #5415
3) Remove supernatant with piper and resuspend pellet using vortex mixer in 1 mL "lysis buffer".
4) Repeat steps 2 and 3 twice. Repeat an additional time if the pellet is still red (This happens with an occasional sample).
5) Centrifuge 13,000 g for 20 sec, remove supernatant and resuspend in 200 uL of "PCR buffer with non-ionic detergents and Proteinass K". This should yield a genomic DNA concentration of 0.1 ug/uL.
6) Incubate at 50° to 60° C. for 1 hour.
7) Incubate at 95° C. for 10 min to inactivate Proteinase K to prevent its degradation of enzymes used in PCR.
8) Store frozen if required at −85° C.
9) Up to 50% of the PCR medium may be this digested lysate.

"Lysis buffer" (from Buffone, GJ & Darlington GJ (1985) Clin Chem 30(1):164–5)
320 mM sucrose [MW=342.3 g/mol; use 109.54 g/L)
10 mM Tris-HCl(pH 7.5) [MW=121.14 g/mol; use 1.2114 g/L]   5 mM $MgCl_2$ [MW=95.21 g/mol; use 0.4761 g/L] 1% (w/v) Triton X-100; use 10 mL/L
"PCR buffer with non-ionic detergents & proteinase K"
50 mM KCl
10 mM Tris-HCl(pH 8.3)
2.5 mM $MgCl_2$
0.1 mg/mL of gelatin
0.45% (w/v) NP40

0.45% (w/v) Tween 20

Autoclave & store frozen. When ready to use, thaw & add 6 uL of 10 mg/mL Proteinase K (in water) per 200 uL of PCR buffer solution.

PCR AMPLIFICATION

1). Prepare the reagents (1 through 10) in one large "mastermix" with enough volume to perform PCR for all samples and standards; then add this mastermix to each PCR tube.

| Order of addition of reagents: | |
|---|---|
| 1. sterile distilled water (brings final vol to 25 uL when consider 11.5 uL added previously) | 6.775 uL |
| 2. 10x PCR buffer II | 2.5 uL |
| 3. 10 mM dATP | 0.5 uL |
| 4. 10 mM dCTP | 0.5 uL |
| 5. 10 mM dGTP | 0.5 uL |
| 6. 10 mM dTTP | 0.5 uL |
| 7. Primer FL17F(orward) | 0.20 uL |
| 8. Primer FL17R(everse) | 0.20 uL |
| 9. 25 mM MgCl$_2$ | 1.5 uL |
| 10. AmpliTaq DNA polymerase (5 U/uL; comes in solution at this conc) preparing a mastermix reduces the vol of work & improves precision & reduces intersample variability the same pipette tip can be used to add the mastermix but separate autoclaved pipette tips must be used for each of the genomic DNA samples in order to prevent cross-contamination | 0.125 uL |
| 11. genomic DNA (conc is approx 0.2 ug/uL) | 1 uL |

2) After addition of sample's genomic DNA to mastermix then cap the reaction tubes.

3) Start 2-step PCR

Place tray of tubes in sample block of PCR machine. Access main menu of PCR machine and use the following parameters; 1: 94° C. for 10 sec, 67° C. for 80 sec, 30 cycles, 25 uL reaction volume 4. Notes:

kits can be purchased from Perkin Elmer Cetus with all reagents necessary for PCR: we have been using the "GeneAmp PCR Core Reagent" kit cat #N808-0009 which has the dNTP's, polylnerase, 10× PCR buffer, MgCl$_2$ add polymerase last since it is heat-sensitive deoxynucleotides are dissolved in glass-distilled water & titrated to pH 7.0 with NaOH; their concentrations must be balanced since if one is hiqher then the others the polymerase may incorporate them, slow down & terminate high concentrations of primer (>0.2 uM) can lead to amplification of non-target segments (if so try reducing primer levels)

for a standard 100 uL reaction containing 2.5 units of Taq polymerase, substrate excess conditions begin to occur around 1 ug DNA (3 nmol of dNMP)

forward primer is 5'-TCCAGTTTGCCACAGGTC-CTACCA-3' (SEQ ID No. 3, positions 500 to 523)

reverse primer is 5'-TTCACCGGAGT-GGAGTCTCTGAGT-3' reverse primer is the reverse complement of 5'-ACTCAGAGACT-CCACTCCGGTGAA-3' (SEQ ID No. 3, positions 1134 to 1157)

Note that the 3' ends of the primers overlap with the result that "autoprimerization" occurs leading to dimerization and "dimer-dimerization" ie extra bands corresponding to 2×MW of primers and 4×MW of primers; this artefact can be eliminated by increasing or decreasing the length of the primers by 1 nucleotide 100 ng of ea primer is used per 100 uL; primer conc between 0.1 & 0.5 uM are generally optimal; higher primer concentrations may promote mispriming & accumulation of nonspecific product & may increase the probability of generating a template-independent artifact termed primer-dimer; nonspecific products & primer-dimer artifacts are themselves substrates for PCR & compete with the desired product for enzyme, dNTP's & primers, resulting in a lower yield of the desired product for old PCR machine (DNA Thermal Cycler from Perkin Elmer Cetus) we have successfully used 94 C. for 60 sec, 50 C. for 120 sec & 72 C. for 180 sec for 3 step PCR we have successfully used: 94 C. for sec for template melting; 53 C. for 120 sec for annealing, and 72 C. for 60 sec for extending; 35 cycles the ramp time is the time taken to change from one temperature to another.

10× PCR buffer II 500 mM KCl 100 m/M Tris-HCl pH 8.3 at room temp

Provides preferred pH & ionic strength for PCR. Gelatin free. Component of Perkin-Elmer Cetus GeneAmp PCR core Reagent kit AmpliTaq DNA polymerase purchased from Perkin Elmer Cetus this is the recombinant form of Tag DNA polymerass; it is obtained by expressing the Tag DNA polymerass gens in an *E coli* host 5). 3 phases to PCR amplification:

1) template melting:

here the doubled-stranded DNA is heat-denatured; typical denaturation conditions are 95 C. for 30 sec or 97 for 15 sec;

AmpliTaq DNA polymerase has a half-life <35 min at >95 C.; 5 min at 97.5 C. but >2 h at 92.5 C.;

it is very important in the early cycles to be sure to completely melt the template DNA;

incomplete denaturation allows the DNA to "snap back" & thus reduces product yield whereas denaturation steps that are too high &/or too long lead to unnecessary loss of enzyme activity;

when genomic DNA is used as the starting template, melting at 97 C. for the first few cycles will ensure single stranded templates for the PCR reaction; the melting temperature can be reduced for the later cycles because the smaller PCR product usually melts completely at a lower temperature (unless PCR product is excessively G+C rich) than the starting genomic DNA.

2) annealing:

here the 2 primers complementary to the 3' boundaries of the target segments are annealed at a low temperature;

higher annealing temperatures (45–65 C.) generally results in a much more specific product.

3) extension:

here the annealed primers are extended by AmpliTaq DNA polymerase at an intermediate temperature; extension is from 5' to 3';

AmpliTaq DNA polymerase extends at 2000–4000 bases per minute at 70–80 C.; thus actually need much less than one min for extending 1 kilobase;

using a 2 temperature cycle decreases cycling time while still maintaining specificity & the level of amplification;

in 2 step PCR the extension time is eliminated completely for small target sequences since the polymerase retains significant activities at lower temperatures & complete extension occurs during the thermal transition from annealing to denaturation 4) cycles:

the optimum number of cycles depends mainly on the starting conc of target DNA when other parameters are optimized; a common mistake is to execute too many cycles; too many cycles can increase the amount & complexity of nonspecific background products whereas too few cycles gives low yield; use 25-30 cycles for 300,000 target molecules, 30-35 for 15,000 targets, 35 to 40 for 1,000 targets & 40-45 for 50 targets;

pigs normally have at least 10,000 WBC's per uL of blood; assuming each has a copy of the RYR gene and that yield is 1% (very conservative) then for a 500 uL blood sample of which 10% of its lysate is used for PCR. there should be at least 5,000 targets, thus 35 cycles is appropriate: if yield is higher (say 10%, not unlikely) then 30 cycles may suffice.

PCR Product Digestion (in a total volume of 33.3 uL)

| | |
|---|---|
| 1) 10x NE buffer 3 (supplied with re) <br> 1M NaCl <br> 500 mM Tris-HCl <br> 100 mM MgCl$_2$ <br> 10 mM DTT <br> pH 7.9 at 25C | 2.83 |
| 2) HgiAI (5 U/uL) <br> New Eng BioLabs cat # 170L stored at −85 C. <br> 1 U = 1 ug lambda DNA digested at 37 C. in 50 uL assay buffer in 1 hour | 0.5 |
| 3) PCR product | 25 | add the buffer and HgiA1 directly to the PCR microreaction tubes then digest at 37 C. for 1 in the PCR machine AGE: Gel Preparation for 1 large gel

| | |
|---|---|
| 1) 1x TBE buffer <br> 89 mM Tris base <br> 89 mM boric acid <br> 2mM EDTA <br> pH 8.0 | 350 mL |
| 2) NuSieve 3:1 Agarose | 9 g |
| 3) 10 mg/mL ethidium bromide | 35 uL | bring to boil on hot plate with stirrer cool to 55° C. then pour into tray and allow to gel which takes approx 30 min when gelled if not going to use for a while cover with a thin film of TBE 8) AGE: Electrophoresis add 5 uL of loading buffer (see below) to each PCR digest to bring final volume to 25 uL add entire volume (33.3 uL) to each well of gel use up to 3 of the 36-toothed combs for the large horizontal electrophoresis apparatus (Hoefer Scientific Instruments; HE100 SuperSub Horizontal Unit)

add 10 uL for standard DNA digest for both large and small gels perform constant voltage electrophoresis:

minigel 150 volts for 1 h large gel 250 volts for 1.5 h with cold (4° C.) water circulation for controls run: homozygous PSS pig (Pietrain)

homozygous normal pig (Yorkshire)

heterozygous pig (from previous diagnosis)

uncut PCR product (from fresh sample) DNA std run a set of controls for each comb

| Loading buffer Preparation For 50 mL | |
|---|---|
| 25% Ficoll 400 | 12.5 g |
| 25 mM EDTA | 1.25 mL of 1M EDTA |
| 1% SDS | 0.5 g |
| 1 mg % Bromphenol blue | 1 mg Sigma cat #B-6131 |

9) AGE: RFLP Visualization & Photography we find the best procedure is to destain for 1 hour in warm tap water and then photograph; this gives best resolution of banding; too prolonged destaining results in the bands being less visible;

stain with 0.1 mg % ethidium bromide in water (20 uL of 10 mg/mL in 200 mL water) for 15 min; some protocols (eg HSI SuperSub manual) recommend staining with 50 mg% for 10 min; pour the stain into the gel tray;

rinse 2 times in distilled water; 15 min is recommended for each rinse; we have found that rinsing for 1 h removes most of interfering background fluorescence;

DNA is visualized by fluorescence of intercalated ethidium bromide which absorbs light at 260, 302 or 360 nm & emits at 590 nm; lower illumination wavelengths give a higher sensitivity but also increase the risk of damaging the DNA molecule; 302 is recommended for nigh sensitivity without too much damage to the DNA fragments; the dye has poor affinity for single stranded DNA;

visualize banding pattern on transilluminator (Hoelet Scientific Instruments; Mighty Bright model) inside of "The Benchtop Darkroom";

the running trays of the SuperSub are UV transparent; trays can be placed directly on top of the illuminator to reveal fluorscent bands; however maximum fluorescence is seen when the gel is placed directly on the transilluminator surface; with photography it is possible to detect as little as 1-10 ng DNA photograph with Polaroid camera;

10) Banding patterns:

1) standard: phi X-174-RF DNA from Has III digest; concentration is 500 ug/mL; stored at −85 C. in 10 mM tris-HCl(pH 7.5) with 1 mM EDTA; phi X-174-RF DNA was isolated from E coli infected with phi X am3cs70 and digested to completion with Hae III; purchase from Pharmacia: cat #27-4044; there are 11 fragments: #1-1358; 2-1078; 3-872; 4-603; 5-310; 6b-281; 61-271; 7-234; 8-194; 9-118; 10-72

2) homozygous PSS: bright band at 358 bp & faint bands at 166 bp, 135 bp (faintest band)

3) homozygous normal: bright band at 524 bp with faint band at 135 bp 4) heterozygote: bright bands at both 524 and 358 bp with lightly fluorescing bands at both 166 (faintest) & 135

5) uncut PCR product: 659 bp 6) primer dimer dimer: 96 bp 7) primer dimer: 48 bp 8) primer: 24 bp

What is claimed is:

1. A method for screening a pig to determine if said pig is susceptible to malignant hyperthermia comprising:
    i) providing a biological sample which was removed from said pig to be screened, and
    ii) conducting a biological assay to determine presence in said biological sample of mutant RYR1 gene having a nucleotide mutation of C1843 to T1843 in the DNA sequence of FIG. 2.

2. A method of claim 1 wherein said biological sample includes at least part of a genome of said pig, said part including at least a portion of a nucleic acid sequence of the normal or mutant RYR1 gene represented by said DNA sequence of FIG. 2 or FIG. 6, said portion of said nucleic acid sequence including either the C1843 or T1843 nucleotide of the DNA sequence of FIG. 2.

3. A method of claim 2 wherein said assay comprises a DNA hybridization assay in which a labelled DNA probe is used, said probe having a sequence of at least 12 consecutive nucleotides of said DNA sequence of FIG. 2 and containing either the C1843 or T1843 nucleotide.

4. A method of claim 2 wherein said assay comprises a one step, allele specific, PCR-based diagnosis of the DNA sequence in said biological sample, said assay comprising a PCR amplification of DNA in said biological sample by use of forward and reverse primer oligonucleotide sequences, said forward primer sequence having at its 3' end a C1843 base or its complement for specific detection of a normal RYR1 gene or said forward primer having at its 3' end a T1843 base or its complement for specific detection of a mutant RYR1 gene and wherein the remaining sequence of said selected forward primers and all of said reverse primers comprise a DNA sequence of consecutive nucleotides of a portion of said DNA sequence to either side of nucleotide 1843 of FIG. 2.

5. A method of claim 2 wherein said assay comprises restriction endonuclease digestion of said nucleic acid sequence fragments of said genome part in said biological sample, said fragments having been amplified to facilitate detection, said digestion comprising use of an enzyme selected from the group of enzymes for digesting said fragments at enzyme digestion sites which are cleaved by enzymes HinP1 and HgiA1, detecting either said HinP1 or HgiA1 site in said amplified DNA fragment cleaved by selected enzyme cleavage at said HinP1 site being indicative of normal RYR1 gene and cleavage at said HgiA1 site being indicative of mutant RYR1 gene.

6. A method of claim 3 wherein said DNA probes are selected from the group consisting of (17-c) 5'-TGGCCGTGCGCTCCAAC-3' (nucleotide positions 1835 to 1851 of SEQ ID No. 1) and (15-t) 5'-GGCCGTGTGCTCCAA-3' (nucleotide positions 1836 to 1850 of SEQ ID No. 1).

7. A method of claim 2 wherein said assay comprises PCR amplification of DNA in said biological sample by use of forward and reverse primer oligonucleotide sequences, each of said selected forward or reverse primer sequence comprises a consecutive nucleotide sequence of a portion of said DNA sequence to either side of nucleotide 1843 of FIG. 2 or FIG. 6, said forward and reverse primers being on opposite sides of said nucleotide 1843 to permit amplification of said biological sample DNA containing said nucleotide at position 1843 of FIG. 2.

8. A method of claim 7 wherein said forward and reverse primers are selected from the group of sets of primer sequences consisting of:
a) i) a forward primer sequence having nucleotide positions 1771 to 1794 of FIG. 2 (SEQ ID No. 1);
ii) a reverse primer sequence having the reverse complement of nucleotide positions 1929 to 1952 of FIG. 2 (SEQ ID No. 1);
b) i) a forward primer sequence having the intron sequence of FIG. 6: 5'-TCCAGTTTG-CCACAGGTCCTACCA-3' (SEQ ID No. 3—positions 520 to 523);
ii) a reverse primer sequence having the reverse complement of the intron sequence of FIG. 6: 5'-ACTCAGAGACTCCACTCCGGTGAA-3' (SEQ ID No. 3—positions 1134 to 1157);
c) i) a forward primer sequence having nucleotide positions 1811 to 1834 of FIG. 2 (SEQ ID No. 1);
ii) a reverse primer sequence having the reverse complement of nucleotide positions 1861 to 1884 of FIG. 2 (SEQ ID No. 1).

9. A method of claim 5 wherein said DNA fragment is amplified by PRC and forward and reverse primers selected for such amplification of DNA are selected from the group consisting of:
a) i) a forward primer sequence having nucleotide positions 1771 to 1794 of FIG. 2 (SEQ ID No. 1);
ii) a reverse primer sequence having the reverse complement of nucleotide positions 1929 to 1952 of FIG. 2 (SEQ ID No. 1);
b) i) a forward primer sequence having the sequence: 5'-TCCAGTTTGCCACAGGTCCTACCA-3' (SEQ ID No. 3—positions 520 to 523);
ii) a reverse primer sequence having the reverse complement of the sequence: 5'-ACTCAGAGACTCCACTCCGGTGAA-3' (SEQ ID No. 3—positions 1134 to 1157);
c) i) a forward primer sequence having nucleotide positions 1811 to 1834 of FIG. 2 (SEQ ID No. 1);
ii) a reverse primer sequence having the reverse complement of nucleotide positions 1861 to 1884 of FIG. 2 (SEQ ID No. 1).

* * * * *

UNITED STATES PATENT AND TRADEMARK OFFICE
CERTIFICATE OF CORRECTION

PATENT NO. : 5,358,649
DATED : October 25, 1994
INVENTOR(S) : MacLennan et al.

It is certified that error appears in the above-identified patent and that said Letters Patent is hereby corrected as shown below:

On the cover page, "13 Drawing Sheets" should be --17 Drawing Sheets--.

Col. 2, line 8, after "in" insert --MHS--.

Col. 4, line 8, "367" should be --36--.

Col. 4, lines 11 and 16, "homoconcentration" should be --hemoconcentration--.

Col. 6, line 2, "gone" should be --gene--.

Col. 6, line 25, after "equivalents" insert --is--.

Col. 7, line 9, after "of" insert --MHN--.

Col. 10, line 21, before "Yorkshire" insert --MHN--.

Col. 12, line 59, "aen-" should be --gen- --.

Col. 12, line 64, "oholine" should be --choline--.

Col. 13, line 1, after "the" insert --MH--.

Col. 13, line 11, after "for" insert --MH--.

Col. 13, line 17, after "deferring" insert --MH--.

Col. 13, line 22, "27" should be --37--.

UNITED STATES PATENT AND TRADEMARK OFFICE
CERTIFICATE OF CORRECTION

PATENT NO. : 5,358,649

DATED : October 25, 1994

INVENTOR(S) : MacLennan et al.

It is certified that error appears in the above-identified patent and that said Letters Patent is hereby corrected as shown below:

Col. 13, line 50, "= P" should be --$^{32}$P--.

Col. 14, line 14, after "homozygous" (first occurrence), insert --MHS--.

Col. 14, line 27, "phenotyloic" should be --phenotypic--.

Col. 15, line 13, "Biocnem." should be --Biochem.--.

Col. 15, line 13, after "93:53" insert -- (1990)--.

Col. 15, line 32, "De" should be --be--.

Col. 17, lines 21 and 22, "MM" should be --MH--.

Col. 18, line 5, "p1" should be --P1--.

Col. 18, line 14, "gens" should be --gene--.

Col. 18, line 21, "gens" should be --gene--.

Col. 19, lines 43-45, "(GCGC to GTGC)" should be --(G<u>C</u>GC to G<u>T</u>GC)--; "(GAACCC to GAGCCC)" should be --(GA<u>A</u>CCC to GA<u>G</u>CCC); and "(GTAC to ATAC)" should be --(<u>G</u>TAC to <u>A</u>TAC)--.

UNITED STATES PATENT AND TRADEMARK OFFICE
CERTIFICATE OF CORRECTION

PATENT NO. : 5,358,649  Page 3 of 6
DATED : October 25, 1994
INVENTOR(S) : MacLennan et al.

It is certified that error appears in the above-identified patent and that said Letters Patent is hereby corrected as shown below:

Col. 19, line 51, "3 orientation" should be --3' orientation--.

Col. 20, line 8, "gens" should be --gene--.

Col. 21, line 42, "clearable" should be --cleavable--.

Col. 21, line 51, after "site" insert --1--.

Col. 21, line 56, "site I" should be --site 1--.

Col. 22, line 18, "RYRI gens" should be --RYR1 gene--.

Col. 22, lines 27-28, omit "-GACAAGCATGGGAGGAACCACAAG-3'" (duplicate).

Col. 22, line 29, "7901" should be --1901--.

Col. 23, line 41, "N/m" should be --N/n---.

Col. 23, line 58, "Gelfend" should be --Gelfand--.

Col. 24, line 13, "Manjarls" should be --Maniatis--.

Col. 25, line 68, "MH" should be --MHS--

Col. 26, line 3, "65" should be --265--.

UNITED STATES PATENT AND TRADEMARK OFFICE
CERTIFICATE OF CORRECTION

PATENT NO. : 5,358,649

DATED : October 25, 1994

INVENTOR(S) : MacLennan et al.

It is certified that error appears in the above-identified patent and that said Letters Patent is hereby corrected as shown below:

Col. 27, line 16, the "3" should be a bracket.

Col. 27, line 31, "antiten" should be --antigen--.

Col. 27, line 56, "cystine" should be --cysteine--.

Col. 28, line 44, "mycopnoenolic" should be --mycophoenolic--.

Col. 29, line 24, "1:410" should be --5:410--.

Col. 29, line 40, "2:2013" should be --7:2013--.

Col. 29, line 51, "Spaere" should be --Spaete--.

Col. 31, line 22, "$\Delta 508$" should be --$\Delta F508$--.

Col. 31, line 41, after "the" (first occurrence) insert --MHS--.

Col. 31, line 57, "forth" should be --form--.

Col. 31, line 59, after "base" insert --or--.

Col. 32, line 62, "74" should be --7--.

Col. 32, line 64, "errand" should be --strand--.

Col. 33, line 11, "Mississauca" should be --Mississauga--.

UNITED STATES PATENT AND TRADEMARK OFFICE
CERTIFICATE OF CORRECTION

PATENT NO. : 5,358,649

DATED : October 25, 1994

INVENTOR(S) : MacLennan et al.

It is certified that error appears in the above-identified patent and that said Letters Patent is hereby corrected as shown below:

Col. 33, line 28, "aliguot" should be --aliquot--.

Col. 33, line 35, "Denbarr's" should be --Denharts--.

Col. 33, line 63, "MM" should be --MH--.

Col. 33, line 65, "MM" should be --MH--.

Col. 33, line 67, "MM" should be --MH--.

Col. 34, line 24, "agohist" should be --agonist--.

Col. 34, line 25, "agohist" should be --agonist--.

Col. 35, line 24, "...KA-3'" should be --...AA-3'--.

Col. 35, line 27, "Denbarr's" should be --Denhart's--.

Col. 36, line 41, "piper" should be --pipet--.

Col. 36, line 48, "Proteinass" should be --Proteinase--.

Col. 37, line 42, "polylnerase" should be --polymerase--.

Col. 37, lines 58-59, omit "reverse primer is 5'-TTCACCGGAGTGGAGTCTCTGAGT-3'".

Col. 38, line 15, "50" should be --52--.

Col. 38, line 16, before "sec" insert --10--.

UNITED STATES PATENT AND TRADEMARK OFFICE
CERTIFICATE OF CORRECTION

PATENT NO. : 5,358,649

DATED : October 25, 1994

INVENTOR(S) : MacLennan et al.

It is certified that error appears in the above-identified patent and that said Letters Patent is hereby corrected as shown below:

Col. 38, line 31, "Tag" should be --Taq--.

Col. 38, line 31, "polymerass" should be --polymerase--.

Col. 38, line 32, "polymerass" should be --polymerase--.

Col. 38, line 32, "Tag" should be --Taq--.

Col. 38, line 33, "gens" should be --gene--.

Col. 39, after line 52, insert --of 10 mg/mL (final conc of 0.01%)--.

Col. 40, line 36, "nigh" should be --high--.

Col. 40, line 39, "Goelet" should be --Hoefer--.

Col. 40, line 50, "Has" should be --Hae--.

Col. 58, line 28, "PRC" should be --PCR--.

Signed and Sealed this

Twenty-second Day of October, 1996

Attest:

Attesting Officer

BRUCE LEHMAN

Commissioner of Patents and Trademarks